(12) United States Patent
Russ et al.

(10) Patent No.: US 12,594,306 B2
(45) Date of Patent: Apr. 7, 2026

(54) USE OF ENTPD3 FOR IDENTIFICATION, ISOLATION, AND ENHANCING MATURE STEM CELL DERIVED INSULIN-PRODUCING CELLS

(71) Applicant: THE REGENTS OF THE UNIVERSITY OF COLORADO, A BODY CORPORATE, Denver, CO (US)

(72) Inventors: Holger A. Russ, Denver, CO (US); Fiona Docherty, Aberdeen (GB)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 853 days.

(21) Appl. No.: 17/704,429

(22) Filed: Mar. 25, 2022

(65) Prior Publication Data

US 2022/0296652 A1     Sep. 22, 2022

Related U.S. Application Data

(63) Continuation of application No. PCT/US2020/055286, filed on Oct. 12, 2020.

(60) Provisional application No. 62/913,544, filed on Oct. 10, 2019.

(51) Int. Cl.
| | |
|---|---|
| *A61K 35/39* | (2015.01) |
| *C12N 5/071* | (2010.01) |
| *C12N 5/0735* | (2010.01) |

(52) U.S. Cl.
CPC ............ *A61K 35/39* (2013.01); *C12N 5/0606* (2013.01); *C12N 5/0678* (2013.01); *C12N 2501/117* (2013.01); *C12N 2501/16* (2013.01); *C12N 2501/335* (2013.01); *C12N 2501/36* (2013.01); *C12N 2506/02* (2013.01)

(58) Field of Classification Search
CPC ................................................... A61K 35/39
See application file for complete search history.

(56) References Cited

U.S. PATENT DOCUMENTS

| | | | |
|---|---|---|---|
| 7,556,930 B2 | 7/2009 | Johnson et al. | |
| 2014/0329704 A1 | 11/2014 | Melton et al. | |
| 2018/0216076 A1* | 8/2018 | Hebrok | A61K 35/39 |
| 2019/0177697 A1* | 6/2019 | Hebrok | A61P 3/10 |

FOREIGN PATENT DOCUMENTS

| | | |
|---|---|---|
| WO | WO 2015/02424 | 1/2015 |
| WO | 2018227176 A1 | 12/2018 |

OTHER PUBLICATIONS

Syed et al., 2013, Am. J. Physiol. Endocrinol. Metab. vol. 305, pp. E1319-E1326) (Year: 2013).*
Nair et al., "Recapitulating endocrine cell clustering in culture promotes maturation of human stem-cell-derived beta cells", Nat Cell Biol. Feb. 2019; 21(2): 236-274.
Syed et al., "Ectonucleotidase NTPDase3 is abundant in pancreatic β-cells and regulates glucose-induced insulin secretion," *Am J Physiol Endocrinaol Metab* 305: E1319-E1326, 2013.
Shahjalal et al., "Generation of pancreatic β cells for treatment of diabetes: advances and challenges," *Stem Cell Research and Therapy* (2018) 9:355, 19 pages.
Saunders et al., "Ectonucleoside Triphosphate Diphosphohydrolase-3 Antibody Targets Adult Human Pancreatic β Cells for In Vitro and In Vivo Analysis," *Cell Metabolism* 28, 745-754, Mar. 5, 2019.
Russ et al., "Controlled induction of human pancreatic progenitors produces functional beta-like dells in vitro," *The EMBO Journal*, vol. 34, No. 13, 2015, 1759-1771.
Hudish et al., "Modeling Hypoxia-Induced Neuropathies Using a Fast and Scalable Human Motor Neuron Differentiation System," *Stem Cell Reports*, vol. 14, 1033-1043, Jun. 9, 2020.
Docherty et al., "ENTPD3 Marks Mature Stem Cell-Derived β-Cells Formed by Self-Aggregation In Vitro," *Diabetes* 2021; 70:025541-2567.

* cited by examiner

*Primary Examiner* — Anoop K Singh
*Assistant Examiner* — David A Montanari
(74) *Attorney, Agent, or Firm* — Snell & Wilmer, L.L.P.; April Wurster

(57) ABSTRACT

Disclosed herein are methods, systems, and compositions for enhancing the effectiveness of β-cell (Beta-cell)-based therapies. Also disclosed herein are methods, systems, and compositions related to identifying, sorting and separating heterogeneous populations of stem cell-derived pancreatic β-cells (sBCs) into more useful and functionally homogeneous cell populations. In many embodiments, the most mature and functional of the sBCs are identified and live-sorted using the cell surface protein Ectonucleoside Triphosphate Diphosphohydrolase-3 (ENTP3), which is also referred to as CD39L3. The presently disclosed methods, systems, and compositions are useful for cell therapies, for example replacement therapy. In many embodiments the disclosed systems, methods, and compositions are useful in treatments for diabetes. In some embodiments, the disclosed methods, systems, and compositions may be useful in treating, preventing, and/or curing diabetes, for example type-1 diabetes.

13 Claims, 55 Drawing Sheets

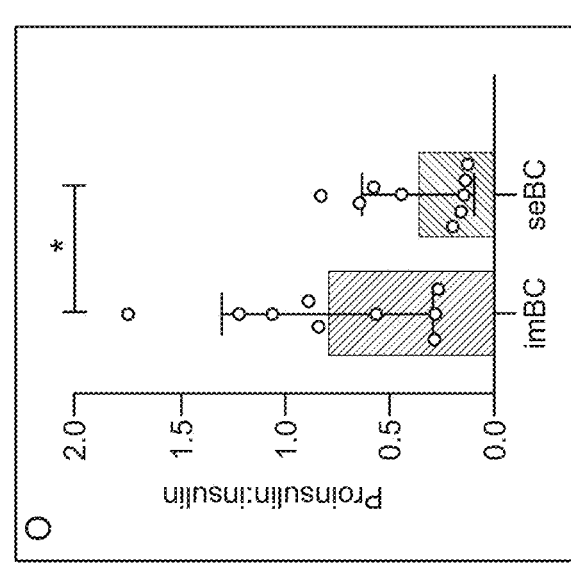
FIG. 1O
FIG. 1N
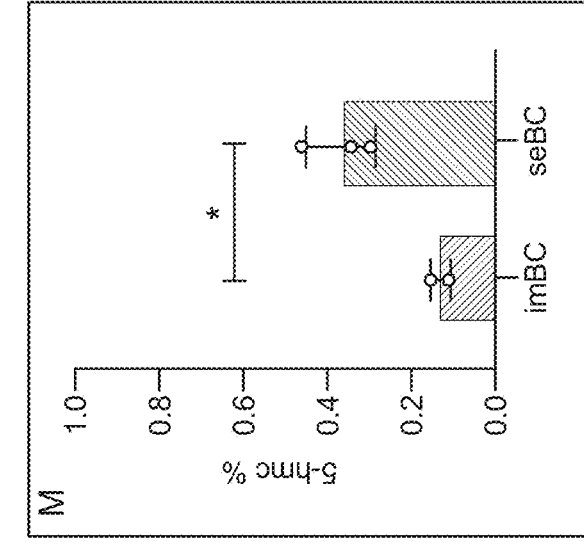
FIG. 1M

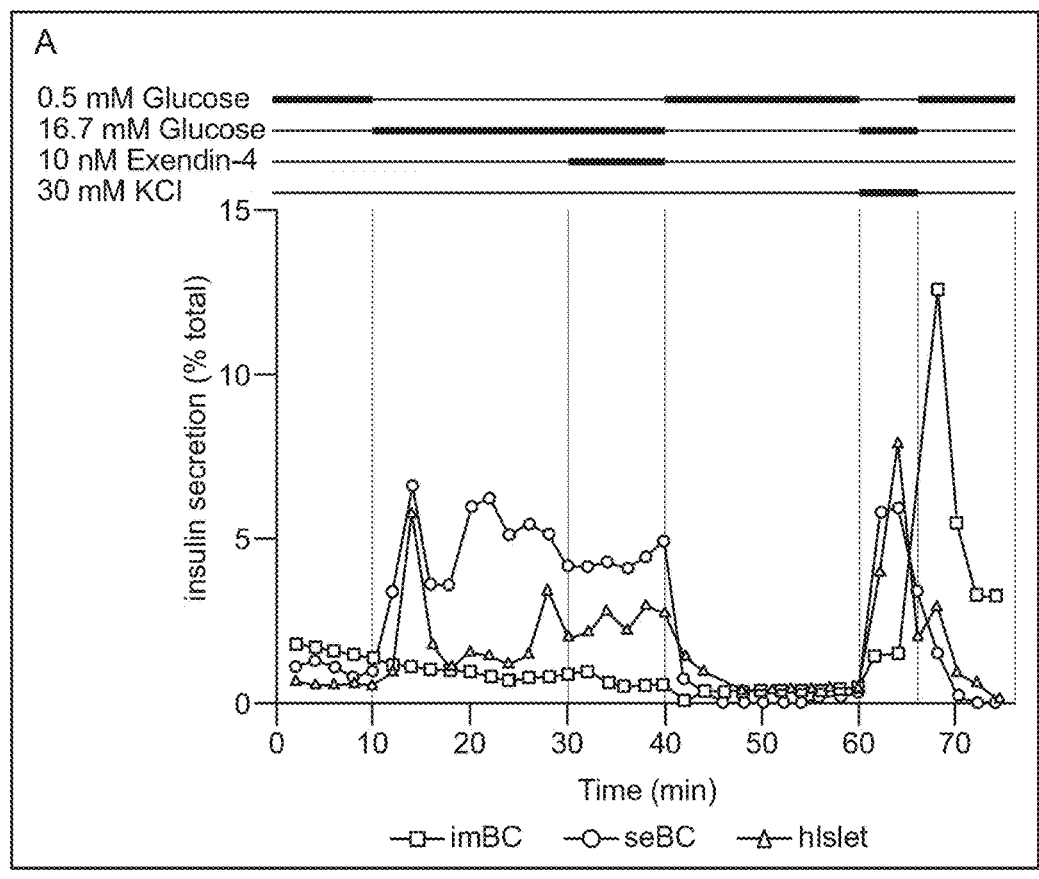
FIG. 2A
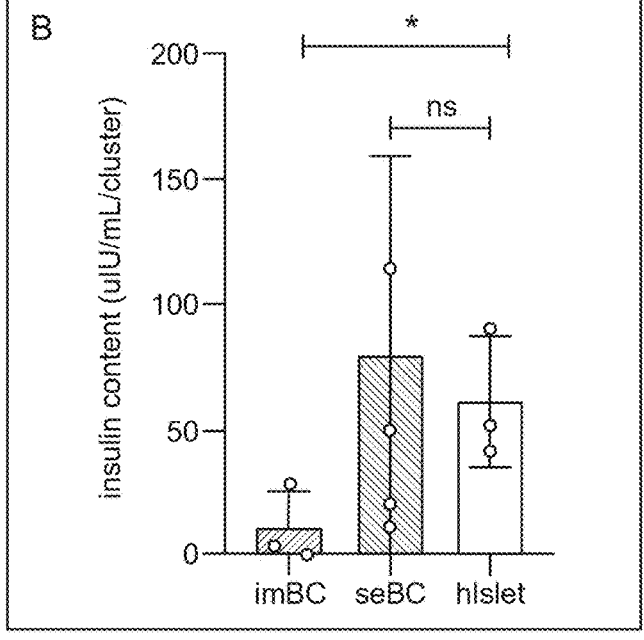
FIG. 2 B

FIG. 2E
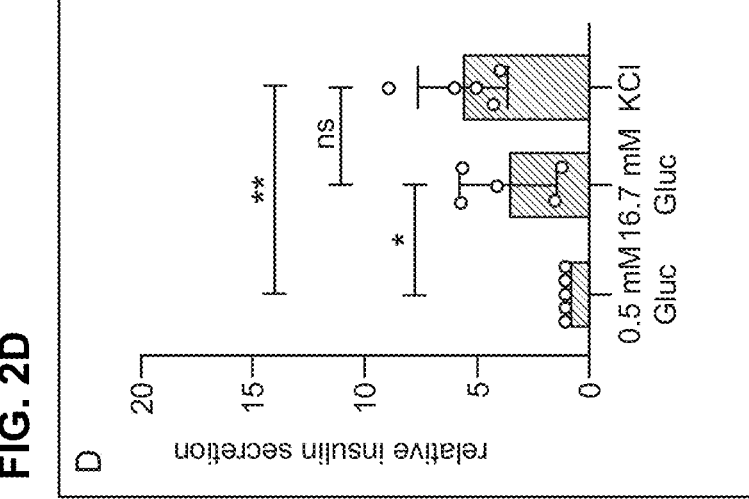
FIG. 2D
FIG. 2C
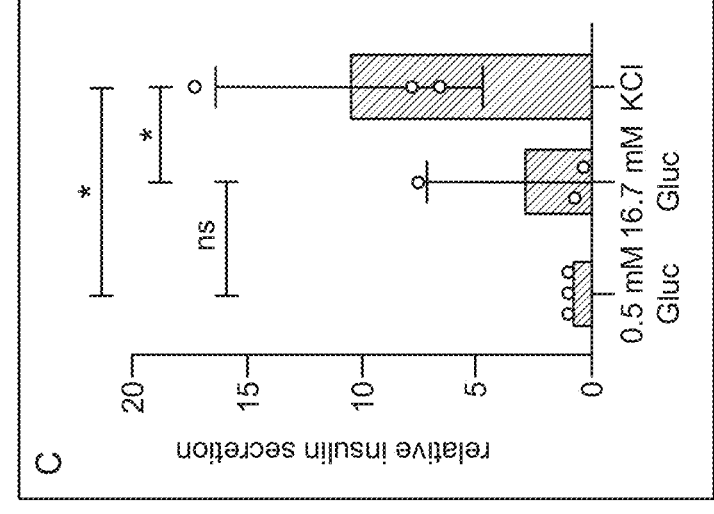

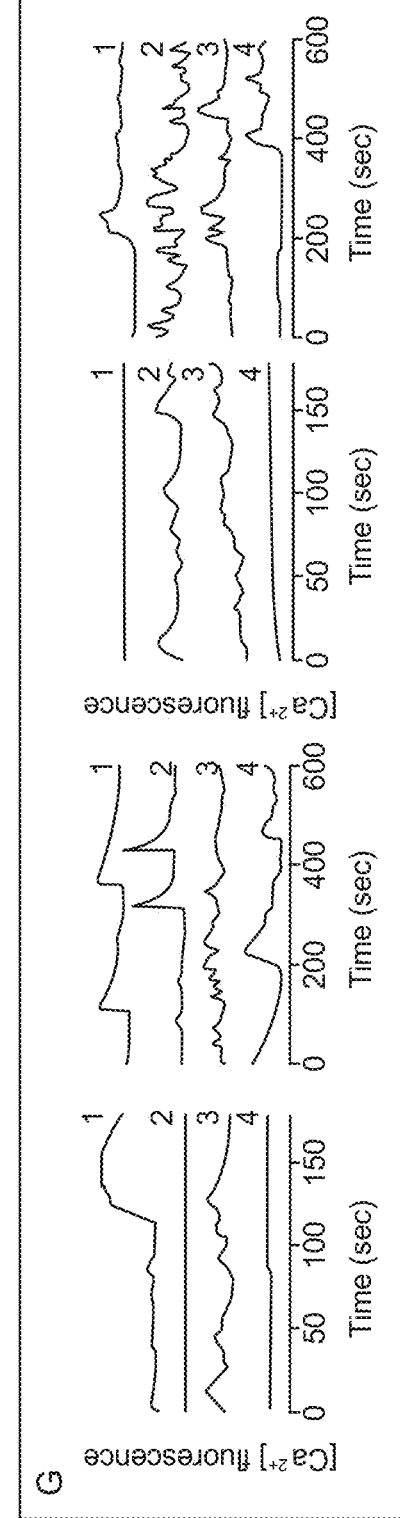
FIG. 2G
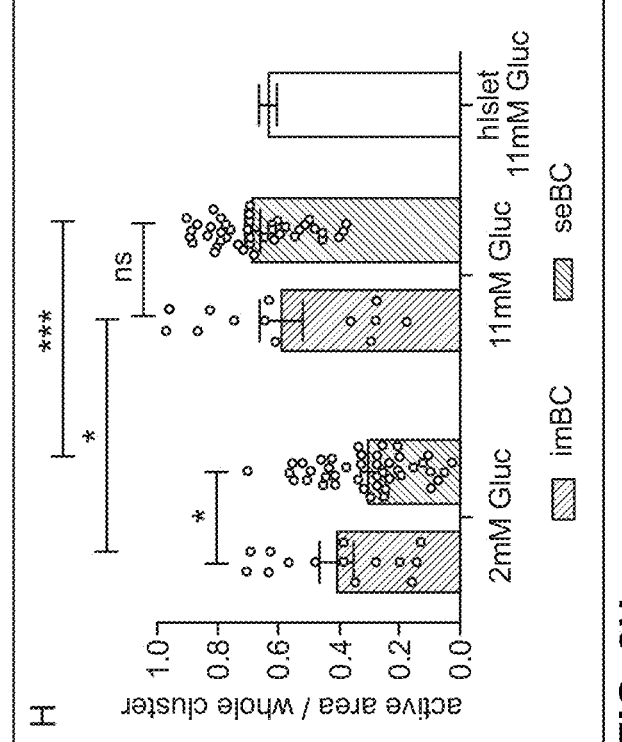
FIG. 2H
FIG. 2I

FIG. 5A
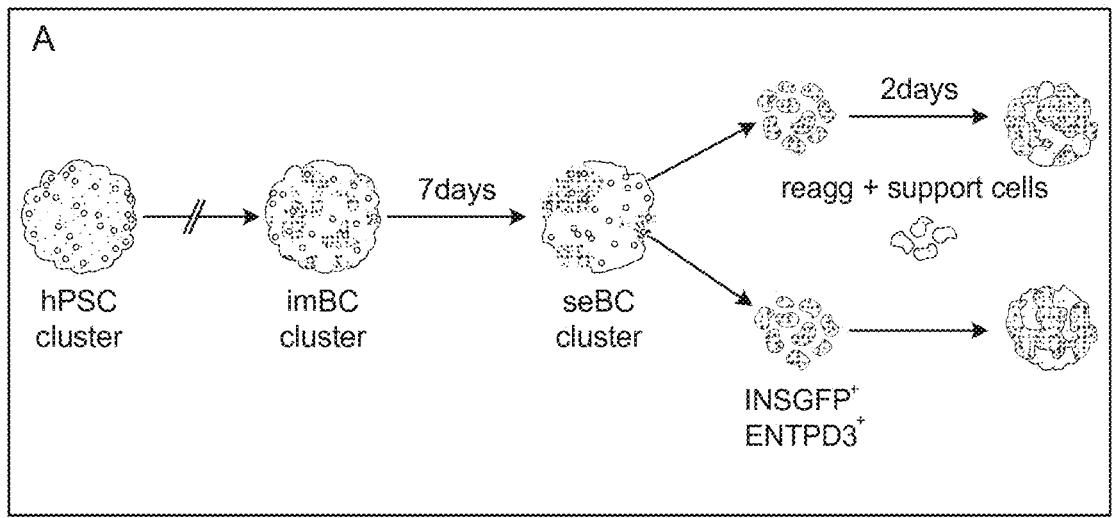
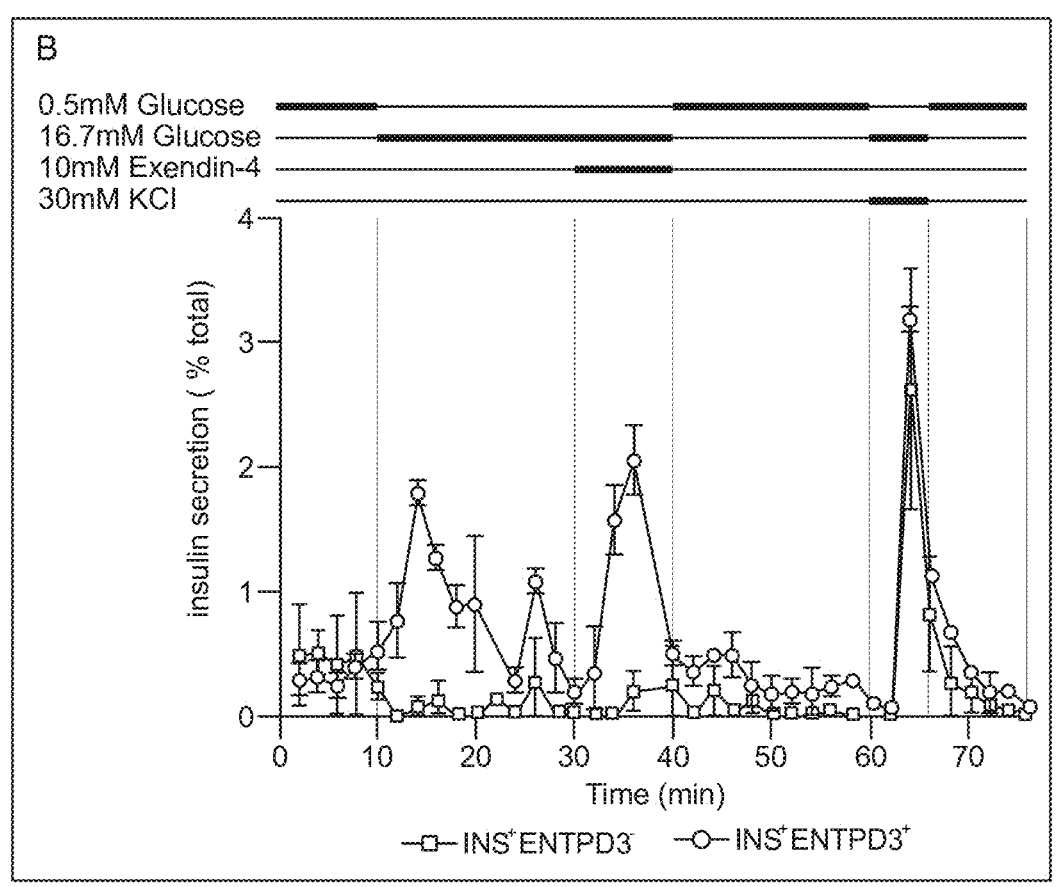
FIG. 5B

FIG. 7A
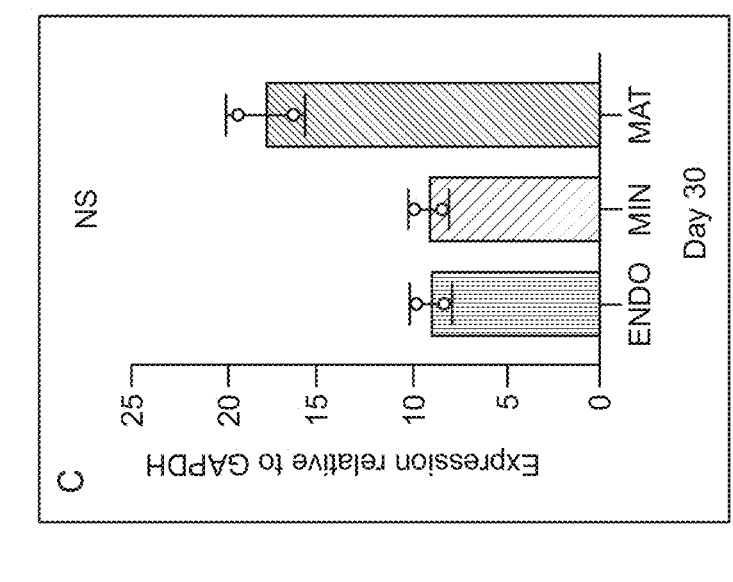
FIG. 7C
FIG. 7B
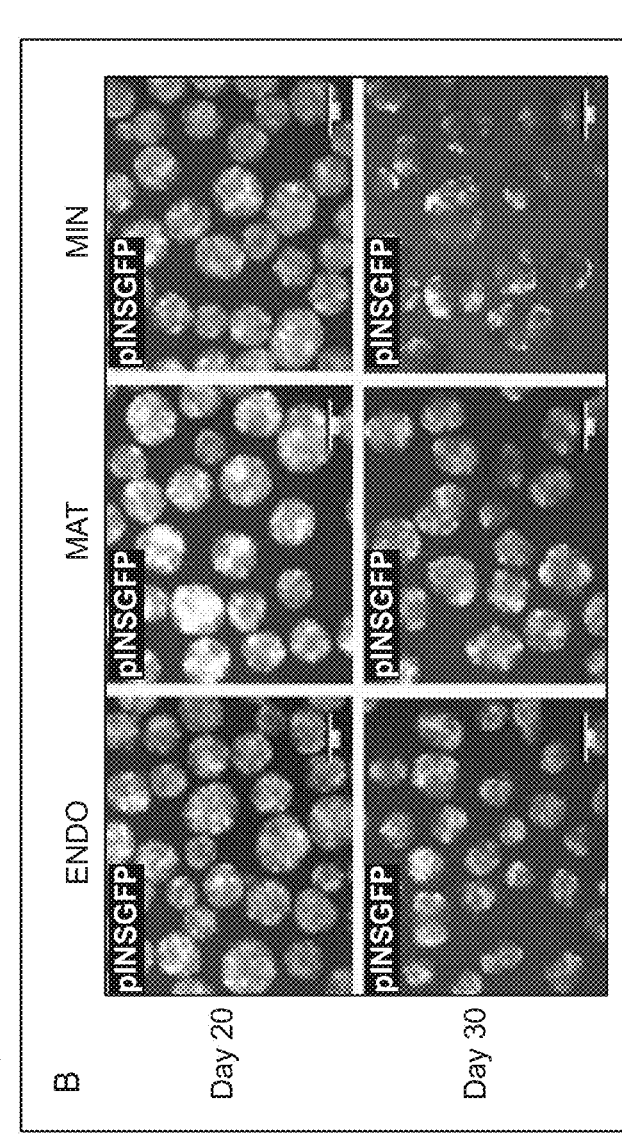

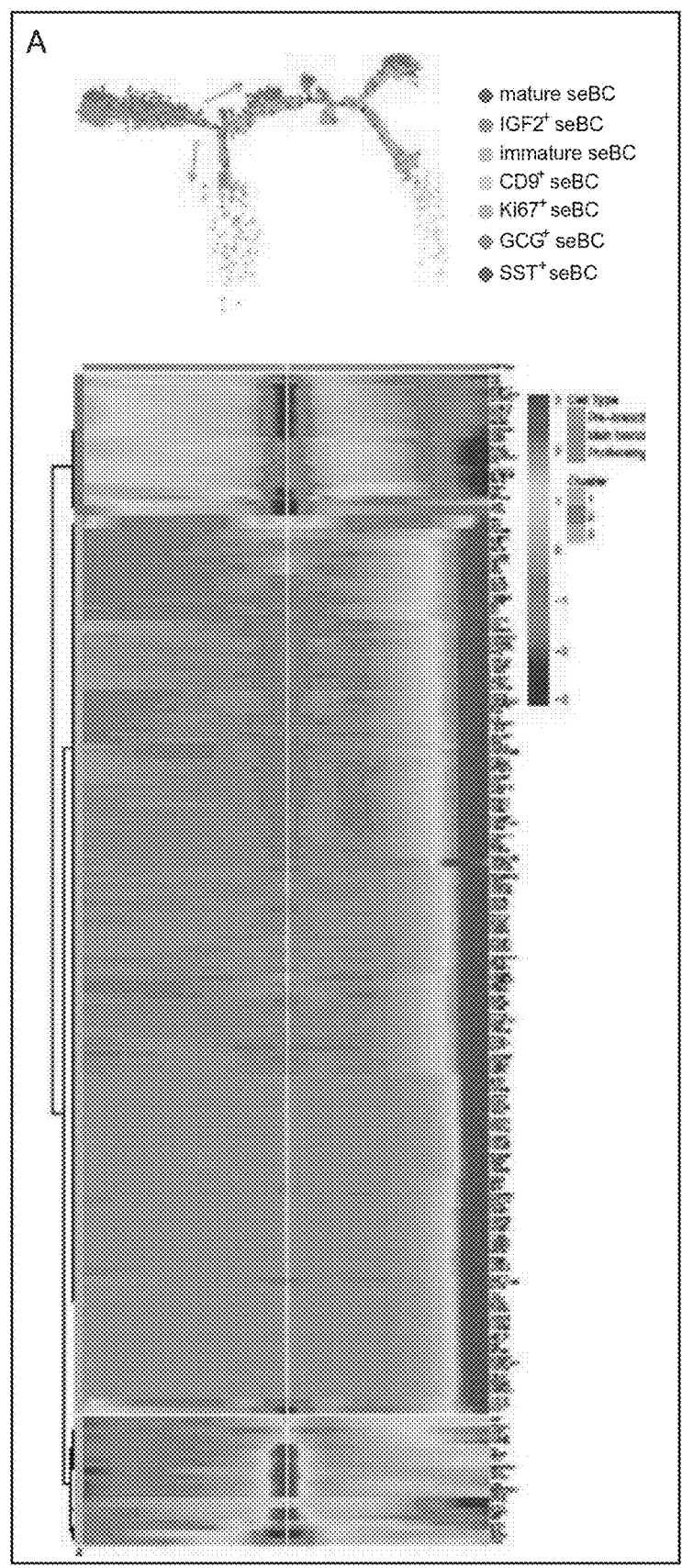
FIG. 9A

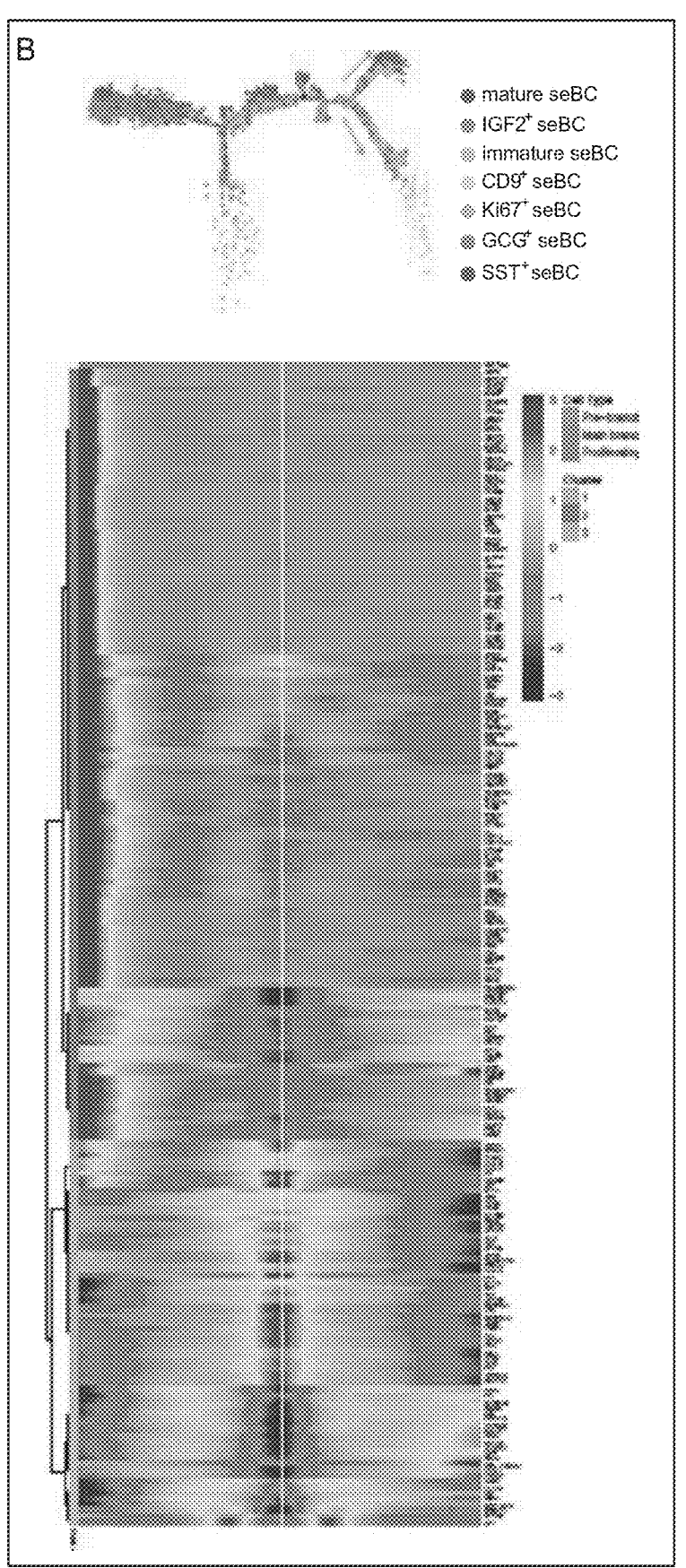
FIG. 9 B

FIG. 10G
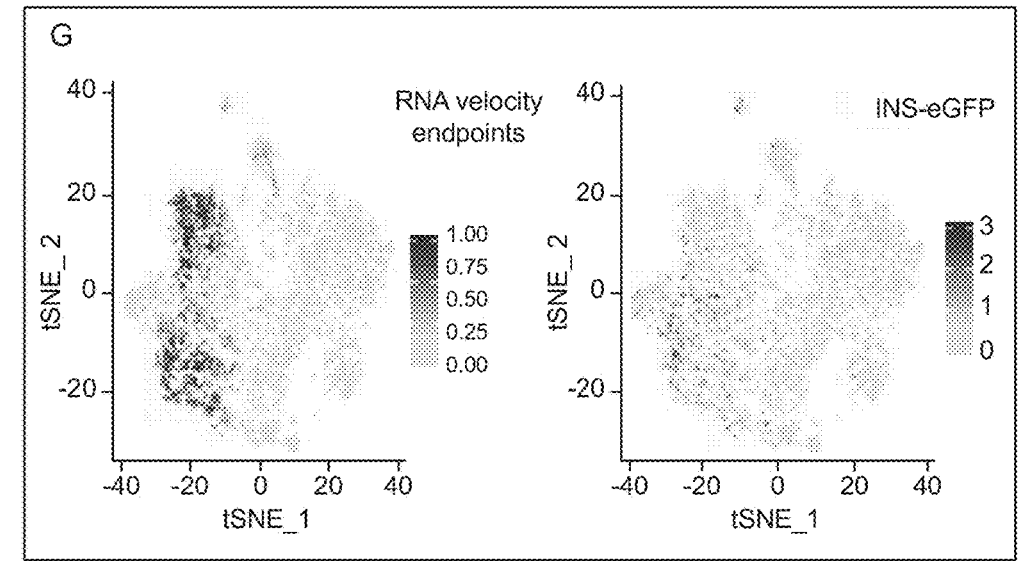
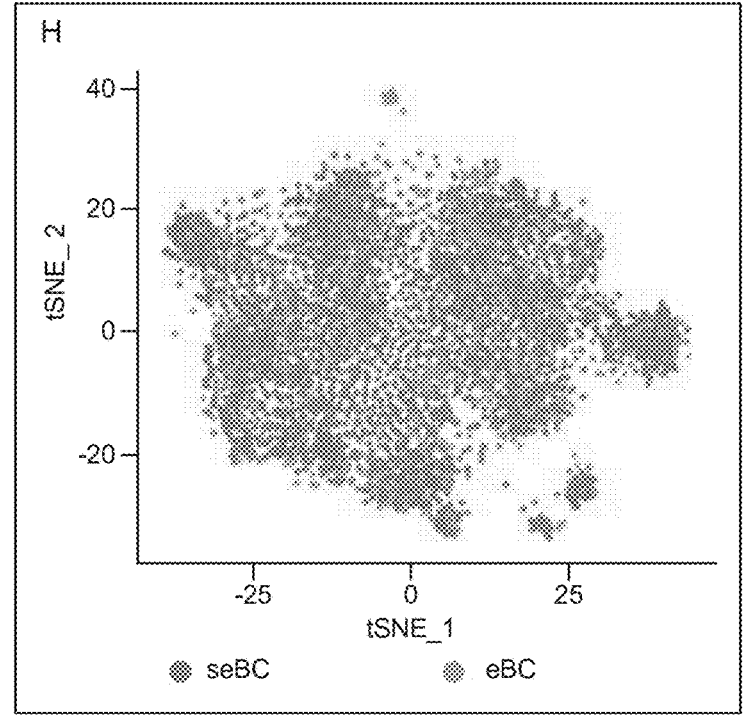
FIG. 10H

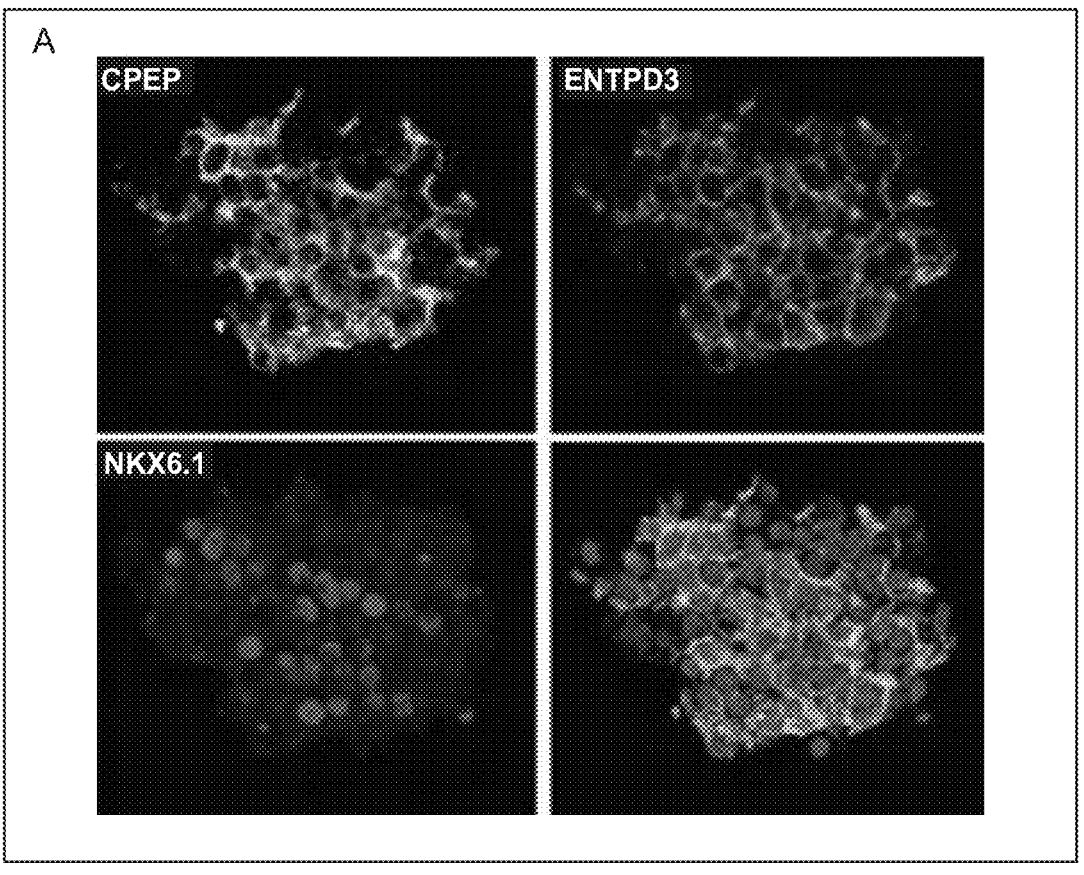
FIG. 12A

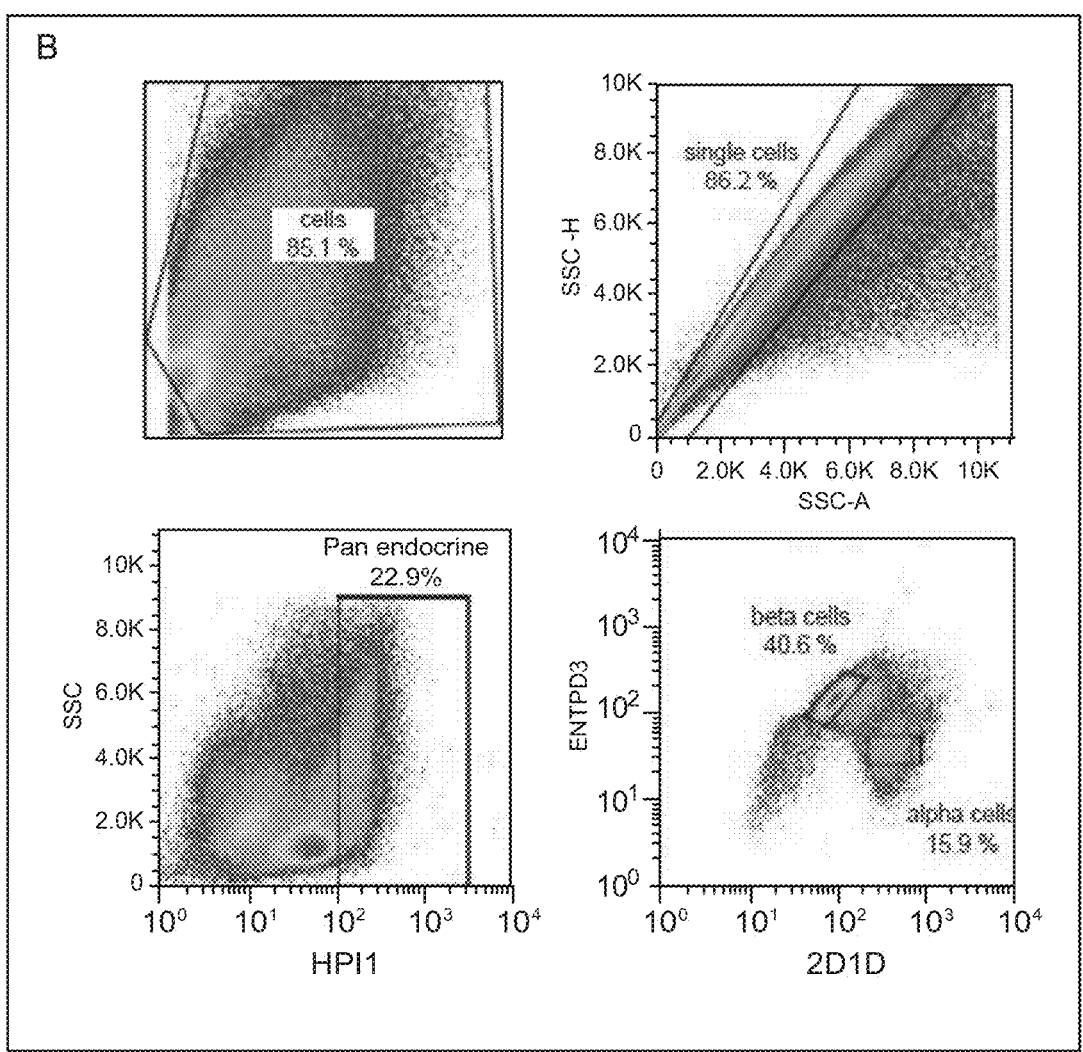
FIG. 12B

FIG. 12E
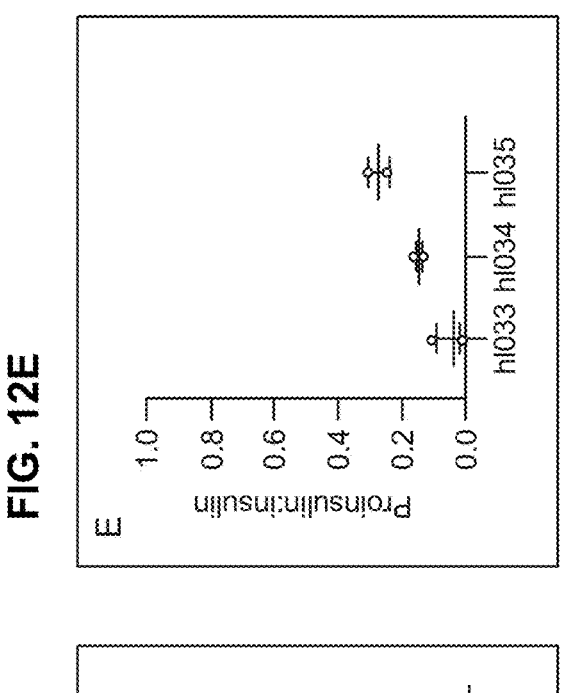
FIG. 12D
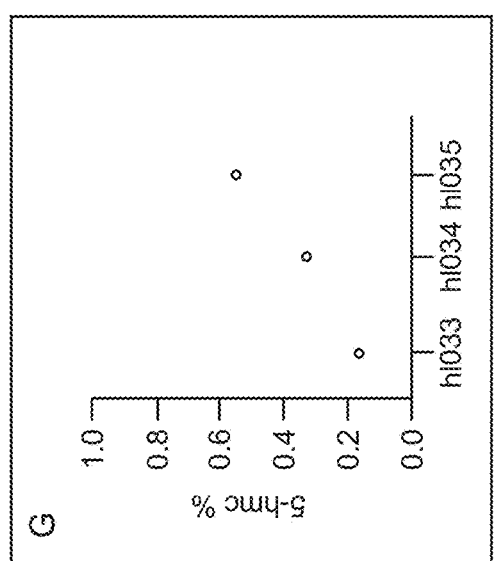
FIG.12G
FIG. 12F
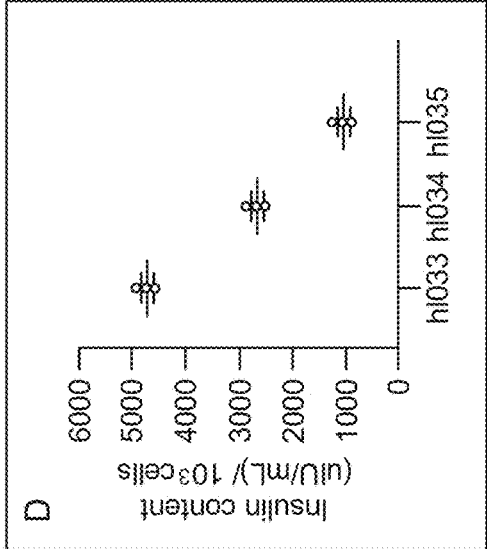
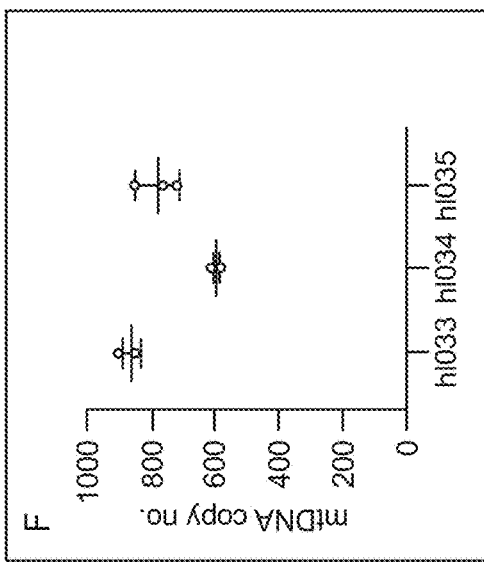

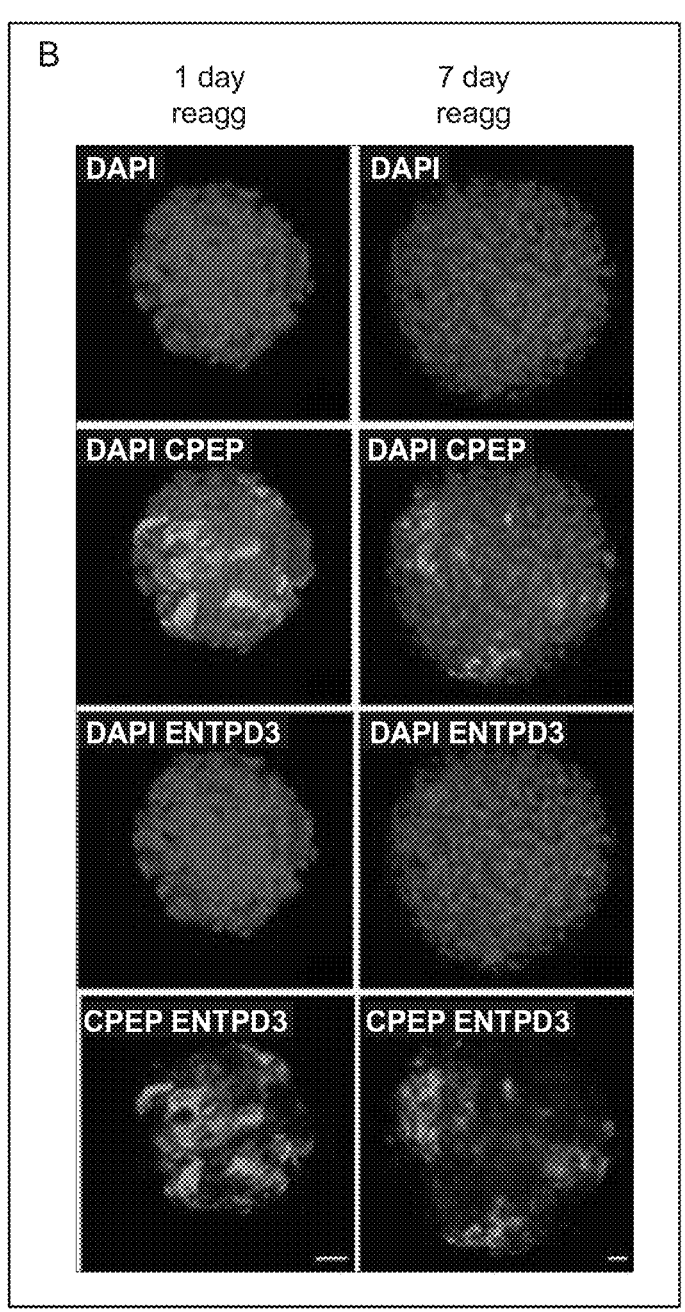
FIG. 13B

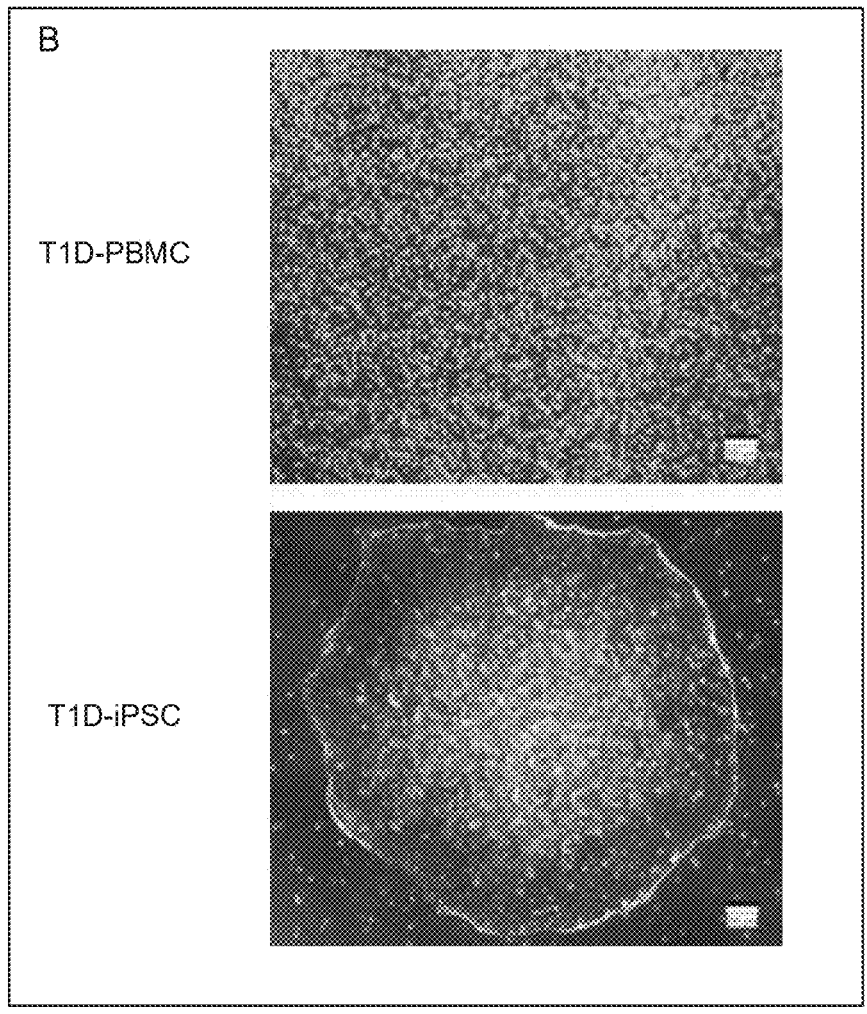
FIG. 14B

USE OF ENTPD3 FOR IDENTIFICATION, ISOLATION, AND ENHANCING MATURE STEM CELL DERIVED INSULIN-PRODUCING CELLS

CROSS-REFERENCE TO RELATED APPLICATIONS

This U.S. Continuation application claims the benefit of International Application, PCT/US20/55286 filed on Oct. 12, 2020 which claims the benefit of priority pursuant to 35 U.S.C. § 119(e) to U.S. provisional patent application No. 62/913,544 filed on Oct. 10, 2019. These applications are hereby incorporated by reference in their entirety for all purposes.

GOVERNMENT RIGHTS

This invention was made with government support under grant number RO1DK120444 awarded by the National Institutes of Health/National Institute of Diabetes and Digestive and Kidney Diseases. The government has certain rights in the invention.

FIELD

The disclosed processes, methods, and systems are directed to cell therapy treatments for diabetes.

SUMMARY

Disclosed herein are methods, systems, and compositions for enhancing the effectiveness of β-cell (Beta-cell)-based therapies. Also disclosed herein are methods, systems, and compositions related to identifying, sorting and separating heterogeneous populations of stem cell-derived pancreatic β-cells (sBCs) into more useful and functionally homogeneous cell populations. In many embodiments, the most mature and functional of the sBCs are identified and live-sorted using the cell surface protein Ectonucleoside Triphosphate Diphosphohydrolase-3 (ENTPD3), which is also referred to as CD39L3. The presently disclosed methods, systems, and compositions are useful for cell therapies, for example replacement therapy. In many embodiments the disclosed systems, methods, and compositions are useful in treatments for diabetes. In some embodiments, the disclosed methods, systems, and compositions may be useful in treating, preventing, and/or curing diabetes, for example type-1 diabetes.

BRIEF DESCRIPTION OF THE DRAWINGS

FIGS. 1A-1O. Stem cell-derived beta-like cells (sBC) self-enrich to form insulin+ enriched islet-like caps. FIG. 1A, schematic representation of step-wise differentiation of hPSC clusters towards beta-like cells in suspension. FIG. 1B, representative live image of green fluorescent protein driven by the endogenous insulin promoter (pINSGFP) of clusters during immature (imBC, day ~23) and self-enriched (seBC, day ~30) beta-like cell differentiation stages (scale bars indicate 200 µm). FIG. 1C, flow cytometric quantification of GFP expression in imBC and seBC clusters (n=7 independent differentiation experiments). FIG. 1D, quantification of GFP intensity in imBC and seBC clusters (n=6 independent differentiation experiments). FIG. 1M, global levels of 5-hydroxymethylcytosine in pINSGFP+ sorted cells (n=3 independent differentiation experiments). FIG. 1N & FIG. 1O, total insulin content (FIG. 1N) and proinsulin to insulin content ratios (FIG. 1O) per 1,000 pINSGFP+ sorted cells (n=3 independent differentiation experiments with 3×1,000 cells collected per experiment). *p<0.05p<0.01*p<0.001. Error bars are representative of the mean+/− the standard deviation. Scale bars represent 20 µm unless otherwise indicated.

FIGS. 2A-2I show data demonstrating seBC functional maturity. FIG. 2A, representative perifusion analysis of imBC, seBC and primary human islets (hIslets), 20-25 clusters were analyzed per sample and data is presented as % of total insulin in cluster pellet recovered. FIG. 2B, total insulin content of pellet recovered after perifusion and FIG. 3C, FIG. 2D, & FIG. 2E, relative insulin secretion during perifusion of imBC (n=3 independent differentiation experiments), seBC (n=5 independent differentiation experiments) and hIslet (n=3 independent human islets prep) respectively (data normalized to basal (0.5 mM Glucose) secretion). FIG. 2F, representative images of imBC (left) and seBC clusters (right) displaying Ca²⁺ indicator (Rhod-2) labelling, pINSGFP, and map (below) showing magnitude and extent of Ca²⁺ elevations at 2 mM and 11 mM glucose, scale bar is 10 µm and white arrows point to cells chosen for time courses in FIG. 2G. FIG. 2G, representative time courses of individual cells from the imBC and seBC clusters displayed in (FIG. 2F) at 2 mM and 11 mM glucose, scale bar is 50% change from mean. FIG. 2H, fraction of area within intact cluster showing elevations in Ca²⁺ activity at 2 mM and 11 mM glucose (n=3 independent differentiation experiments with >10 clusters measured per condition). Human islet data quantified in the same manner is included for reference Westacott, M. J. et al. (Age-dependent decline in the coordinated [Ca2+] and insulin secretory dynamics in human pancreatic islets. Diabetes 66, 2436-2445 (2017)). FIG. 2I, fold change in Ca²⁺ activity when glucose is elevated from 2 mM to 11 mM glucose (n=3 independent differentiation experiments with >10 clusters measured per condition). *p<0.05 p<0.01 *p<0.001. FIG. 2B—FIG. 2E, error bars are representative of the mean+/− the standard deviation. FIG. 2H and FIG. 2I, error bars are representative of the mean+/− SEM.

FIG. 3A, schematic representation of seBC production and sorting. FIG. 3B, tSNE projection of 4,143 seBC. Cells are colored by inferred cell type based on marker gene expression. FIG. 3C, heatmap showing scaled abundance of the top ten marker genes for each cell type identified by single cell RNA-seq analysis. FIG. 3D, tSNE projection with RNA velocity vector estimates overlayed. FIG. 3E & FIG. 3F, differentiation start-point (FIG. 3E) and end-point (FIG. 3F) modeled using a markov diffusion process on RNA velocity transmission probabilities. Start and end points were sampled from a uniform 100×100 grid, then imputed for all cells using K=10 K-nearest neighbor pooling. Values range from 0 (yellow) to 1 (dark blue). FIG. 3G, trajectory inference (monocle2) analysis with cells colored by cell type. FIG. 3H, heatmap of scaled gene expression of genes with varying expression across pseudotime. Genes were clustered into two clusters with k-means clustering and expression values were smoothed using cubic-spline interpolation. FIG. 3I, go-term enrichment analysis of marker genes of most mature seBC population identified by RNA velocity end-point analysis (>0.8 end-point density).

FIG. 4A, tSNE projection of RNA velocity endpoints, pINSGFP transgene and ENTPD3 (Gene ID: 956; see ncbi.nlm.nig.gov/956) expression in 4,143 seBC. FIG. 4I, go-term enrichment analysis of differentially expressed genes identified in bulk RNA seq. FIG. 4N, global levels of 5-hydroxymethylcytosine in INS+ENTPD3+ vs INS+ENTPD3- sorted cells from seBC day 30 and human islets (n=4 independent differentiation experiments, with 1×500 cells analyzed per experiment). *p<0.05p<0.01*p<0.001 error bars are representative of the mean+/-the standard deviation.

FIGS. 5A-5F and FIG. 6 show that INS+ENTPD3+ cells display improved function and are present in patient derived seBC. FIG. 5A, schematic representation of pINS+ENTPD3+/- cells sorted from seBC clusters reaggregated in the presence of support cells, human umbilical vein endothelial cells (HUVEC) and mesenchymal stem cells (MSC), for 48 h. FIG. 5B shows perifusion analysis of intact INS+ENTPD3- and INS+ENTPD3+ clusters, 20-25 clusters were analyzed per condition and data is presented as % of total insulin in cluster pellet recovered (n=2 independent differentiation experiments). FIG. 5C, total insulin content of clusters recovered following perifusion analysis (n=2 independent differentiation experiments). FIG. 5D relative insulin secretion during perifusion of INS+ENTPD3- and INS+ ENTPD3+ clusters (n=2 independent experiments) (data normalized to basal (0.5 mM Glucose) secretion). FIG. 5E, iPSC derived from a patient with type-1 diabetes (T1D-iPSC) were differentiated to seBC using an improved protocol, schematic representation. FIG. 5F, representative flow cytometry analysis of iPSC differentiation at definitive endoderm (DE), pancreatic endoderm (PE), imBC and seBC for specific lineage markers (n=2 independent differentiation experiments). FIG. 6, immunofluorescence staining of T1D-iPSC derived seBC clusters (scale bar represents 20 μm). Error bars are representative of the mean+/-the standard deviation, n=2 biological replicates.

FIGS. 7A-7C show pINSGFP+ caps form spontaneously and independently of maturation media. FIG. 7A, imBC clusters were cultured for 10 days in the presence of endocrine differentiation media (ENDO), maturation media (containing ALK5i and thyroid hormone (T3)) (MAT) and minimal maturation media (lacking ALK5i and T3 (MIN)), schematic representation. FIG. 7B, pINSGFP images of clusters in different media at day 20 and day 30 (scale bars represent 200 μm). FIG. 7C, quantitative PCR analysis of insulin gene expression in clusters at day 30 of differentiation. Error bars are representative of the mean+/- the standard deviation, n=2 independent differentiation experiments.

FIG. 8A fraction of area within intact cluster showing elevations in Ca$^{2+}$ activity of individual imBC and seBC clusters at 2 mM and 11 mM glucose (n=3 independent differentiation experiments with >10 clusters measured per condition). FIG. 8B, fraction of area within intact cluster exhibiting coordinated Ca$^{2+}$ activity (n=3 independent differentiation experiments with >10 clusters measured per condition). *p<0.05p<0.01*p<0.001 error bars are representative of the mean+/- SEM.

FIGS. 9A-9B show analysis of alternative beta cell differentiation trajectories identified by trajectory inference. FIG. 9A, Branchpoint Expression Analysis Modeling (BEAM) demonstrating top 200 genes differentially expressed across branches indicated by arrows. egfp shown in cluster 2 corresponds to the expression of the pINSGFP transgene. FIG. 9B, Same as FIG. 9A, but performed for the branch indicated by arrows.

FIG. 10A, schematic representation of eBC differentiation and sorting. FIG. 10B, tSNE projection of 4,178 eBC labeled by inferred cell types. FIG. 10C, heatmap showing scaled abundance of the top ten marker genes for each cell type identified by single cell RNA-seq. FIG. 10D, tSNE projection with RNA velocity vector estimates overlayed. FIG. 10E & FIG. 10F, differentiation start-point (FIG. 10E) and end-points (FIG. 10F) modeled using a markov diffusion process on RNA velocity transmission probabilities. Start and end points were sampled from a uniform 100×100 grid, then imputed for all cells using K=10 K-nearest neighbor pooling. Values range from 0 (yellow) to 1 (dark blue). FIG. 10G, RNA velocity endpoints (left) and INS-eGFP transgene expression (right) overlayed on tSNE projection. FIG. 10H, tSNE embedding of both seBC and eBC single cell RNA-seq datasets colored by respective dataset. Datasets were aligned using Seurat v2 integration methods. FIG. 10I, tSNE projections colored by the expression (log-normalized) of key genes related to beta-cell differentiation.

FIG. 11A, seBC were dissociated and sequentially incubated with anti-ENTPD3 (mouse) antibody and anti-mouse 555 secondary antibody then sorted first based on pINSGFP expression and second based on +/−ENTPD3-555. FIG. 11B. Cells were plotted on FSC vs SSC linear axes and gated to remove cell debris. Remaining cells were plotted by FSC area vs FSC height and gated to excluded non-single cells. Single cells were then plotted against DAPI stain and gated to remove dead cells. Live cells were plotted against pINSGFP reporter and those positive were then plotted for ENTPD3-555 in unstained, secondary antibody only and ENTPD3 conditions.

FIGS. 12A-12G show human islet sorting strategy. FIG. 12A, representative image of immunofluorescence staining of intact human islet sections with ENTPD3, c-PEP and NKX6.1 (Gene ID: 4825). FIG. 12B, representative gating strategy for ENTPD3+/− cells. FIG. 12C, quantification of immunofluorescence analysis of pancreatic hormone markers to verify presort and sorted populations (ENTPD3+/−) by single cell cytospin and counting using Image J analysis. FIG. 12D, insulin content per 1,000 pINSGFP+ENTPD3+ sorted cells (n=3 separate human islet preps, with 3×1,000 cell analyzed per prep). FIG. 12E, Proinsulin to insulin content molar ratio (n=3 separate human islet preps, with 3×1,000 cell analyzed per prep). FIG. 12F, quantitative PCR analysis of mtDNA normalized to gDNA in pINSGFP+ ENTPD3+ sorted cells (n=3 separate human islet preps, with 3×500 cell analyzed per prep). FIG. 12G, global levels of 5-hydoxmethylcytosine in pINSGFP+ENTPD3+ sorted cells (n=3 separate human islet preps, with 1×500 cell analyzed per prep). Error bars are representative of the mean+/−the standard deviation.

FIGS. 13A-13B show ENTPD3+ caps form continuously after removal of already formed pINSGFP+ENTPD3+ cells. FIG. 13A, seBC sorted for ENTPD3+/− and the ENTPD3+ cells discarded, the remaining pINSGFP+ and pINSGFP− cells reaggregated for 7 days in maturation media. FIG. 13B, immunofluorescence staining of reaggregated intact clusters collected after 1 and 7 days of culture (scale bar represents 20 μm).

FIGS. 14A-14F show T1D-iPSC established from patient-specific PBMC. FIG. 14A, schematic of type-1 diabetic induced pluripotent stem cell (T1D-iPSC) generation from patient-derived peripheral blood mononuclear cells (PBMC). PBMC were isolated from a blood drawn from a T1D patient and reprogrammed using episomal OKITA factor nucleofection to generate patient specific hiPSC. FIG. 14B, micrograph images of isolated T1D-PBMC and T1D-iPSC colony generated after reprograming (scale bar representation of 200 μm). FIG. 14C, representative karyotype of established T1D-iPSC line. FIG. 14D, quantitative PCR analysis for episomal vector expression in T1D-iPSC after 4 passages (positive control, PBMC 3 days after electroporation with episomal vector). FIG. 14E, quantitative PCR for key pluripotency factors in T1D-iPSC (expression normalized to GAPDH). FIG. 14F, immunofluorescence staining for key pluripotency transcription factors in T1D-iPSC (scale bar is representative of 50 μm).

Figures 15B, 15C:
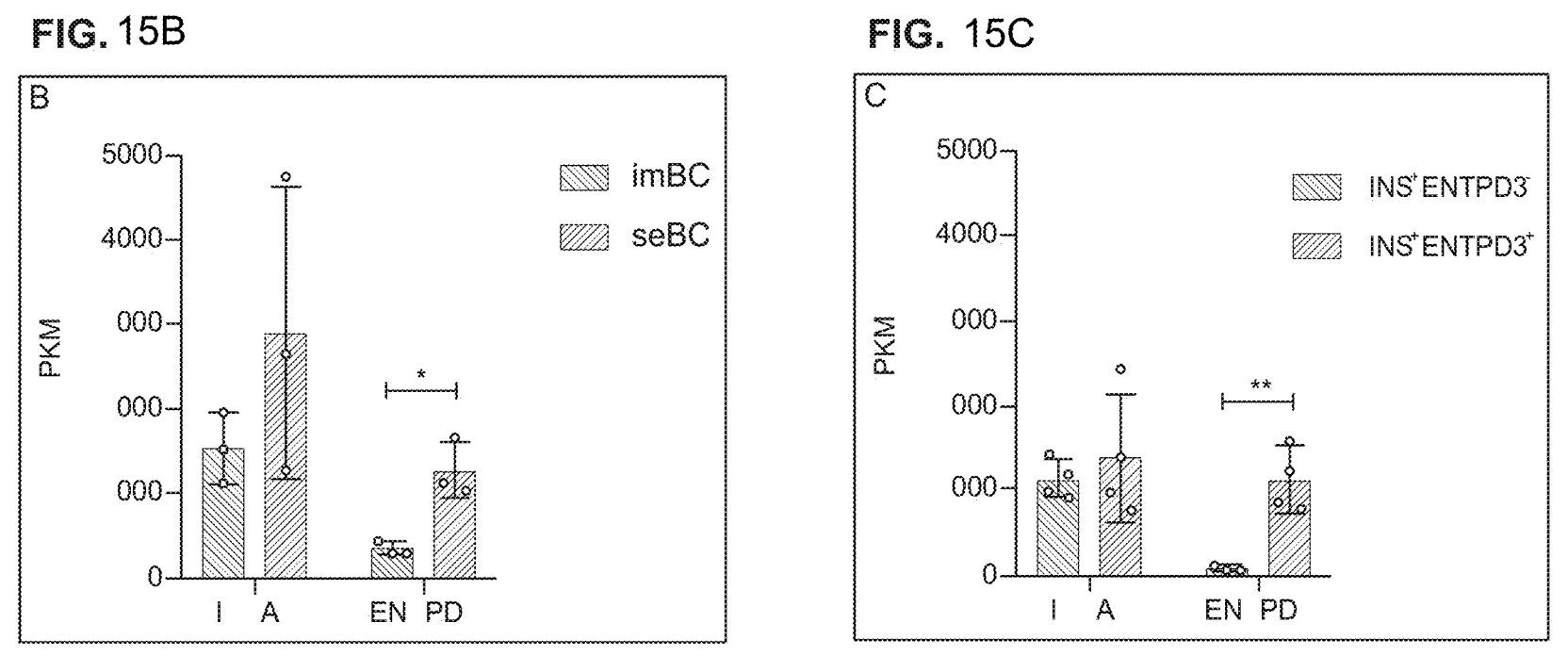

FIGS. 15A-15C show the beta cell surface marker ITGA1 displays wide spread expression across all maturity levels of pINSGFP+ seBC. FIG. 15A, tSNE projection of insulin transgene (pINSGFP), ENTPD3 and ITGA1 expression in 4,143 seBC. FIG. 15B, relative ITGA1 gene expression in pINSGFP+ imBC and seBC, (bulk RNA-seq experiment described in FIGS. 1A-1C). FIG. 15C, relative ITGA1 gene expression in pINSGFP+ENTPD3− and pINSGFP+ENTPD3+ cells (bulk RNA-seq experiment described in FIGS. 4A-4N). Error bars are representative of the mean+/−the standard deviation.

DETAILED DESCRIPTION

Figures 1A, 1B, 1C, 1D:
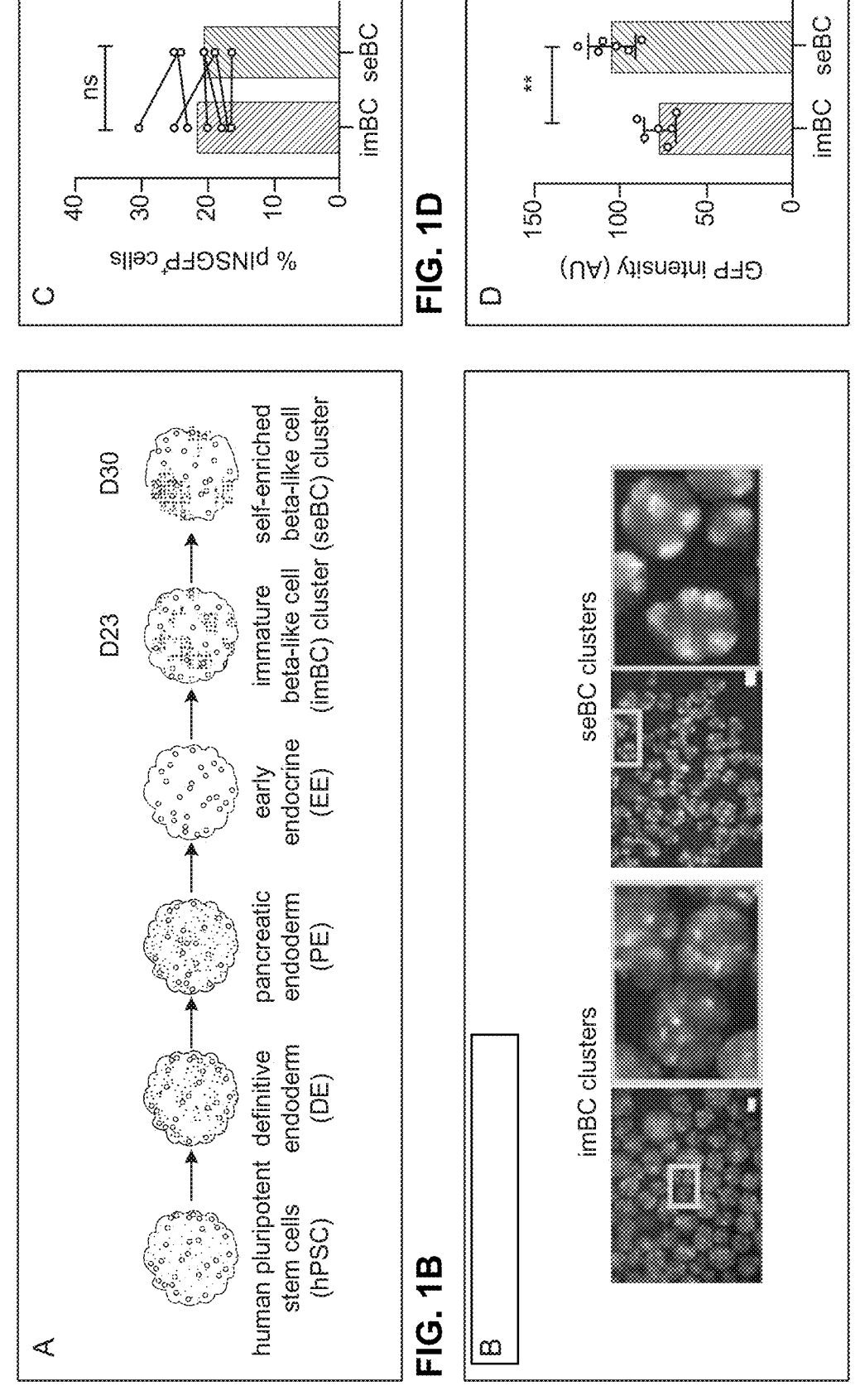

Stem cell derived insulin producing beta-like cells (sBCs) have emerged as an excellent research tool to study human pancreas/beta cell biology and show great promise for cell therapy treatments of patients in the clinic. Specifically, cell replacement therapy represents a potential cure for patients suffering from diabetes, including both type I and II. However, as yet, in vitro differentiation of β-like cells from human pluripotent stem cells (sBCs) results in cells that, albeit glucose responsive, phenotypically and functionally resemble human fetal β-cells rather than mature adult β-cells. This is not ideal, because unlike fully mature β-cells that release very little to no insulin at low glucose levels (from about 2.0 mM to about 5.6 mM) and exhibit a large response in insulin secretion in the presence of higher glucose levels (from about 5.6 to about 20 mM), fetal (and fetal-like) β-cells secret higher levels of insulin constitutively at low glucose levels and exhibit a blunted or undetectable increase in insulin secretion upon exposure to high glucose levels. Thus, mature β-cells represent a more desirable population for cell replacement therapy compared to immature β-cells due to their superior function and improved safety profile.

Typically, sBCs are generated by a step wise differentiation protocol that guides the cells through subsequent developmental steps, including pancreatic endoderm (PE), which is predominantly compromised of pancreatic progenitor cells. As noted above, previous studies have shown that transplantation of PE into preclinical animal models results in the generation of glucose responsive cells after several months. Indeed, first clinical trials are currently on the way to evaluating the potential of PE cells for cell replacement therapy to treat diabetes. However, due to the long time required for PE cells to differentiate into sBCs in vivo, and the relative heterogenous cell population of PE, a more defined and differentiated cell population is desirable for cell therapy approaches.

A pure, fully mature sBC population, that is functionally comparable to bona fide beta cells (such as those found in adult healthy individuals) is sought after for commercial purposes. As noted above, glucose responsive sBCs can be generated in vitro by optimization of differentiation conditions, but while the disclosed sBC respond to increases in glucose concentrations by secreting elevated levels of insulin (thus showing the cells to be functional), careful characterization of the cells reveals them to be a beta cell phenotype akin to fetal, immature beta cells, and thus not fully matured beta cells as found in healthy adults. While different approaches have been used to improve the sBC maturation state, success has been limited. These different approaches include artificial re-aggregation in enriched sBC clusters (eBCs), circadian entrainment, and/or further optimization of differentiation conditions.

Using an insulin promoter driven transgenic fluorescence reporter gene, Applicants show that sBCs can be sorted and reaggregated into enhanced beta-like clusters (eBCs, as described in Nair et al. "Recapitulating endocrine cell clustering in culture promotes maturation of human stem-cell-derived β cells" 2019, Nat. Cell Biol. 21, 263-274). eBCs exhibit further maturation into cells that are very closely matched to bona fide, adult human β-cells from donor tissues. Applicants note that cell therapy approaches using purified sBCs cells are desirable due to their enhanced functionality. In addition, this would allow a reduction in the total number of cells needed for transplantation by removing unwanted, not completely differentiated sBCs. Disclosed herein are methods, systems, and compositions that achieve these goals, without the need for expression of an exogenous reporter gene linked to insulin expression.

Disclosed herein are cell culture conditions that allow sBCs to actively self-sort and aggregate into distinct gaps within cell clusters. Characterization of seBC, by RNAseq, $Ca^{2+}$ signaling, transmission electron microscopy (TEM), hormone content, mitochondrial analysis and global methylation pattern, shows that they are phenotypically more mature than sBC and, similarly to eBCs, resemble bona fide beta cells. Specifically, proper Eph-ephrin signaling is required for attaining mature functionality in seBCs by lowering basal insulin secretion.

Using scRNAseq to investigate seBCs and eBCs Applicants surprisingly find that neither of these cell populations represent, as previously believed, homogenous populations. Rather, the both seBCs and eBCs can be clustered into different subpopulations, of which one cluster represents the most mature sBCs, as defined by insulin responsiveness (see above) and key gene marker expression (FIG. 3C, FIG. 3H, FIG. 10I) compared to all other clusters.

To be able to specifically sort for these most mature sBCs, Applicants have identified surface markers that specifically mark these cells and can be used to facilitate live cell sorting and isolation. Specifically, Applicants show that the surface marker ENTPD3 fulfills this criteria—allowing the separation and isolation of these β-cells from other cells. As disclosed herein, Applicants identify a novel cell surface marker that can be used to specifically label the most mature sBCs, which can be generated from either human embryonic stem cells or induced pluripotent stem cells. We anticipate that these results will have significant implications for current and future cell therapy strategies.

B-Cell Enrichment

The disclosed compounds, methods, and systems may aid in enriching for mature, functional β-cells. In many embodiments, the cells may be enriched from a population of cells that may include immature β-cells and/or a-cells. In some embodiments, the disclosed cells may be enriched from a population comprising less than about 50% mature β-cells, and the enriched population may be greater than about 90% mature β-cells. In many embodiments, mature ENTPD3 expressing cells may represent less than about 60%, 55%, 50%, 45%, 40%, 35%, 30%, 25%, 24%, 23%, 22%, 21%, 20%, 19%, 18%, 17%, 16%, 15%, 14%, 13%, 12%, 11%, 10%, 5% or 1% and greater than about 1%, 5%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, or 60% of a stem cell population before sorting/isolation. In many embodiments, after sorting/isolation these cells may represent greater than about 20%, 25%, 30%, 35%, 40%, 45%, 50%, 55%, 65%, 70%, 80%, 90%, or 95% and less that 100%, 95%, 90%, 80%, 70%, 65%, 60%, 55%, 50%, 45%, 40%, 35%, 30%, 25%, or 20% after sorting/isolation. In many embodiments, the remaining cells may include one or more of other hormone producing cells and support cells, for example mesenchymal, endothelial, pericytes, and nerve cells. In most embodiments, the presently disclosed mature β-cells express one or more of ENPTD3, INS, at levels that are greater than 2×, 3×, 4×, 5×, 10×, or 20× higher than the remaining population of cells after the enriched β-cells are removed.

ENTPD3-Binding Compounds

Populations of β- and β-like cells (for example more than about 10, 100, 1000, 1×10^6, 1×10^9 cells, or more) may be contacted by a compound having binding affinity for ENTPD3. In many embodiments, the disclosed compound with binding affinity for ENPTD3 may be an antibody, for example a monoclonal or polyclonal antibody. In one embodiment, the compound may be an antibody with affinity for human NTPDase3. In other embodiments, the disclosed compound may be selected from various single and multiple molecules including proteins, peptides, nucleopeptides, aptamers, and other compounds having affinity for ENPTD3. In many embodiments, the compound may be conjugated/connected to one or more detectable markers, for example a fluorescent marker that may aid in sorting cells non-covalently bound by the compound. The compounds with binding affinity for ENTPD3 may bind with a Kd of greater than 1 micromolar, for example 1 nanomolar higher, for example 1 picomolar or more, with little or no affinity for non ENTPD3 proteins, for affinity for non-ENPTD3 proteins may be greater than about 100× less, 1000× less, 10000× less, 1000000× less or more than affinity for ENTPD3.

Applicants have shown that ENTPD3 is enriched on the most mature sBCs. Isolation and characterization of these ENTPD3+ sBCs indicates that inclusion and enrichment of these cells for cell therapy treatments may help treat and/or cure diabetes. Cell replacement therapy represents a potential cure for type-1 diabetes; present methods for in vitro differentiation of β-like cells from human pluripotent stem cells results in production of cells that phenotypically and functionally resemble human fetal β cells.

Antibody may be immunoglobulin-based molecules that recognizes and specifically binds a target, such as a cell, protein, polypeptide, peptide, carbohydrate, polynucleotide, lipid, or combinations of the foregoing. Antibodies may be full-length monoclonal or polyclonal antibodies, as well as antibody fragments, such as Fab, Fab', F(ab')2, and Fv fragments, single chain Fv (scFv) mutants and Fc fusion proteins, including multi-specific and bispecific antibodies.

Treatment with Enriched β-Cells.

Use of the disclosed methods, systems, and compositions may result in more effective cell therapy treatments. In many embodiments, the cells may be mammalian, as may be the patients administered the cells. In many embodiments, the mammal may be selected from humans, dogs, and cats. As noted above, sBCs self-enrich into discrete, islets like structures within differentiated clusters (referred to as seBCs), in a process that improves cell maturation. Within seBCs the most mature sBCs can be identified by the mature beta cell marker ENTPD3. While, ENTPD3 does not appear to have a significant effect on maturation signaling, compounds with affinity for ENTPD3 can affect the maturation process.

A population of the disclosed ENTPD3-enriched β-cells may be administered to a subject in need thereof. In many embodiments, about 100×10^6 to about 600×10^6 ENTPD3-enriched β-cells may be administered, wherein about 30×10^6 to about 300^10^6, or more, are mature ENTPD3 expressing seBCs, for example greater than about 20×10^6 (20M), 30M, 40M, 50M, 60M, 70M, 80M, 90M, 100M, 110M, 120M, 130M, 140M, 150M, 160M, 170M, 180M, 190M, 200M, 250M, or 300M, and less than about 400M, 350M, 300M, 250M, 200M, 190M, 180M, 170M, 160M, 150M, 140M, 130M, 120M, 110M, 100M, or 500M. In many embodiments, a population of enriched β-cells may be administered to the subject by several methods including, injection, transplantation, implantation. In some embodiments, the disclosed population of ENTPD3-enriched β-cells may be administered to a patient in need thereof with or without a coating, capsule, or device to reduce or prevent rejection by the patient's immune system. In many embodiments, implantation of a population of cells may include a macro or micro immune-protective device, capsule, or coating. In some embodiment, cells are loaded into devices ex vivo or in vivo. In many embodiments, the site of injection may be one or more of intraperitoneal and hepatic portal vein, while transplantation may be at or near the omentum, liver lobes, intra peritoneal and sub-cutaneously. In some embodiments, the disclosed compositions and treatments may be contained in a pharmaceutical formulation. In most cases, a pharmaceutical formulation is a preparation that permits appropriate biological activity of the active ingredient (molecule, compound, cell, etc.), such that the active ingredient retains a biological effect. The formulation may include additional components, such as pharmaceutically acceptable excipients, buffers, pH stabilizers, salts, etc., and thus able to be administered to a mammalian subject.

Insulin Deficiency Disorders

The disclosed compositions, cells, methods, and systems may be useful in treating subjects with various disorders, diseases, conditions. In some embodiments, the disclosed disorders may be selected from diabetes, pancreatitis, trauma to the pancreas, infection of the pancreas, pancreatectomy, and pancreatic carcinoma.

Over time, immature stem cell derived β-like cells (SBC) self-aggregate in 3D culture forming insulin$^+$ 'caps' or self-enriched beta-like cells (seBC). Characterization of seBC, by RNAseq, Ca$^{2+}$ signaling, transmission electron microscopy (TEM), hormone content, mitochondrial analysis, global methylation pattern and responds profile to stimuli in dynamic secretion assays, shows that they are phenotypically more mature than SBC.

Disclosed herein are results, from single cell RNAseq, demonstrating that seBC are heterogenous and comprise populations of cells with varying maturity. Use of the disclosed methods and systems provide for a developmental trajectory towards mature β cell phenotypes under cell culture conditions described below. Analysis of the mature β cell subset has allowed identification of a novel mature β cell marker that can be used to specifically sort out the most mature cells from these heterogeneous cell populations.

Establishing these different models of β cell maturation has allowed us to begin elucidating the complex mechanisms that drive maturation of human β cells enabling better recapitulation of the process in vitro.

Finally, taking all of this together, we show that sorting and reaggregation of mature β cells from iPSC-derived from type-1 diabetic patients allows production of β-like cells that closely resemble mature human β cells. The disclosed methods, systems, and compositions, therefore, allow for producing clinically relevant cells for transplantation therapy.

Generation of Stem Cell Derived Beta-Like Cells from Human Embryonic Stem Cells

B-like cells may be generated from various sources. In one embodiment, the disclosed cells may be generated from undifferentiated human embryonic stem cells (hESC). In some embodiments, the cells may be MEL1 cells, that may contain an INSGFP/W reporter. In some embodiments, the cells may be maintained on hESC qualified Matrigel (Corning #354277) in mTESR1 or mTeSR+ media (STEMCELL Technologies #05826).

Differentiation to stem cell-derived beta-like cells (sBCs) may be carried out by various methods. In one embodiment, the cells are grown in suspension-based, low attachment suspension culture plates. In other embodiments, the cells may be grown in a bioreactor, with a magnetic stirring system (Reprocell #ABBWVS03A-6, #ABBWVDW-1013, #ABBWBP03N0S-6). Briefly, hESC cultures may be dissociated to create single cell suspensions. In some embodiments, confluent hESC cells may be collected and dissociated into single-cell suspension by incubation with TrypLE (Gibco #12-604-021) for about 6 min at about 37° C., and then quenched with mTESR media.

hESCs may be prepared at about $0.5 \times 10^6$ per ml in mTeSR media, wherein the media is supplemented with about 10 μM ROCK inhibitor (Y-27632, R&D Systems #1254-50) (cluster media). Sphere formation may be induced by growing the cells in bioreactors for about 48 h, wherein the bioreactors may be stirred at about 60 RPM at 5% $CO_2$. To induce definitive endoderm differentiation, spheres were collected in a 50 mL Falcon tube, allowed to settle by gravity, washed once with RPMI (Gibco #11-875-093)+0.2% FBS, and re-suspended in d 0 media (RPMI containing 0.2% FBS, 1:5,000 ITS (Gibco #41400-045), containing 100 ng/mL Activin-A (R&D Systems #338-AC-01M), and 3 μM CHIR (STEMCELL Technologies #72054)). Culture media was then changed daily by letting spheres settle by gravity for 3-10 min. supernatant (~80%) was removed by aspiration, and fresh media was added.

sBC differentiation has been described by Russ, H. A. et al. (Controlled induction of human pancreatic progenitors produces functional beta-like cells in vitro. EMBO J. 34, 1759-1772 (2015)) with modifications as outlined below. Differentiation medias are as follows: d 1 and 2, RPMI containing 0.2% FBS, 1:2,000 ITS, and 100 ng/LmL Activin A; d 3 and 4, RPMI containing 2% FBS, 1:1,000 ITS, and 25 ng/LmL KGF (Peprotech #100-19-1MG);); d 5, DMEM with 4.5 g/L D-glucose (Gibco #11960-044) containing 1:100 SM1 (STEMCELL Technologies #5711), 1:100 NEAA (Gibco #11140-050), 1 mM Sodium Pyruvate (Gibco #11360-070), 1:100 GlutaMAX (Gibco #35050-061), 3 nM TTNPB, (R&D Systems #0761), 250 nM Sant-1 (R&D Systems #1974), 250 nM LDN (STEMCELL Technologies #72149), 30 nM PMA (Sigma Aldrich #P1585-1MG), 50 μg/mL 2-phospho-L-ascorbic acid trisodium salt (VitC) (Sigma #49752-10G); d6, DMEM with 4.5 g/L D-glucose containing 1:100 SM1, 1:100 NEAA, 1 mM Sodium Pyruvate, 1:100 GlutaMAX, 3 nM TTNPB and 50 μg/mL VitC; d 7, addition of 100 ng/mL EGF (R&D Systems #236-EG-01M) and 50 μg/mL VitC to existing media; d 8 and 9, DMEM containing 1:100 SM1, 1:100 NEAA, 1 mM Sodium Pyruvate, 1:100 GlutaMAX, 100 ng/mL EGF, 25 ng/mL KGF, and 50 μg/mL VitC; d 10-16 DMEM containing 2% fraction V BSA, 1:100 NEAA, 1 mM Sodium Pyruvate, 1:100 GlutaMAX, 1:100 ITS, 10 μg/ml Heparin (Sigma #H3149-250KU), 2 mM N-Acetyl-L-cysteine (Cysteine) (Sigma #A9165-25G), 10 μM Zinc sulfate heptahydrate (Zinc) (Sigma #Z0251-100g), 1×BME, 10 μM Alk5i II RepSox (R&D Systems #3742/50), 1 μM 3,3',5-Triiodo-L-thyronine sodium salt (T3) (Sigma #T6397), 0.5 μM LDN, 1 μM Gamma Secretase Inhibitor XX (XXi) (AsisChem #ASIS-0149) and 1:250 1 M NaOH to adjust pH to ~7.4; d 17 and up, CMRL (Gibco #11530-037) containing 1% BSA, 1:100 NEAA, 1 mM Sodium Pyruvate, 1:100 GlutaMAX, 10 μg/mL Heparin, 2 mM Cysteine, 10 μM Zinc, 1×BME, 10

μM Alk5i II RepSox, 1 μM T3, 50 μg/mL VitC, and 1:250 NaOH to adjust pH to ~7.4. All media contained 1× Pen-Strep (Gibco #15140-122). At d11, all media was changed every other day.

Generation of Stem Cell-Derived Beta-Like Cells from Induced Pluripotent Stem Cells Induced pluripotent stem cells (iPSC) were derived from PBMC isolated from a type-1 diabetes patient (T1D-iPSC) and reprogrammed as described by Hudish, et al. (Modeling Hypoxia-Induced Neuropathies Using a Fast and Scalable Human Motor Neuron Differentiation System. Stem Cell Reports 14, 1033-1043 (2020))(FIGS. 14A-14F). iPSC were maintained on hESC qualified Matrigel in mTeSR+ media in 6 well plates. For differentiations 70-80% confluent cultures were washed with PBS and incubated in TrypLE for 8 min at 37° C. followed by quenching with mTeSR+. 0.5×10^6 cells/mL in mTeSR media supplemented with 10 μM ROCK inhibitor were seeded and differentiated as per hESC biore-actor differentiation protocol above, with the following modifications: d 4 and 5, 50 ng/mL KGF instead of 25 ng/mL; d 7, DMEM containing 1:100 SM1, 1:100 NEAA, 1 mM Sodium Pyruvate, 1:100 GlutaMAX, 3 nM TTNPB and 50 μg/mL VitC; d8 and d9, DMEM containing 1:100 SM1, 1:100 NEAA, 1 mM Sodium Pyruvate, 1:100 GlutaMAX, 200 ng/ml EGF and 50 ng/mL KGF; d 10-16, DMEM containing 2% fraction V BSA, 1:100 NEAA, 1 mM Sodium Pyruvate, 1:100 GlutaMAX, 1:100 ITS, 10 μg/ml Heparin, 2 mM Cysteine, 10 μM Zinc, 1×BME, 10 μM Alk5i II RepSox, 1 μM T3, 0.5 μM LDN, 10 μM RI, 1 μM Xxi and 1:250 1 M NaOH to adjust pH to ~7.4; d 17 and up, CMRL (Gibco #11530-037) containing 1% BSA, 1:100 NEAA, 1 mM Sodium Pyruvate, 1:100 GlutaMAX, 10 μg/mL Hepa-rin, 2 mM Cysteine, 10 μM Zinc, 1×BME, 10 μM Alk5i II RepSox, 1 μM T3, 50 μg/mL VitC, and 1:250 NaOH to adjust pH to ~7.4 (also referred to as maturation media). All media contained 1× PenStrep. Media was changed every other day starting d11.

The disclosed sorted seBCs may be obtained from stem cells as is known in the art. In many embodiments, the disclosed seBCs may be derived from embryonic or induced pluripotent stem cells from a donor's stem, progenitor, or adult cells, in most cases the cells are selected from blood or skin cells, for example peripheral blood mononuclear cells (PBMCs). One embodiment may include the method of Hudish, et al. as described in "Modeling Hypoxia-Induced Neuropathies Using a Fast and Scalable Human Motor Neuron Differentiation System" Stem Cell Reports 14, 1033-1043 (2020).

The iPSCs for generation of the presently disclosed stem cell-derived β-like cells may be used for autologous and/or allogenic therapies and uses. In some embodiments, allogenic cells for use with the described therapies, may include one or more engineered genomic changes directed to one or more immune genes/molecules, for example one or more of MHCs, HLA, and immune check point genes. In various embodiments, for example where autologous cell therapies are used, the cells may include one or more genes or mutations to correct one or more diseases, conditions, or characteristics of the patient's cells. In most embodiments, the presently disclosed stem cell derived β-like cells may include one or more copies of exogenous genes selected from OCT4, SOX2, NANOG and MYC.

Disaggregation/Reaggregation

Human Umbilical Vein Endothelial Cells (HUVEC) (Lonza #C2519A) human mesenchymal stem cells (hMSC) (Lonza #PT-2501) were grown as per manufactures instruc-tion. For reaggregation experiments a total of 1,000 sBC were sorted and reaggregated with 100 hMSC and 400 HUVEC cells for 2 days in round bottom plates in a 50:50 mixture of maturation and HUVEC culture media.

seBC Exhibit Enhanced ENTPD3 Gene Expression

The disclosed sorted seBCs may exhibit enhanced expres-sion of various genes. In many embodiments, the increase in expression may be greater than about 1.1×, 1.2×, 1.3×, 1.4×, 1.5×, 1.6×, 1.7×, 1.8×, 1.9×, 2×, 3×, 4×, 5×, 10×, or 20× and less than about 25×, 20×, 15×, 10×, 5×, 3×, 2×, 1.9×, 1.8×, 1.7×, 1.6×, 1.5×, 1.4×, 1.3×, 1.2×, or 1.1× compared to immature sBCs (imBCs). In many embodiments, the genes are selected from one or more of insulin, CPEP, and ENTPD3.

The disclosed sorted seBCs may exhibit significantly reduced or no expression of various hormones and genes, for example genes and hormones that are expressed in immature imBCs. In many embodiments, genes that are expressed at significantly reduced levels or are not expressed may be selected from one or more of SST, GCG, TPH1, and FEV. In many embodiments, hormones that are not expressed or expressed at significantly reduced levels may include one or more of Glucagon, Somatostatin, Pancreatic poly peptide, and ghrelin. In some embodiment, gene transcription may be expressed as RPKM or rpkm. RPKM, as is known in the art, describes reads per kilobase of transcript, per Million mapped reads. RPKM is a normalized unit of transcript expression, and is scaled by transcript length, such that it compensates for the fact that most RNA-sequencing proto-cols generate more sequencing reads from longer RNA molecules. In most embodiments, a gene that is not expressed, or expressed at significantly reduced levels may have a RPKM of about 150, for example less than 500, 450, 400, 350, 300, 250, 240, 230, 220, 210, 200, 190, 180, 170, 160, 150, 140, 130, 120, 110, 100, 90, 80, 70, 60, or 50, and more than about 10, 20, 40, 60, 80, 100, 150, 175, 200, 250, 300, 350, 400, 450, 500 or more. In many embodiment, a hormone may be said to be unexpressed or expressed at significantly reduced levels when its concentration is less than about 1×, 0.1× (one tenth the number of molecules), 0.01×, 0.001×, 0.0001× or less compared to expression of insulin.

Insulin Response

The disclosed sorted seBCs may possess enhanced insulin content and responsiveness that is better than imBCs, and is more similar to islet cells. In many embodiments, insulin content of a population of seBCs may be greater than a population of imBCs, for example by about 1× or more, for example 1.1×, 1.2×, 1.3×, 1.4×, 1.5×, 1.6×, 1.7×, 1.8×, 1.9×, 2×, 3×, 4×, 5×, 10× or more and less than about 20×, 10×, 5×, 3×, 2×, 1.9×, 1.8×, 1.7×, 1.6×, 1.5×, 1.4×, 1.3×, 1.2×, or 1.1×. In response to glucose, the insulin secretion by a population of seBCs may be greater than insulin secretion by a population of imBC, and may exhibit a spike in insulin secretion in response to 16.7 mM glucose of between 2 and 10%, for example greater than 2%, 3%, 4%, 5%, 6%, 7%, 8%, 9%, or 10%, and less than about 15%, 10%, 9%, 8%, 7%, 6%, 5%, 4%, 3%, or 2%.

Mitochondrial Content

The disclosed sorted seBCs may possess a greater amount of mitochondria than imBCs. In some embodiments, the number of mitochondria may be measured by comparing mitochondrial DNA of intensity of mitochondrial staining in a cell preparation. In many embodiments, the number of mitochondria in a population of seBC may be greater than about 1.1×, 1.2×, 1.3×, 1.4×, 1.5×, 1.6×, 1.7×, 1.8×, 1.9×, 2×, 3x, 4x, or 5x, and less than about 5x, 3x, 2x, 1.9x, 1.8x, 1.7x, 1.6x, 1.5x, 1.4x, 1.3x, 1.2x, or 1.1x that of a population of imBC.

Global Methylation Pattern

The disclosed sorted seBCs may possess enhanced DNA methylation content compared to imBCs. In many embodiments, the % methylation of a population of seBC may be greater than about 1.1x, 1.2x, 1.3x, 1.4x, 1.5x, 1.6x, 1.7x, 1.8x, 1.9x, 2x, 3x, 4x, or 5x, and less than about 5x, 3x, 2x, 1.9x, 1.8x, 1.7x, 1.6x, 1.5x, 1.4x, 1.3x, 1.2x, or 1.1x that of a population of imBC.

The presently disclosed sorted enhanced mature stem-cell derived β-cells typically react to glucose with a biphasic insulin release that is distinguishable from immature β-cells. In most cases, mature seBCs exhibit a clear first phase of insulin release, indicated by a brief spike of insulin secretion in response to glucose, for example 16.7 mM glucose, or greater than about 5 mM and less than about 20 mM. In addition, seBCs exhibit a sustained second phase of insulin secretion that is rapidly reverted when glucose levels are reduced, for example below 5 mM. In most embodiments, the presently disclosed cells may not release significant levels of insulin in response to glucose concentrations less than about 5 mM compared to imBCs. In most embodiments, immature β-cells, such as unsorted stem cell derived β- or β-like cells may secrete insulin in response to glucose concentrations of less than about 5 mM and may not show a first phase response to elevated glucose levels, for example 16.7 mM glucose. In most cases, a spike may be an increase of insulin secretion of between about 2 to 10 to 100 fold over basal secretion levels, for example from 1% to about 5% to 8% insulin secreted from total cellular insulin content, and occur between about 0 and 10 minutes after exposure to glucose greater than about 5.6 mM, for example about 16.7 mM. In most embodiments, a spike may occur more than 1, 2, 3, 4, 5, 6, 7, 8, 9, or 10 min. after glucose exposure and less than about 11, 10, 9, 8, 7, 6, 5, 4, 3, or 2 min. after exposure. In most cases, a second phase of insulin release may include a gradual reduction in insulin secretion that is less than the spike amount and may continue for about 30 minutes or more.

EXAMPLES

Example 1— Immature Stem Cell Derived Beta-Like Cells Spontaneously Self-Organize to Form Caps within Cell Clusters that Contain Matured Self-Enriched BC (seBC)

Figure 1E:
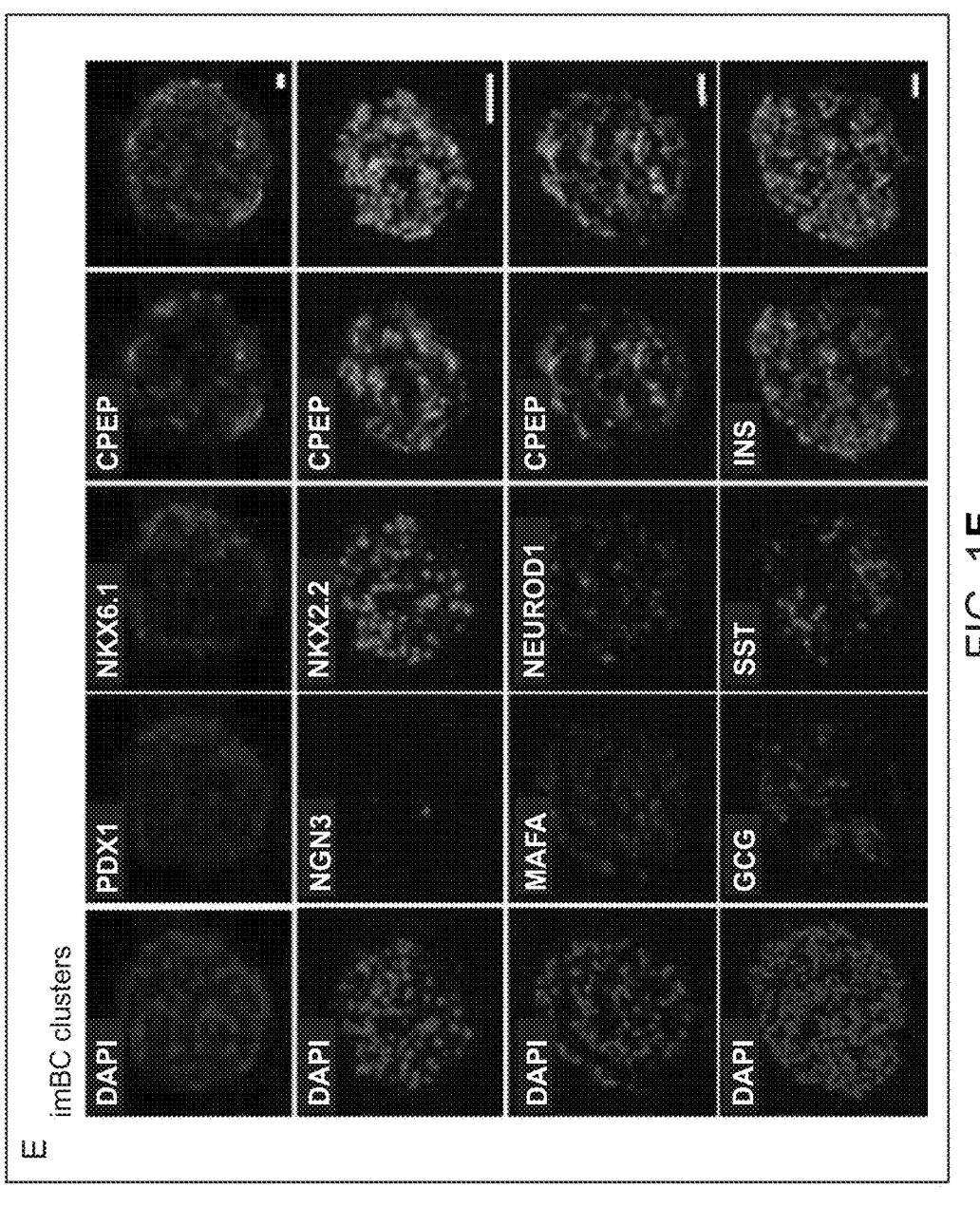
FIG. 1E & FIG. 1F, immunofluorescence analysis of sections from imBC and seBC clusters respectively for endocrine and β cell markers.
Figure 1F:
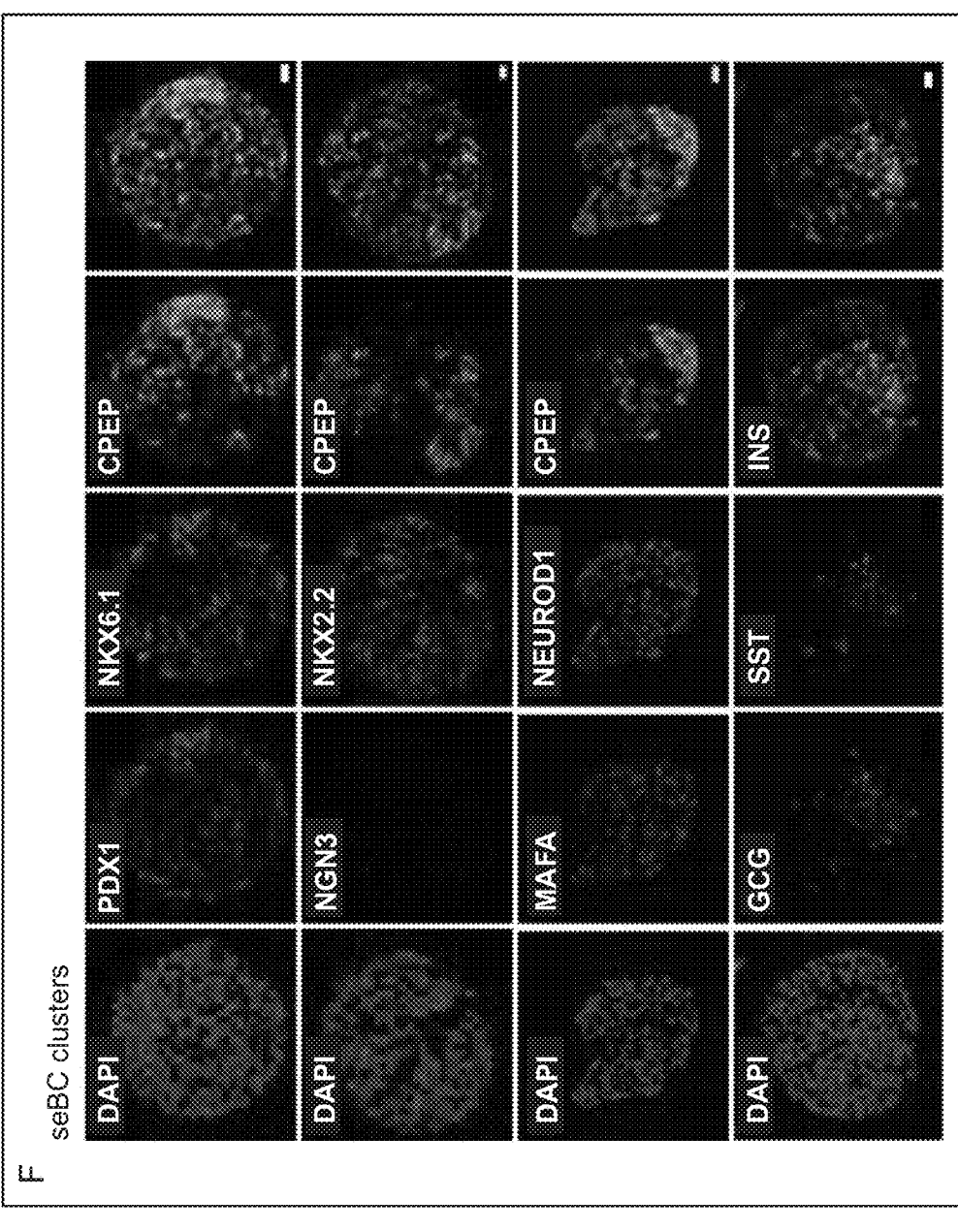

A human embryonic stem cell line that contains a green fluorescent protein (GFP) reporter gene under the control of the endogenous insulin promoter (herein referred to as pINSGFP) was used in the following experiments. These cells underwent a suspension culture-based direct differentiation protocol to generate glucose responsiveness, but remained largely immature sBC after approximately 23 days (imBC) (FIG. 1A). Use of GFP expression to visualize individual imBC revealed a heterogeneous distribution of insulin expression throughout individual clusters (FIG. 1B). Intriguingly, extending the culture period of sBC clusters by one-week resulted in spontaneous self-aggregation of imBC into discrete self-enriched beta-like cell (seBC) caps (FIG. 1B). seBC cap formation was not dependent on TGFbeta inhibition or the presence of T3 thyroid hormone, as imBC rearrangement was also observed in a minimal culture media without factors that could potentially exhibit confounding effects. However, sBC cultured in minimal media showed reduced levels of insulin expression, indicating optimal insulin expression is dependent on addition of factors at this culture stage (FIGS. 7A-7C). The percentage of pINSGFP+ cells remained constant during the self-aggregation process (FIG. 1C) suggesting that cap formation is not due to de novo production of sBC, but rather a result of active rearrangement of existing cells within each cluster. The intensity of pINSGFP fluorescence, which correlates with insulin expression, was significantly higher in seBC when compared to imBC (FIG. 1D). Analysis of common endocrine and beta cell markers and hormones by immunofluorescence staining showed no obvious differences in expression intensity or pattern in imBC and seBC clusters (FIG. 1E and FIG. 1F).

Figure 1G:
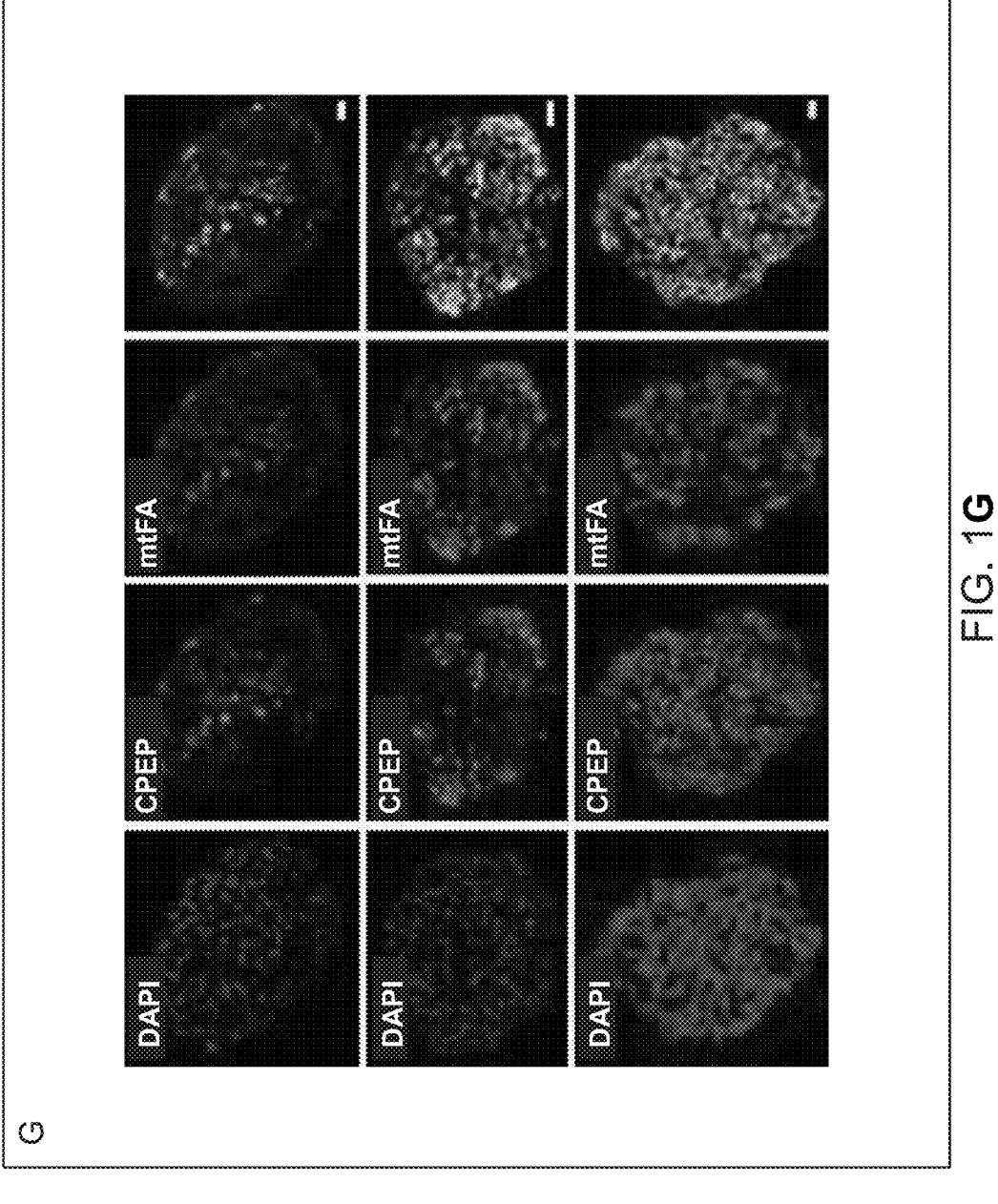
FIG. 1G, immunofluorescence analysis of sections from imBC clusters, seBC clusters and human islets for mitochondria specific mtFA protein.
Figure 1H:
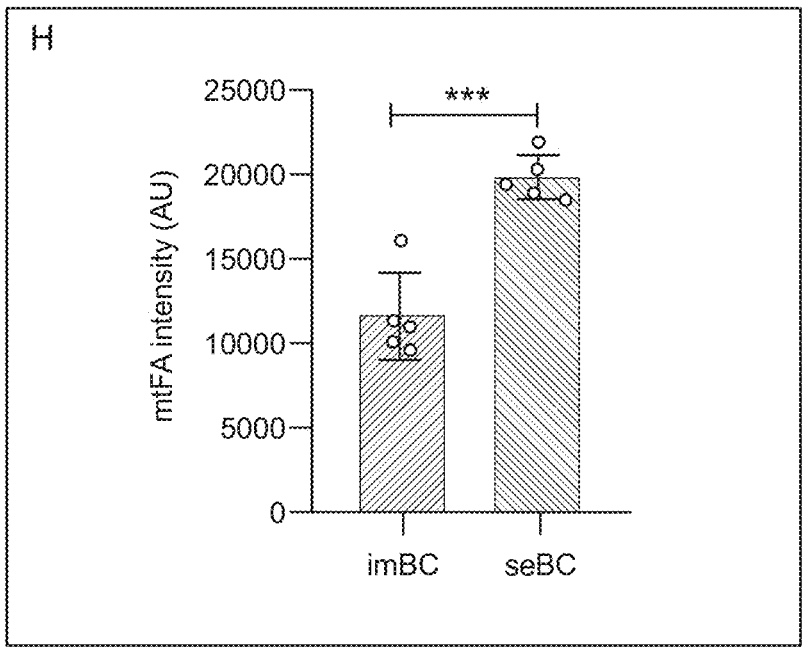
FIG. 1H, quantification of mtFA fluorescence intensity in imBC and seBC cells (n=5 independent differentiation experiments with 10 clusters analyzed per experiment).

Since mitochondrial number is known to increase with beta cell maturation, sBC mitochondria were stained for mtFA and quantified intensity quantified in imBC and seBC clusters. This analysis demonstrated significantly stronger mtFA staining intensity in seBC compared to the dispersed imBC cells indicating there was an increased number of mitochondria (FIG. 1G and FIG. 1H).

Figure 1I:
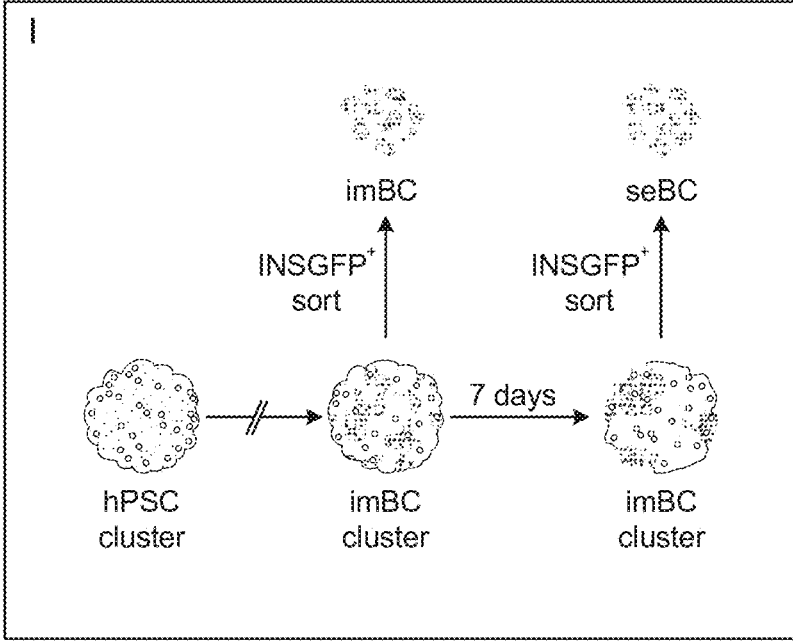
FIG. 1I, schematic representation of pINSGFP+ cell sorting from imBC and seBC clusters.
Figure 1J:
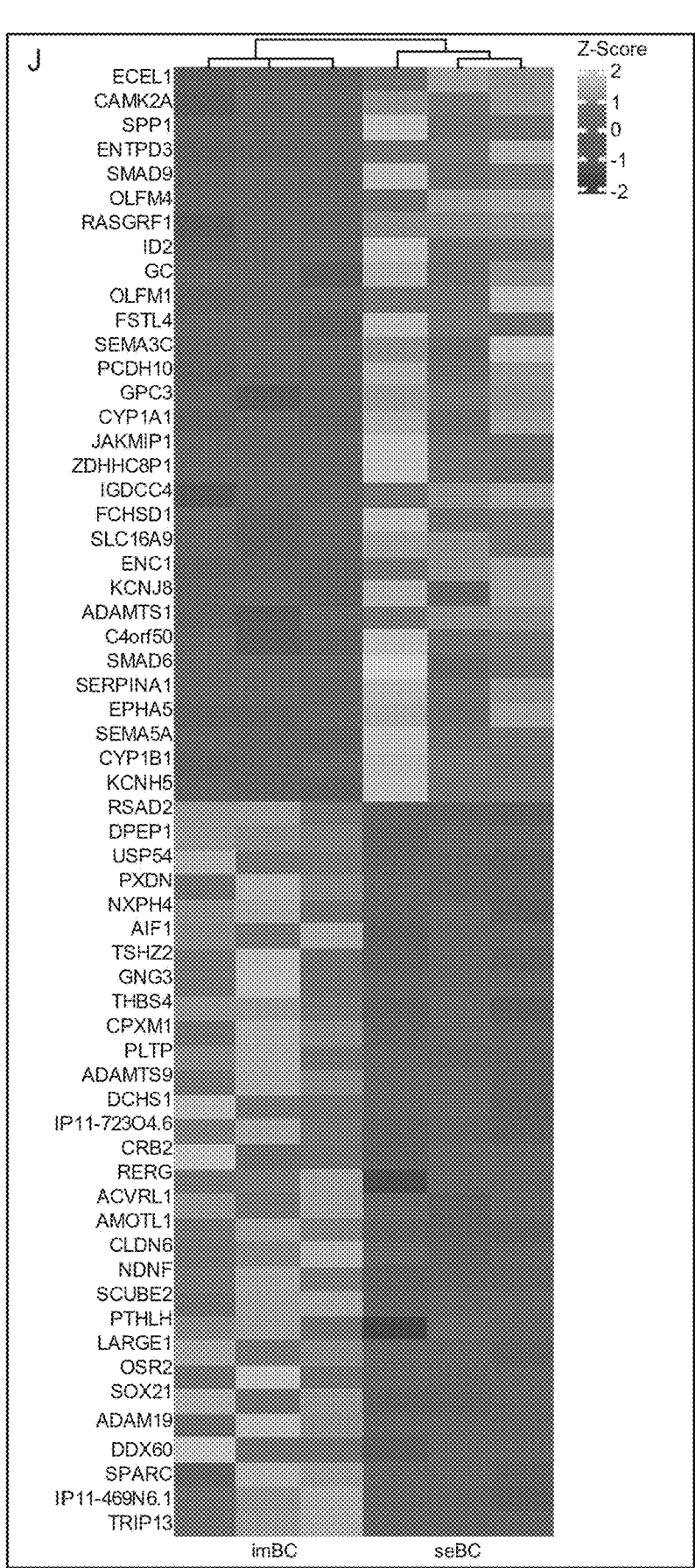
FIG. 1J, bulk RNA-seq analysis of pINSGFP+ sorted imBC versus seBC (un-curated, top 30 genes significantly up and down regulated) adjusted p-value <0.05 (n=3 independent differentiation experiments).
Figure 1K:
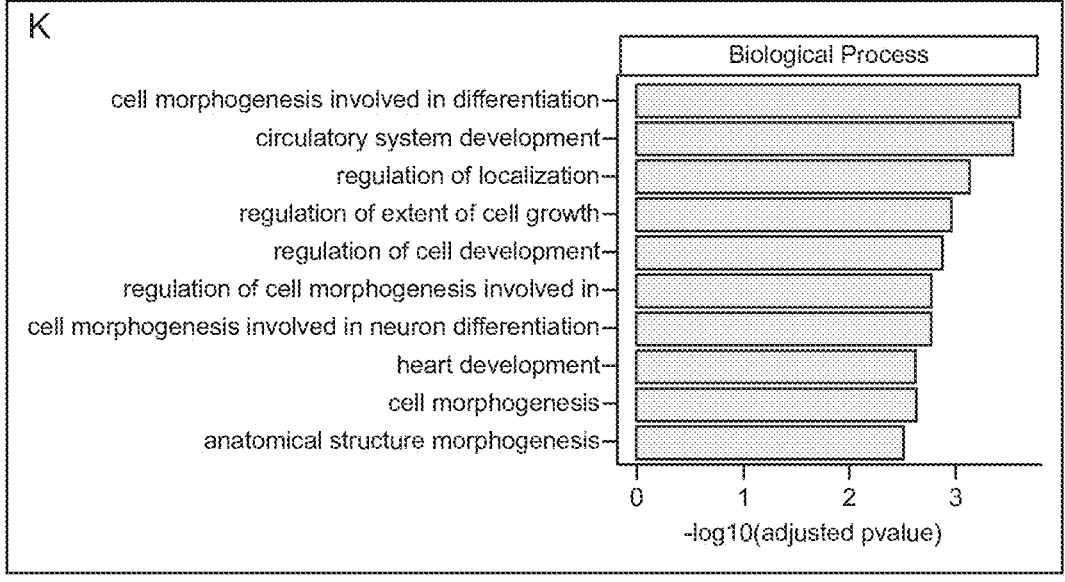
FIG. 1K, gene ontology of differentially regulated genes.
Figure 1L:
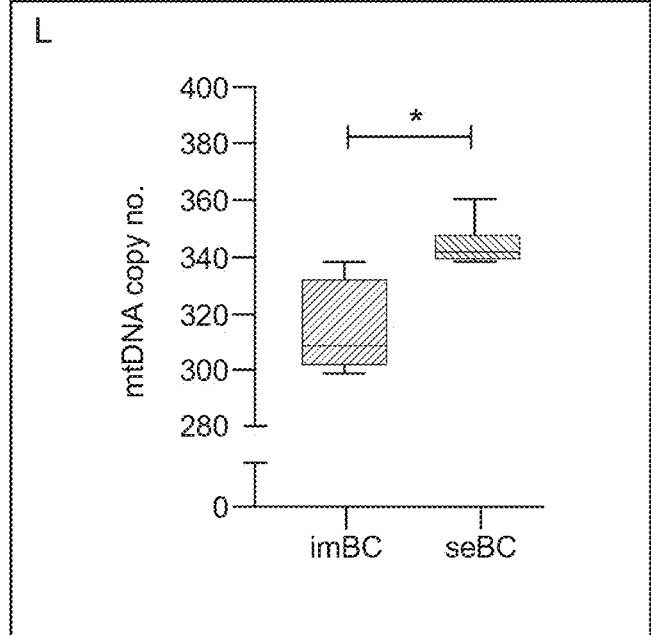
FIG. 1L, quantitative PCR analysis of mtDNA normalized to gDNA in pINSGFP+ sorted cells (n=3 independent differentiation experiments with 3×500 cells collected for analysis from each).

Using the pINSGFP reporter line, imBC and seBC were FAC sorted at day 23 and day 30, respectively (FIG. 1I), for global transcriptomic analysis. Overall, 158 and 53 genes were found to be significantly up- or down-regulated, respectively, in seBC compared to imBC (adjusted p-value <0.05) (FIG. 1J). However, in accordance with immunofluorescence analysis, seBC exhibited no differences in common markers of beta cell identity.

Gene Ontology (GO) analysis of differentially expressed genes indicated significant enrichment of genes associated with cell morphogenesis and differentiation in seBC (FIG. 1 K). Analysis of mtDNA in sorted imBC and seBC showed a significant increase in seBC (FIG. 1L) further supporting the observed increase in mitochondrial staining. Global levels of 5-hydroxymethylcytosine (5-hmc) has recently been suggested to increase with beta cell maturation; quantification of global 5-hmc in DNA isolated from sorted imBC and seBC by ELISA demonstrated a three-fold increase in the percentage of 5-hmc levels in seBC (FIG. 1M). Finally, aliquots of 1,000 pINSGFP+ cells from imBC and seBC were FAC sorted to quantify total insulin and proinsulin. seBC were found to contain twice as much insulin as imBC (FIG. 1N) and the proinsulin/insulin molar ratio was found to be significantly lower in seBC than imBC (FIG. 1O) indicating a profile of more mature insulin processing and storage in seBC. Taken together, these data demonstrate a more mature phenotype for self-enriched beta-like cells at the protein, RNA, DNA and mitochondrial level compared to imBC.

To more directly investigate the functional maturation state of seBC, dynamic glucose stimulated insulin secretion (dGSIS) assays were performed via islet perifusion. 20-30 clusters of imBC, seBC, or human islets were subjected to a sequence of different glucose concentrations (0.5 mM, 16.7 mM), 10 nM exendin-4, and 30 mM KCl challenges (FIG. 2A). As expected, human islets exhibited a characteristic first and second phase insulin secretion in response to a 16.7 mM glucose challenge that was efficiently diminished by subsequent exposure to 0.5 mM glucose. Membrane depolarization with 30 mM KCl resulted in a maximal secretion that was similar to the observed peak at first phase secretion in response to 16.7 mM glucose alone. imBC clusters exhibited minimal elevated insulin secretion in response to increased glucose levels and showed exaggerated insulin secretion in response to KCl membrane depolarization. In contrast, seBC displayed low insulin secretion at 0.5 mM glucose and a significant increase in secretion in response to stimulation with 16.7 mM glucose; with a typical first and second phase profile. seBC clusters efficiently and rapidly reduced insulin secretion upon return to 0.5 mM glucose levels and membrane depolarization resulted in insulin secretion comparable to the first phase peak, thus exhibiting a dGSIS profile similar to human islets. As with the sorted seBC cells analyzed in FIGS. 1A-10, seBC clusters recovered after dGSIS had higher insulin content than imBC clusters; while, human islets exhibited levels comparable to seBC (FIG. 2B). The fold change in insulin secretion from additional perifusion experiments was calculated (FIG. 2C—FIG. 2E); seBC and human islets showed a significant increase in insulin secretion in response to high glucose that was comparable to membrane depolarization with KCl, while imBC showed a significant increase in insulin secretion upon KCL exposure but not to high glucose.

Figure 2F:
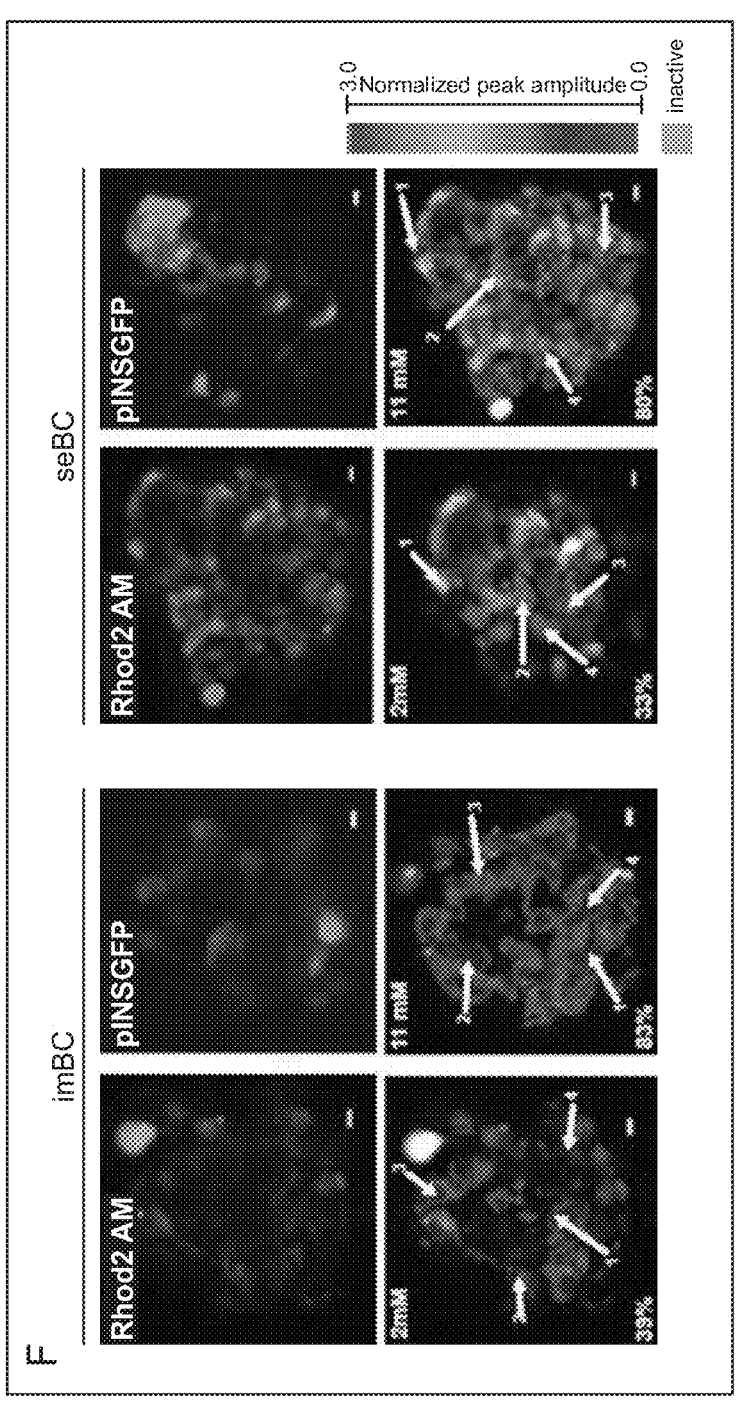
Figure 8B:
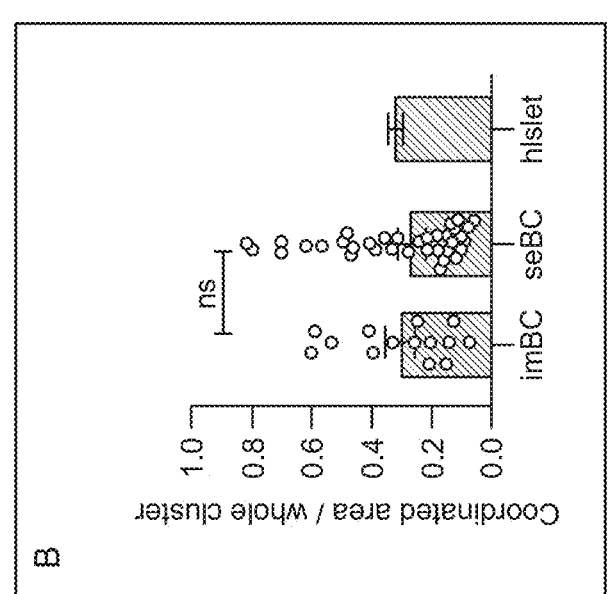
FIGS. 8A-8B show Ca$^{2+}$ analysis of imBC and seBC clusters.
Figure 8A:
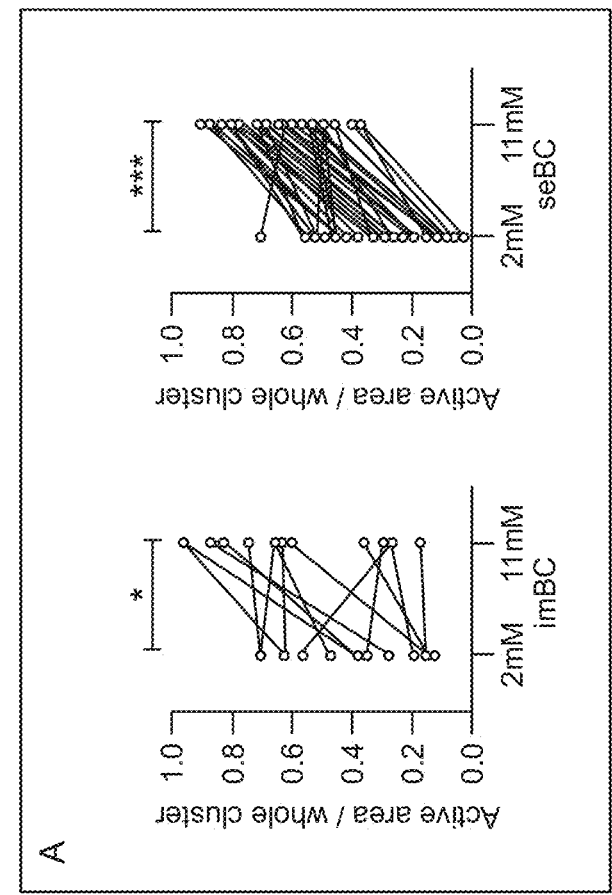

Highly sensitive $Ca^{2+}$ imaging has been used to accurately assay beta cell function from both mice and humans. Intact imBC and seBC clusters were incubated with Rhod2 AM calcium binding dye and then exposed to 2 mM and 11 mM glucose concentrations; uptake of $Ca^{2+}$ into individual cells was recorded by fluorescence imaging (FIG. 2F) and oscillations in $Ca^{2+}$ uptake quantified over time (FIG. 2G). Both imBC and seBC clusters were found to exhibit robust beta cell function, evidenced by a significant increase in the $Ca^{2+}$ active area upon exposure to elevated glucose (FIG. 2H-FIG. 2I & FIG. 8A). However, seBC displayed a significantly larger response compared to imBC. Interestingly, seBC clusters also present with significantly lower basal $Ca^{2+}$ active areas than imBC clusters indicating reduced insulin secretion; a feature specific to mature beta cells (FIG. 2H). Coordination of $Ca^{2+}$ dynamics of whole clusters was not changed between imBC and seBC, but was within the range of what has been previously reported for human islets (FIG. 8B).

These data demonstrate that sBC generated after approximately 3 weeks in vitro are immature, but self-enrich and mature during extended culture into seBC that are both phenotypically and functionally akin to cadaveric human islets.

Figures 3A, 3B:
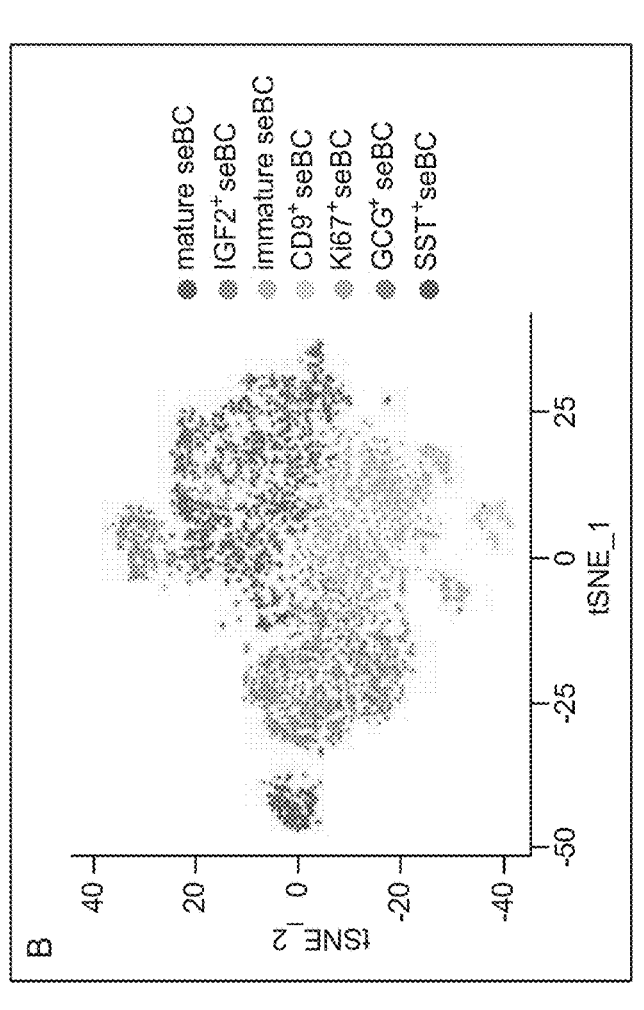
FIGS. 3A-3I present single cell RNA-seq profiling of beta cell differentiation identify distinct subpopulations and defines temporal dynamics of beta cell maturation.
Figure 3C:
Figure 3D:
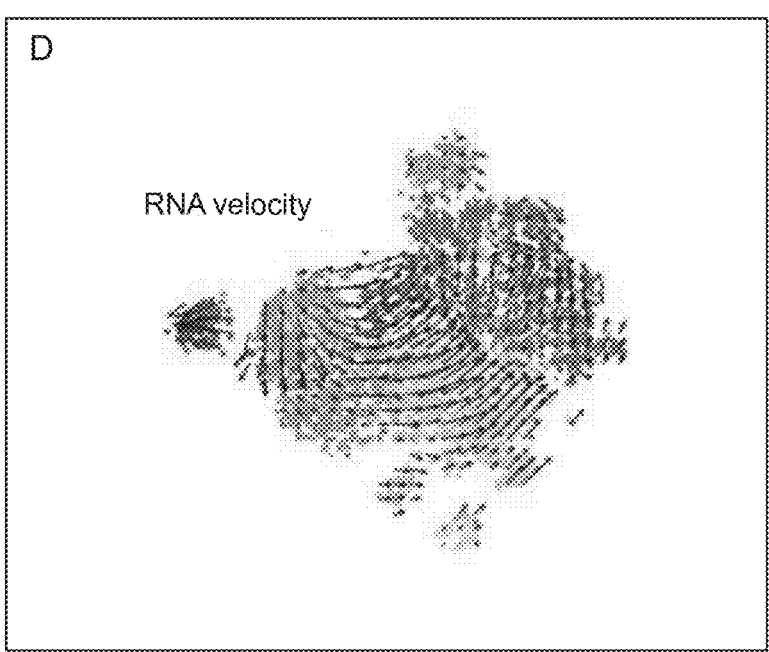
Figure 3E:
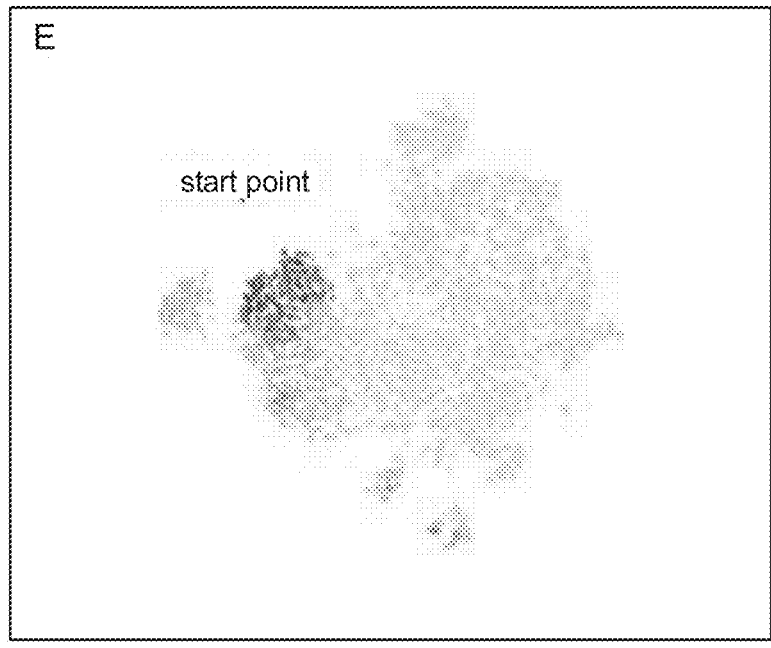
Figure 3F:
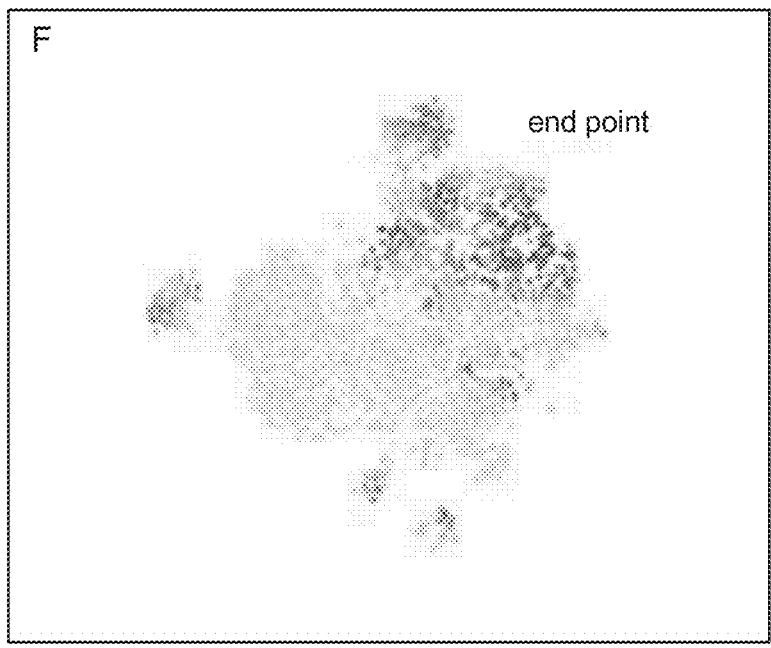
Figure 3G:
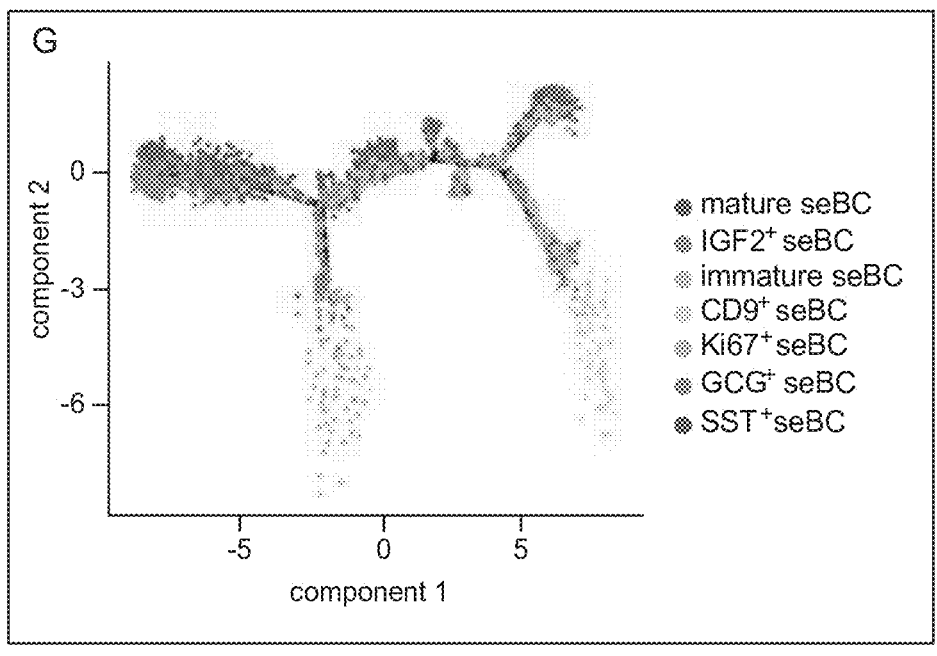
Figure 3H:
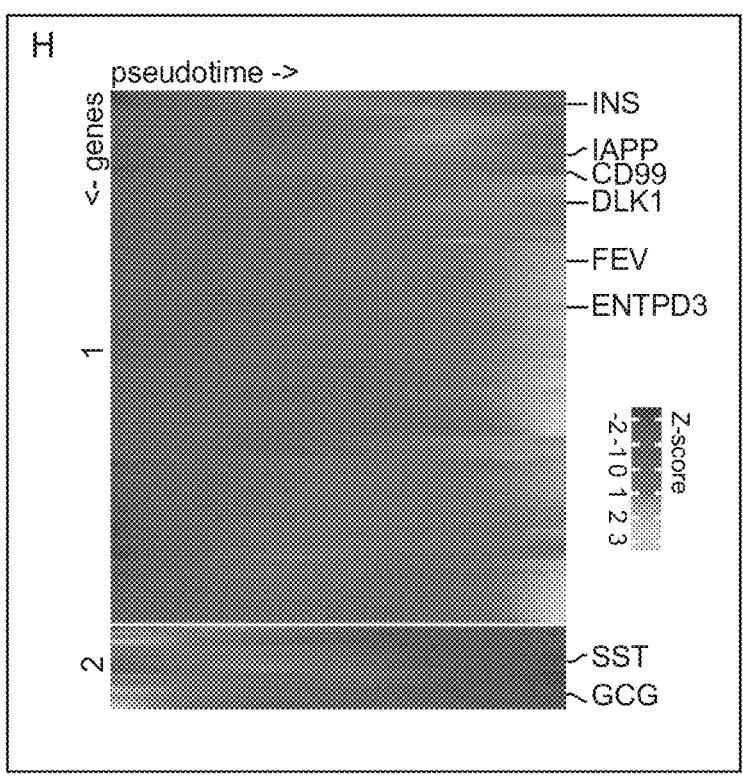
Figure 3I:
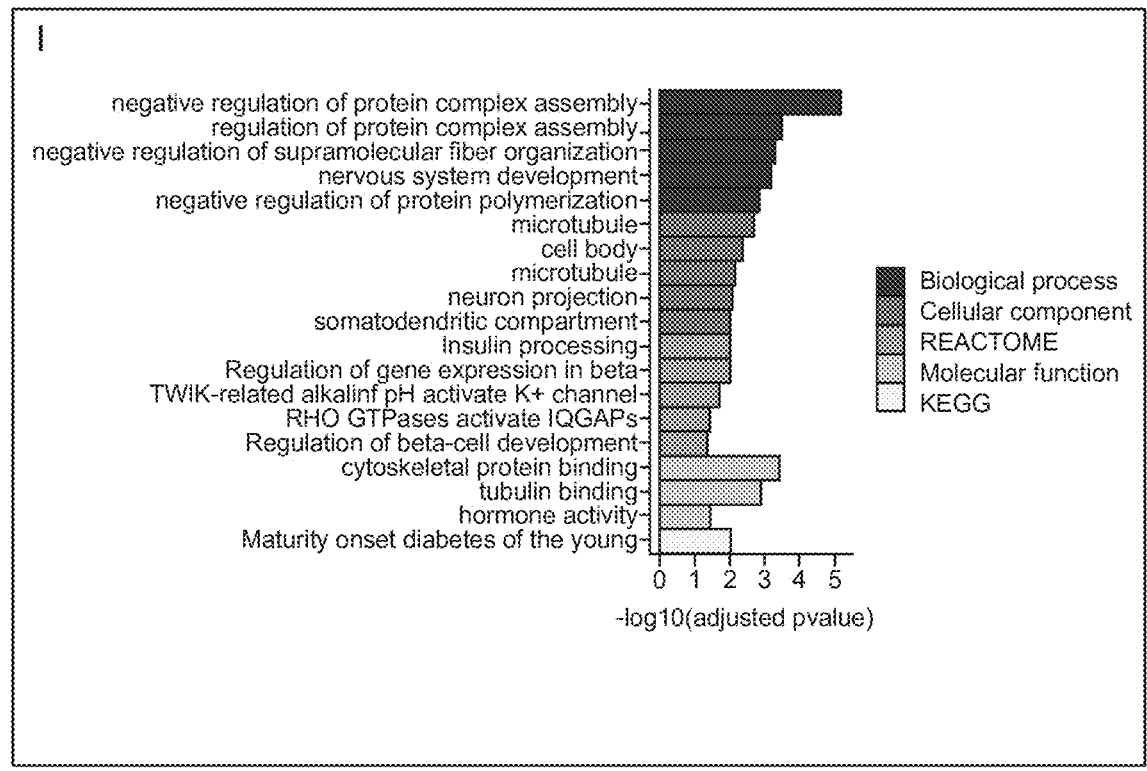

Example 2—Self-Enriched Beta-Like Cells are Heterogeneous and Comprise Subpopulations of Cells with Varying Maturity Expression Profiles To molecularly characterize this novel population of in vitro differentiated cells, pINSGFP+ seBC were FAC sorted and profiled via scRNA-seq using the 10× Genomics platform (FIG. 3A). A total of 4,143 cells were assigned to seven distinct subpopulations based on marker gene expression (FIG. 3B); seBC subpopulations were distinguished by INS and FEV expression, among other genes, into mature and immature subpopulations, respectively. Two polyhormonal subpopulations expressing transcripts for SST or GCG along with INS were identified. Expression of IGF2 or CD9 identified two additional subpopulations of seBC. Finally, a small proliferative (Ki67+) subpopulation was also found FIG. 3C, Supp. Table 1). RNA velocity analysis identified a differentiation trajectory from the immature subpopulations towards the most mature subpopulation of seBC (FIG. 3D), while Markov diffusion modeling of the RNA velocity allowed estimation of the probable differentiation start-point (FIG. 3E) as the polyhormonal and proliferative seBC subpopulations, and end-point (FIG. 3F) as the mature seBC subpopulation. Inferred trajectory of differentiation through the various subpopulations shows a drift from polyhormonal seBC towards mature seBC with two key branch points along the predicted trajectory (FIG. 3G). In depth analysis of the branch points and their gene expression demonstrates that the first branch point is primarily composed of the proliferative cell subpopulation (FIG. 9A). However, the second branch is enriched for cells from the immature seBC FEV+ and CD9+ beta cell subpopulations, suggesting that the CD9+ beta cell subpopulation may be generated through a trajectory distinct from the dominant mature seBC population (FIG. 9 B). Analysis of gene expression dynamics across pseudotime demonstrated increasing expression of INS, IAPP, and LMO1 along the differentiation axis, concomitant with decreasing expression of SST, GCG, APOA1/C3, known markers of the less differentiated polyhormonal subpopulations (FIG. 3H). Finally, GO analysis of the mature seBC population revealed significant enrichment of genes associated with insulin processing, beta cell development, hormone activity and K+ channel activity; further strengthening the identity of the subpopulation.

Figure 10A:
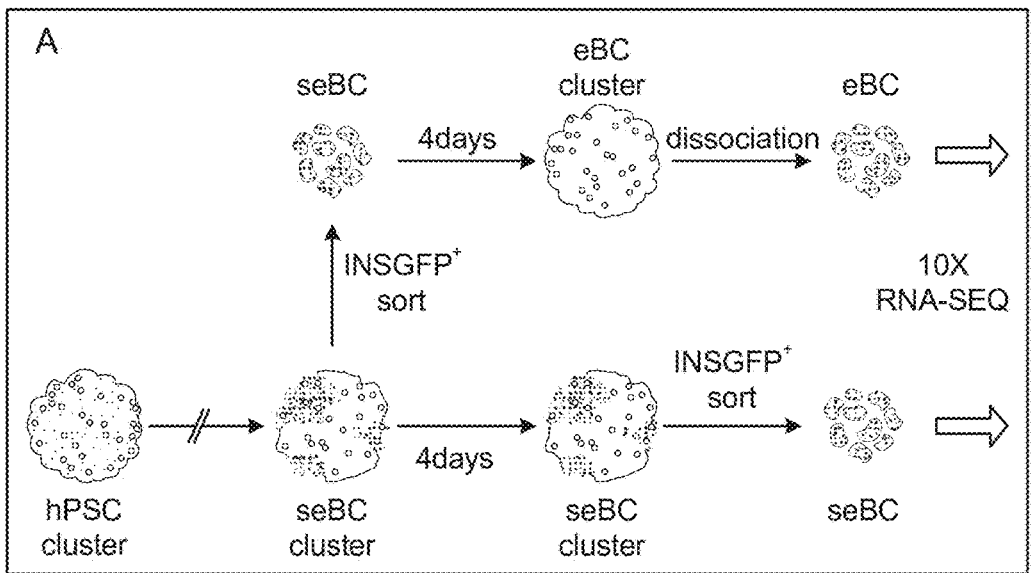
FIGS. 10A-10I. Single cell RNA-seq profiling of eBC differentiation.
Figure 10:
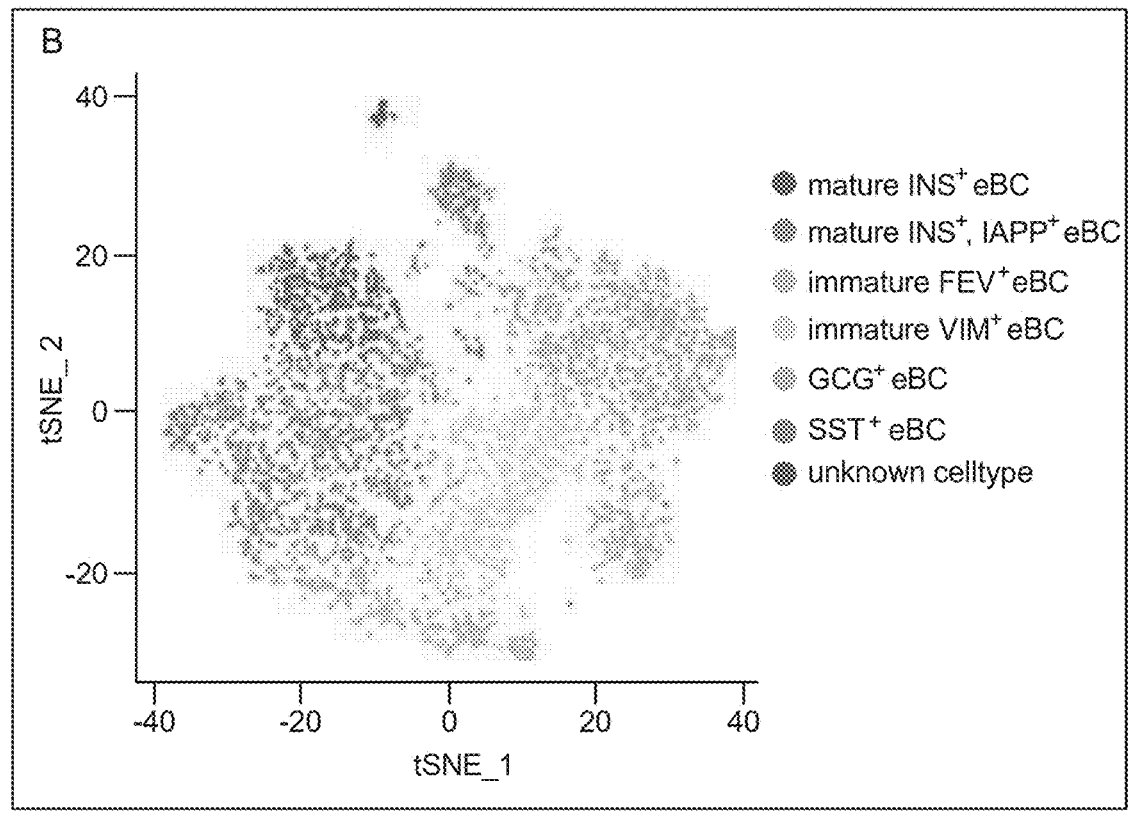
Figure 10C:
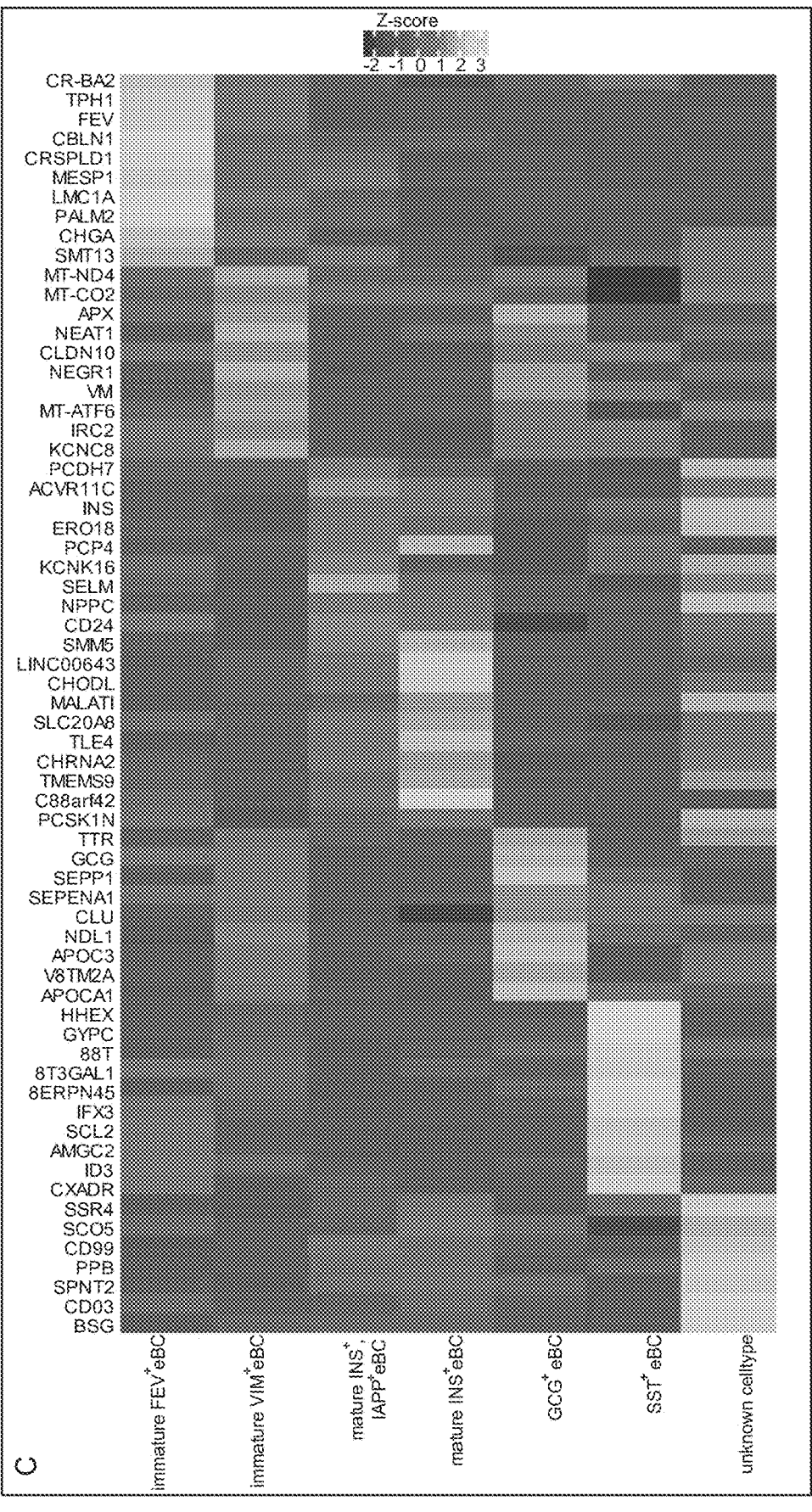
Figure 10D:
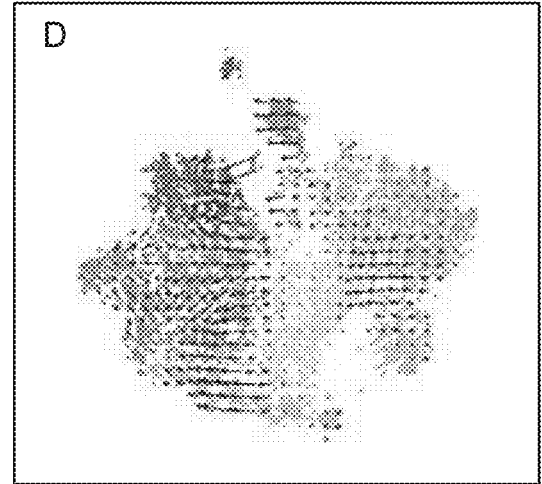
Figure 10E:
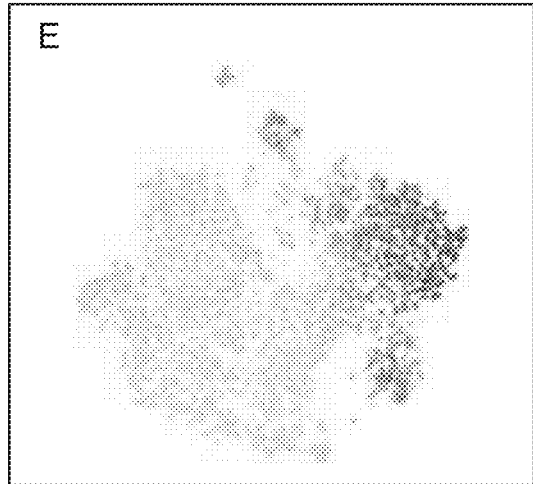
Figure 10F:
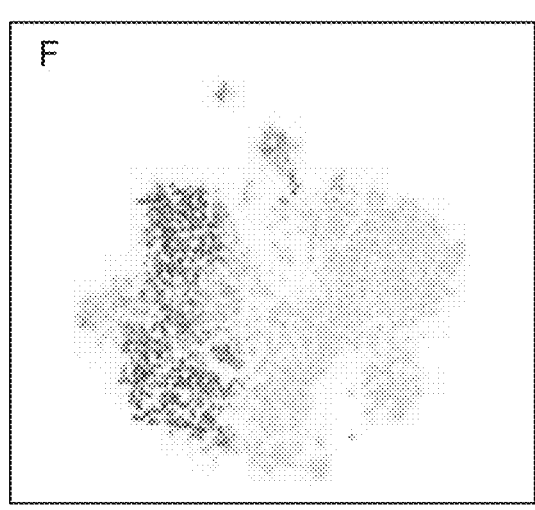
Figure 10I:
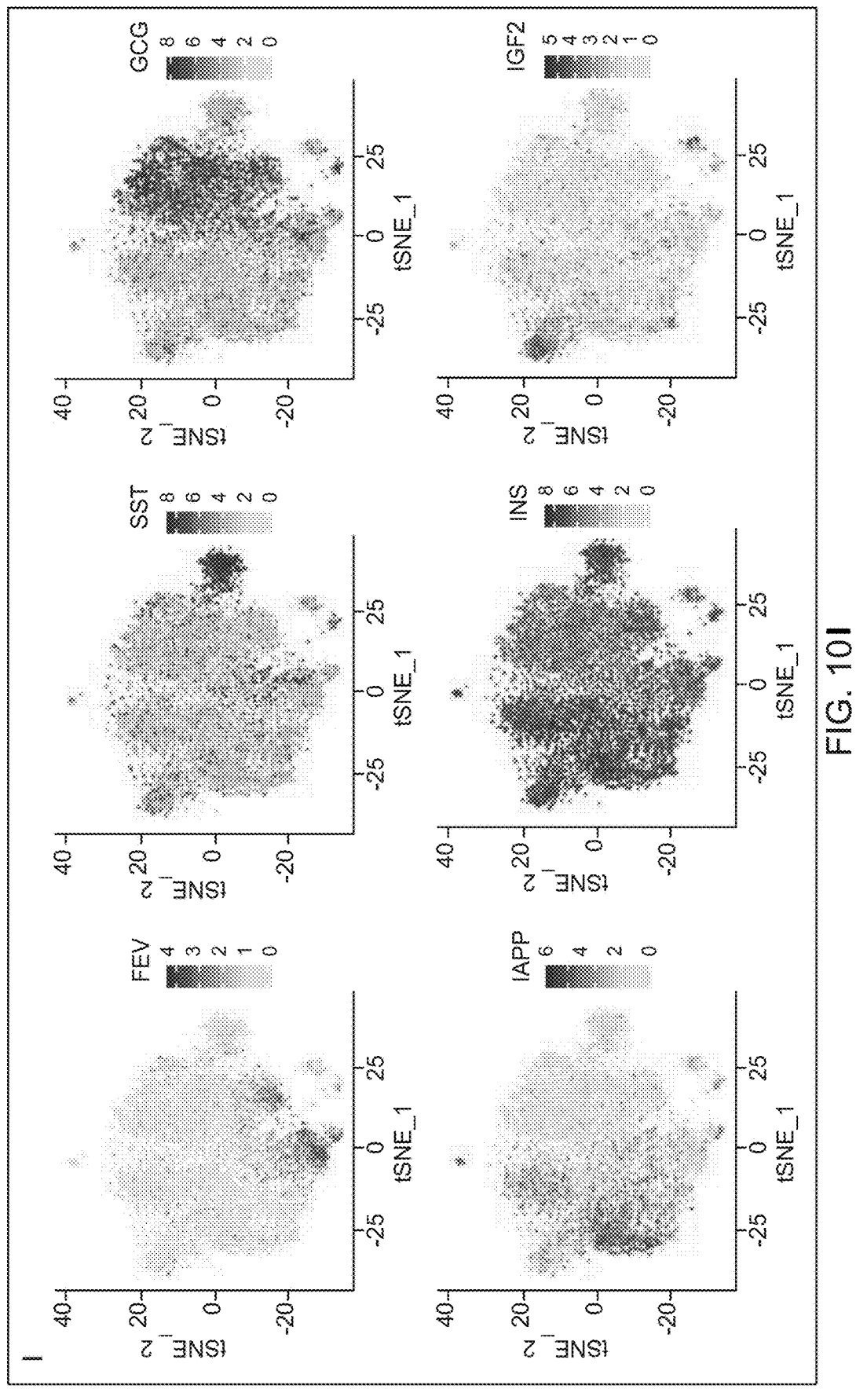

Artificial re-aggregation of quasi-pure, FAC sorted imBC into enhanced beta-like cell (eBC) clusters results in improved maturation. To compare eBC and seBC, sBC sorted and reaggregated for 4 days were profiled by scRNA-seq (FIG. 10A). 4,178 cells were assigned to seven different subpopulations based on marker gene expression (FIG. 10B and FIG. 10C). RNA velocity analysis identified a trajectory from immature polyhormonal subpopulations to the most mature beta cell populations, similar to the trajectory observed in the seBC (FIG. 10D-FIG. 10G). Alignment of the seBC and eBC scRNA-seq datasets into the same tSNE projection revealed that similar subpopulations are generated by both protocols, with the exception of a minor unknown cell population found in the eBC dataset (FIG. 10H and FIG. 10I). Taken together, these data indicate that phenotypically and functionally mature seBC, present as distinct subpopulations with different maturation levels. Our analysis further suggests that under the culture conditions employed seBC exhibit a trajectory towards the most mature subpopulation.

Figures 4A, 4B:
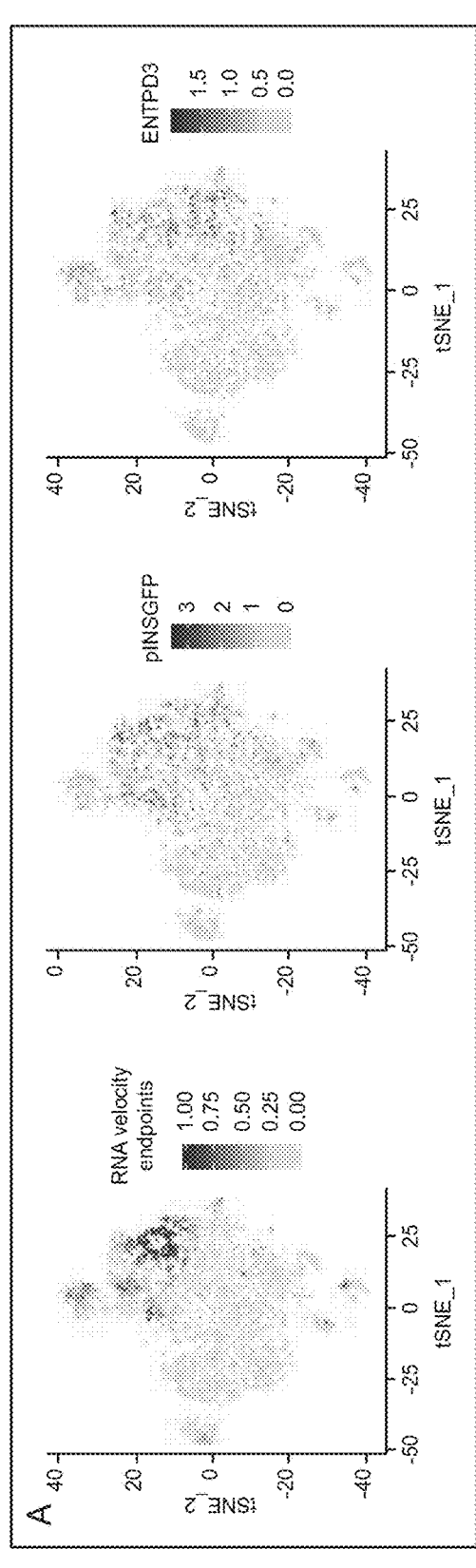
FIGS. 4A-4N present data showing that Ectonucleoside Triphosphate Diphosphohydrolase 3 marks mature beta-like cells.
FIG. 4B is relative ENTPD3 gene expression in pINSGFP+ imBC and seBC (n=3 independent differentiation experiments).
Figure 4C:
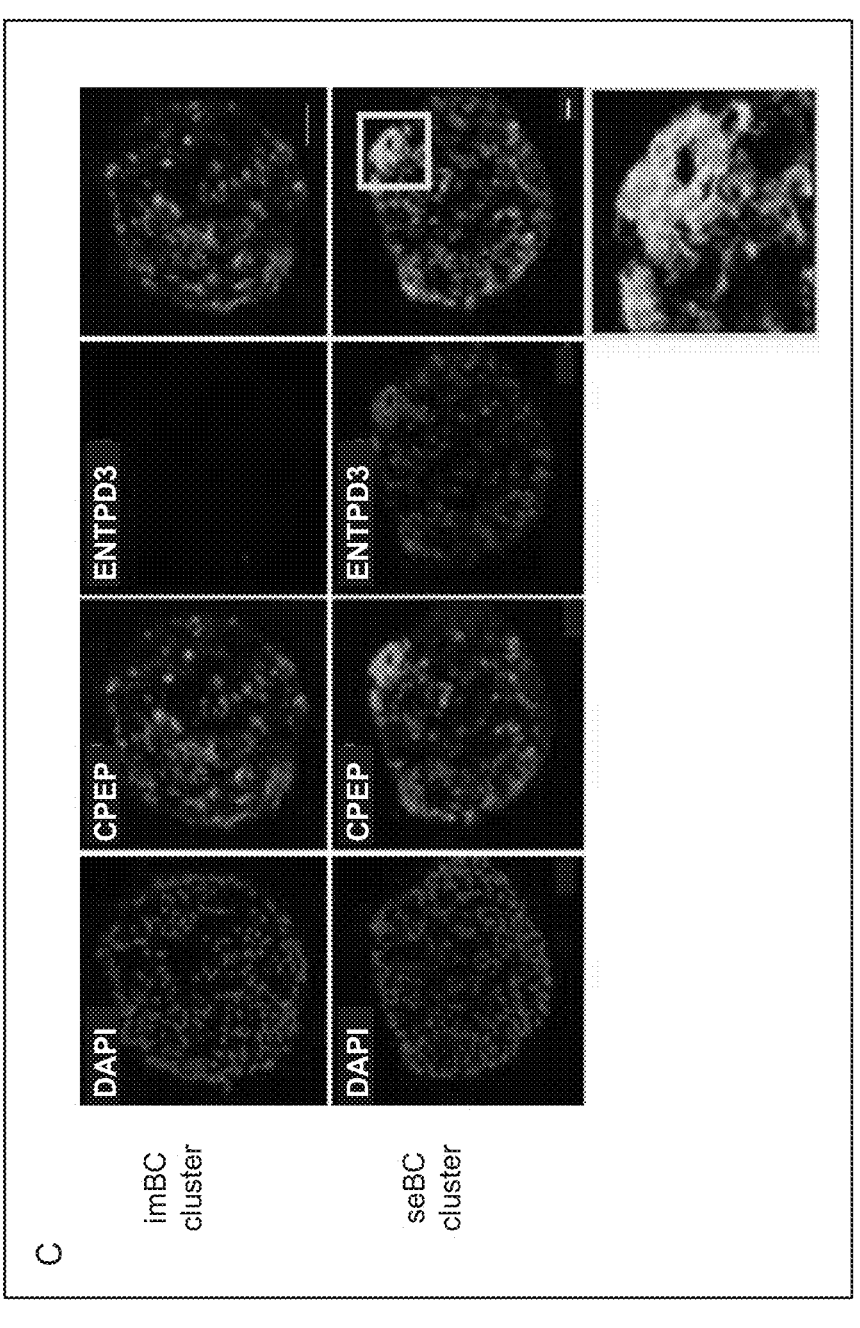
FIG. 4C, immunofluorescence staining for c-peptide (CPEP; a byproduct of processing of endogenous insulin, INS, Gene ID: 3630) and ENTPD3 in sections of imBC and seBC clusters (scale bar represents 20 μm).
Figure 4D:
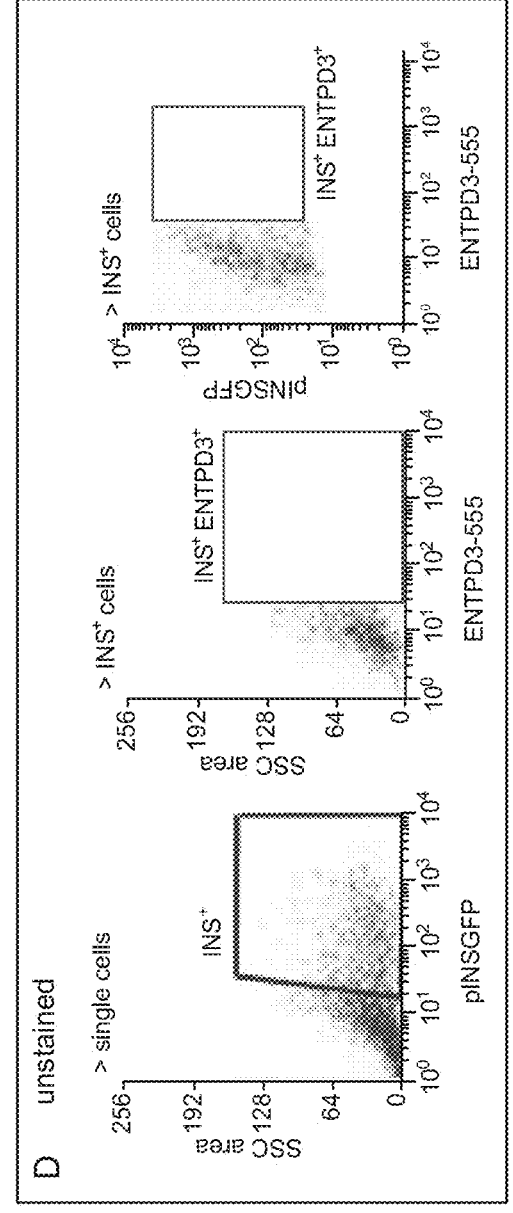
FIG. 4D & FIG. 4E, representative sorting gates for pINSGFP+ENTPD3+/- cells in unstained negative control cells, (FIG. 4D) and with direct conjugated ENTPD3 antibody (FIG. 4E).
Figure 4E:
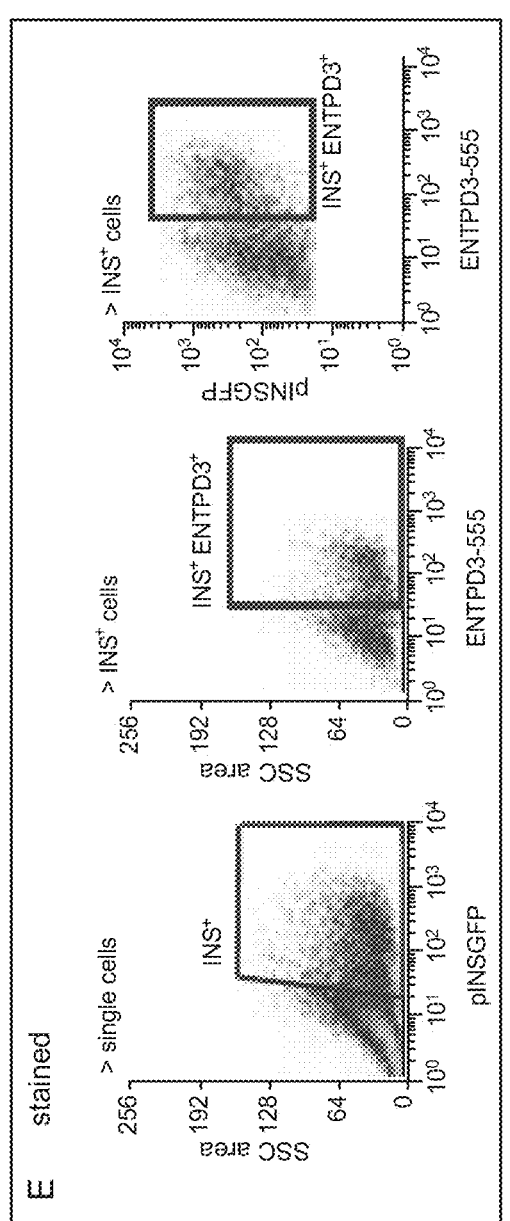
Figure 4F:
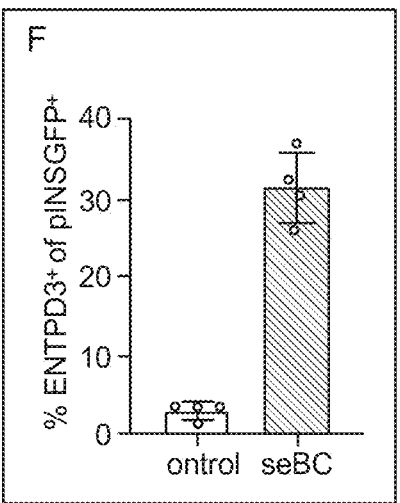
FIG. 4F, quantification of the percentage of ENTPD3+ cells within total pINSGFP+ population by FACS (n=4 independent differentiation experiments).
Figure 4G:
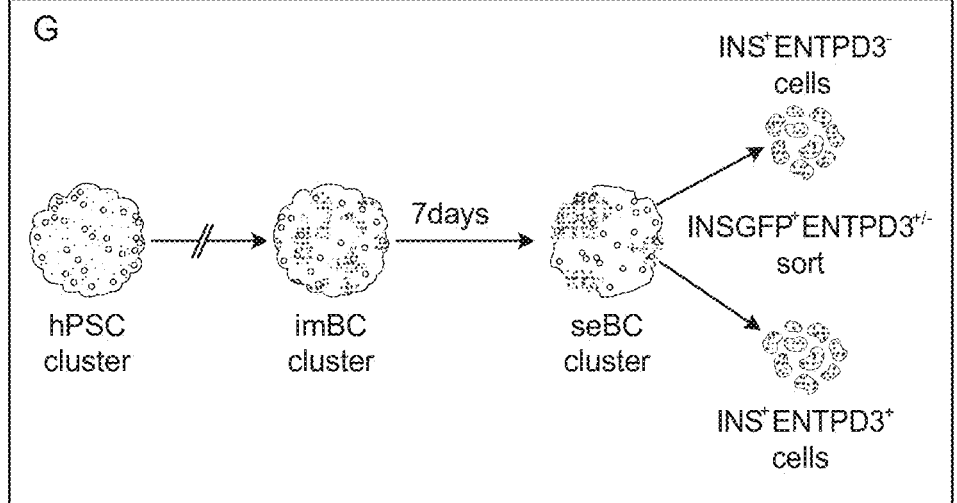
FIG. 4G, schematic representation of pINSGFP+ENTPD3+/- sorting from seBC.
Figure 4H:
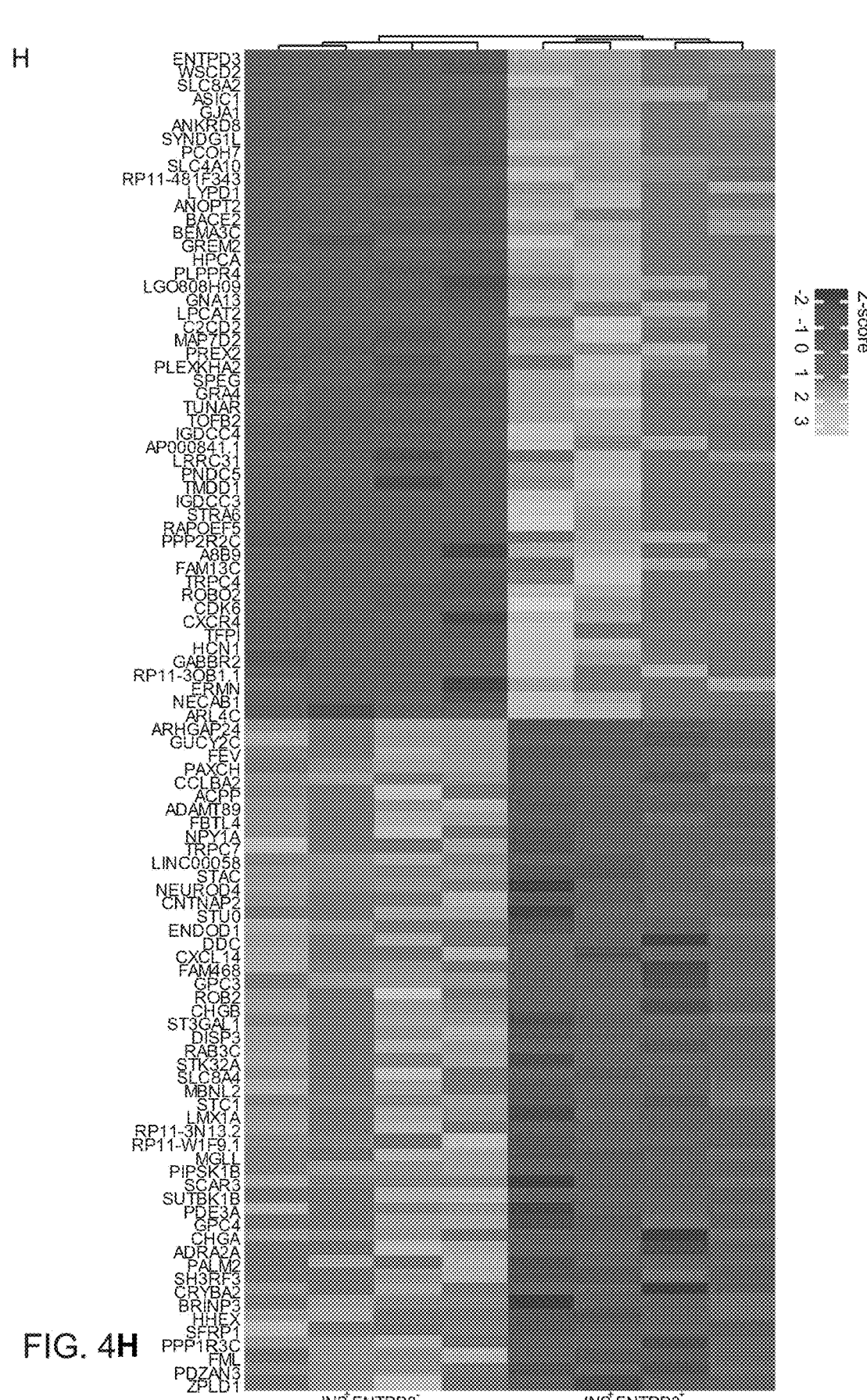
FIG. 4H, bulk RNA-seq analysis of INS+ENTPD3+ vs INS+ ENTPD3- cells sorted from seBC clusters (un-curated list of top 30 genes significantly up and down regulated as per adjusted p-value <0.05, n=4 independent differentiation experiments).
Figure 41:
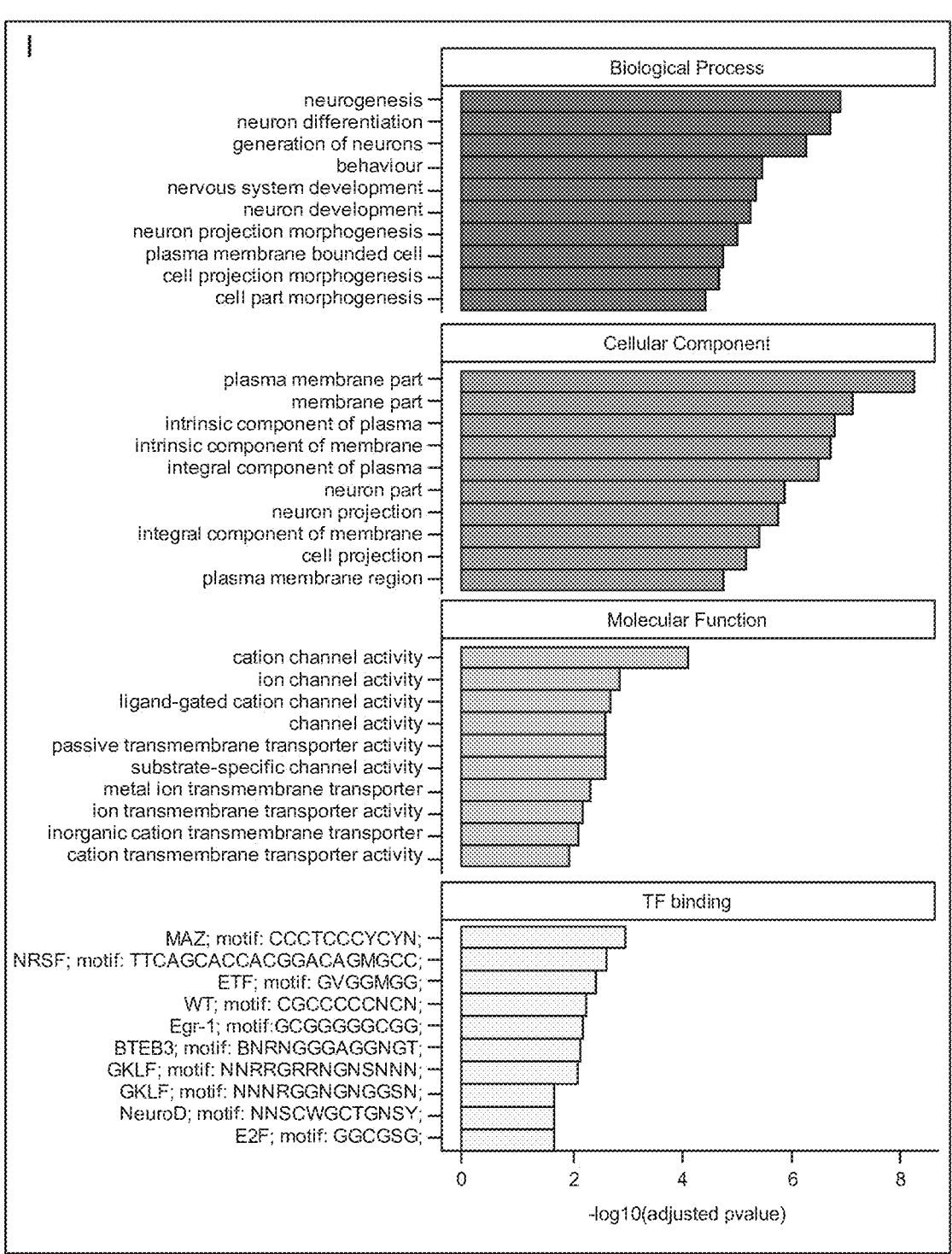
Figure 4J:
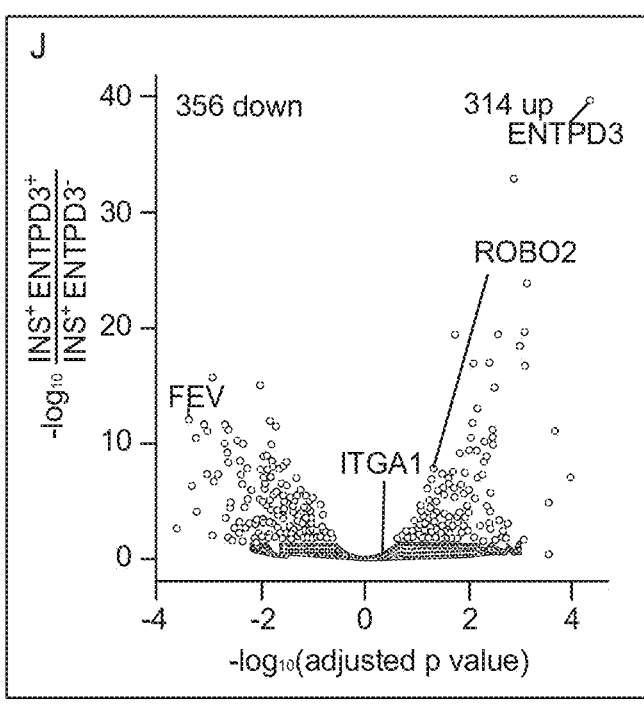
FIG. 4J. volcano plot of differential expression (DE) analysis of INS+ENTPD3+ vs INS+ENTPD3-.
Figure 4K:
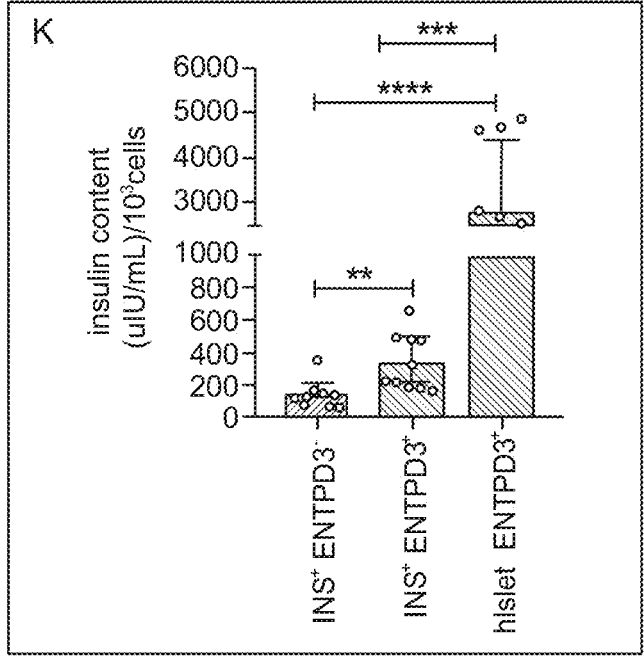
FIG. 4K, insulin content per 1,000 INS+ENTPD3+/- sorted cells from seBC and human islets (n=3 independent differentiation experiments or human islets preps, with 3×1,000 cells analyzed per experiment).
Figure 4N:
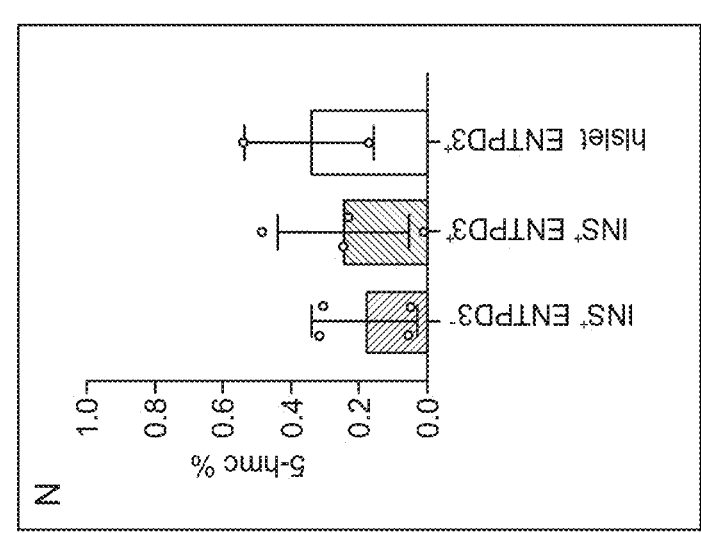

Example 3—Ectonucleoside Triphosphate Diphosphohydrolase 3 Marks Most Mature Beta-Like Cells Detailed analysis of the most mature seBC subpopulation revealed significant enrichment of the cell-surface marker ectonucleoside triphosphate diphosphohydrolase 3 (ENTPD3) recently described as a marker of mature human beta cells in vivo (FIG. 4A). ENTPD3 transcripts are significantly increased in seBC compared to imBC and while undetectable at the protein level in imBC, ENTPD3 is readily expressed in CPEP+ cells within seBC clusters; strongly marking CPEP+ caps (FIG. 4 B and FIG. 4C). While pINSGFP based cell sorting allows for collection of all seBC, addition of an ENTPD3 specific antibody directly conjugated to Alexa Fluor-555 allows the specific isolation of a most mature INS+ENTPD3+ seBC subpopulation, equaling around 30% of the total pINSGFP+ seBC population (FIG. 4D—FIG. 4F and FIG. 10A-FIG. 10B). For in-depth analysis, seBC were sorted into 'mature' INS+ENTPD3+ and 'immature' INS+ENTPD3− seBC subpopulations (FIG. 4G). Differential analysis of RNA collected for bulk RNA sequencing allowed compilation and identification of novel maturation-associated genes showing up- and down-regulation (FIG. 4H-FIG. 4J). GO analysis of differentially expressed genes revealed significant enrichment for genes encoding cell membrane proteins, in particular those involved in ion channel activity in mature INS+ENTPD3+ seBC (FIG. 4I).

Figure 4M:
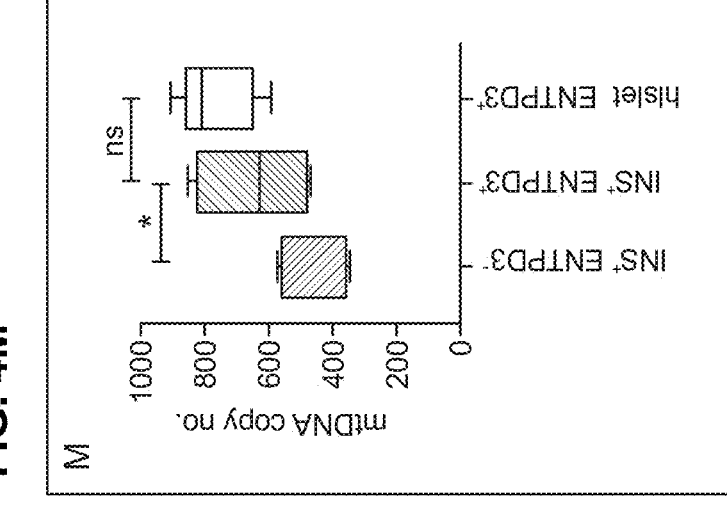
FIG. 4M, quantitative PCR analysis of mtDNA normalized to gDNA in INS+ENTPD3+vs INS+ENTPD3- sorted cells from seBC and human islets n=3 independent differentiation experiments or human islets preps, with 3×500 cells analyzed per experiment).
Figure 4L:
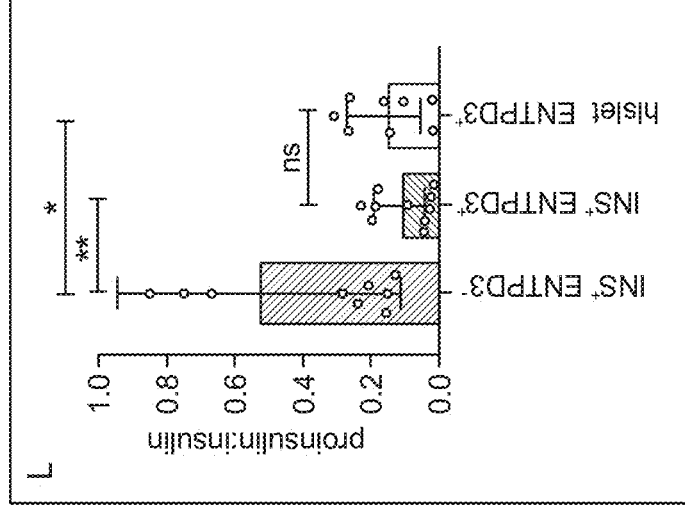
FIG. 4L, proinsulin to insulin content ratio of INS+ENTPD3+/- sorted cells from seBC and human islets (n=3 independent differentiation experiments or human islets preps, with 3×1,000 cells analyzed per experiment).

To further characterize INS+ENTPD3+ and INS+EN-TPD3− seBC, 1,000 cells from each subpopulation were FAC sorted and analyzed by ELISA for insulin and proinsulin content. To allow direct comparison to human beta cells, ENTPD3+ cells from human islet preps, were sorted to an average purity of 90% insulin expressing cells (FIGS. 12A-12G). INS+ENTPD3+ seBC have significantly higher insulin content than INS+ENTPD3− cells (FIG. 4K), however, levels are lower when compared to FAC sorted, ENTPD3+ cadaveric beta cells. The proinsulin to insulin molar ratio of INS+ENTPD3− cells is significantly higher compared to INS+ENTPD3+ suggesting more efficient insulin bioprocessing in the INS+ENTPD3+ seBC subpopulation (FIG. 4L). The observed proinsulin to insulin ratio of INS+ENTPD3+ seBC is comparable to ENTPD3+ cadaveric beta cells further strengthening the idea that INS+ENTPD3+ seBC represent a mature beta cell subpopulation. mtDNA copy number is also significantly increased in INS+ENTPD3+ seBC compared to immature seBCs and within the range of hIslet ENTPD3+ cells (FIG. 4M). No significant difference was detected in global 5-hmc levels across the three cell types.

Figure 5C:
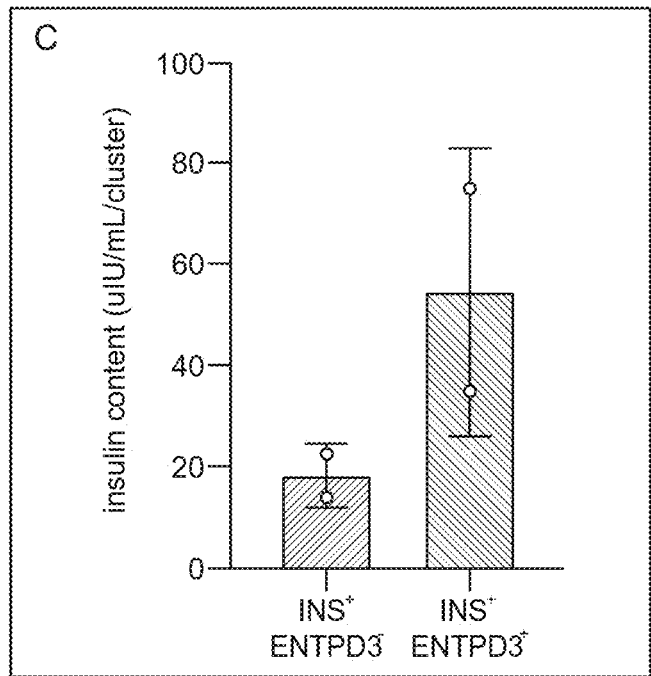
Figure 5D:
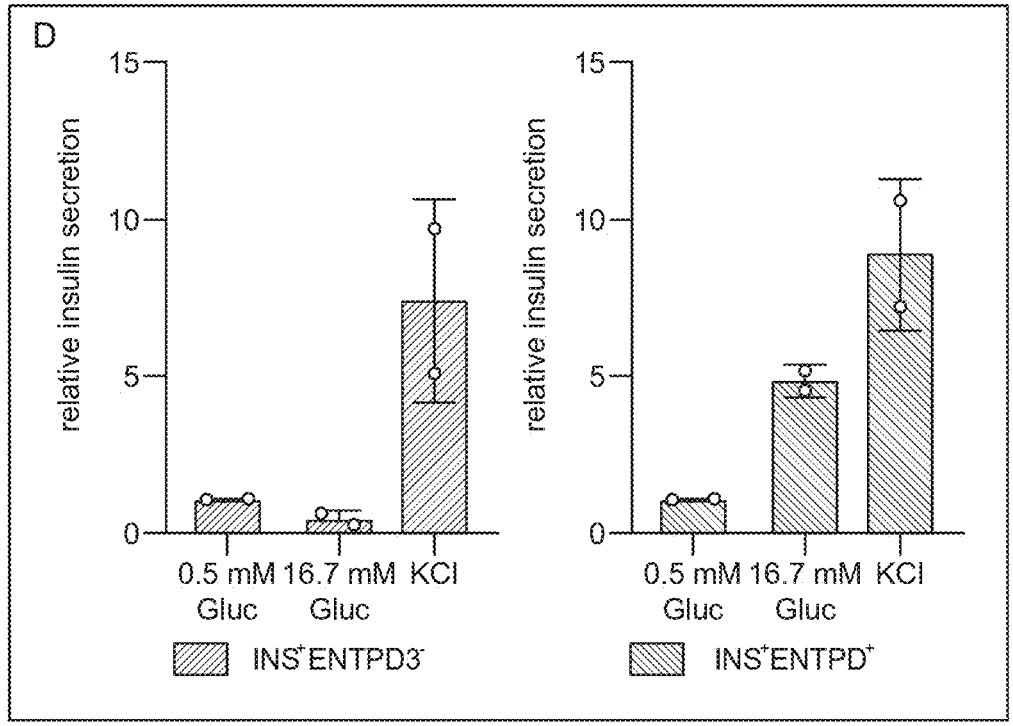
Figure 13A:
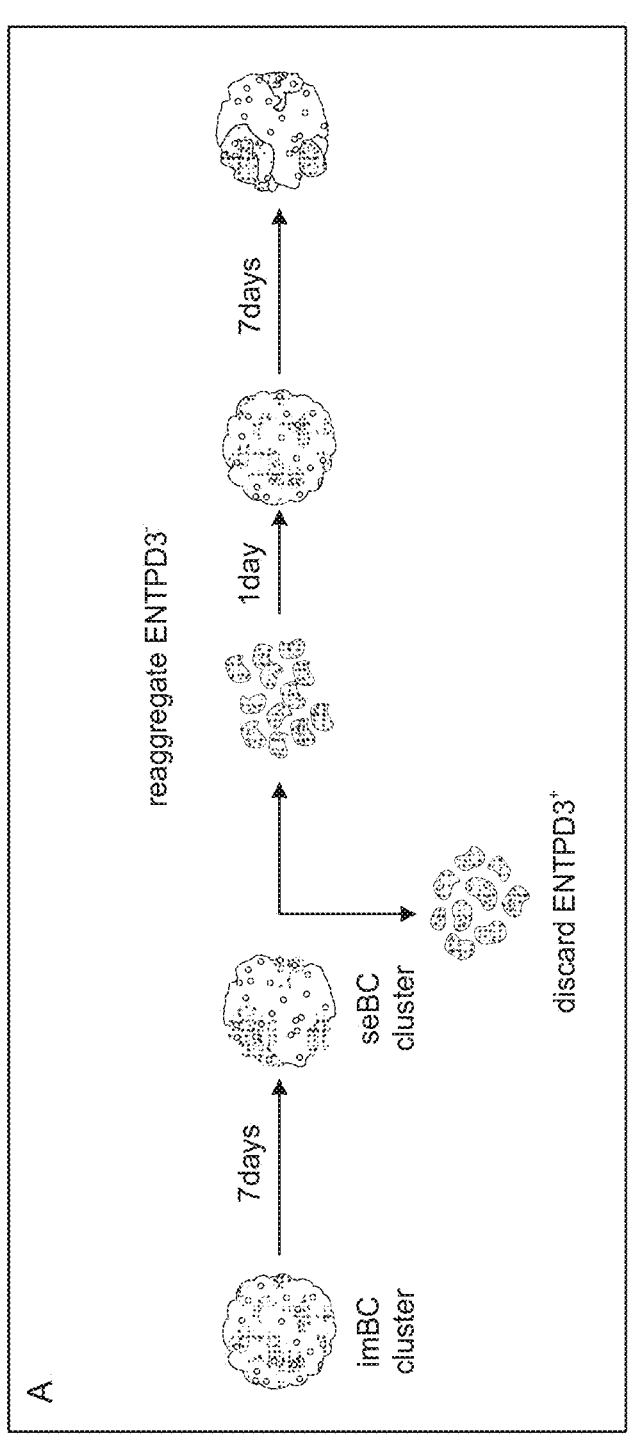
Figure 14A:
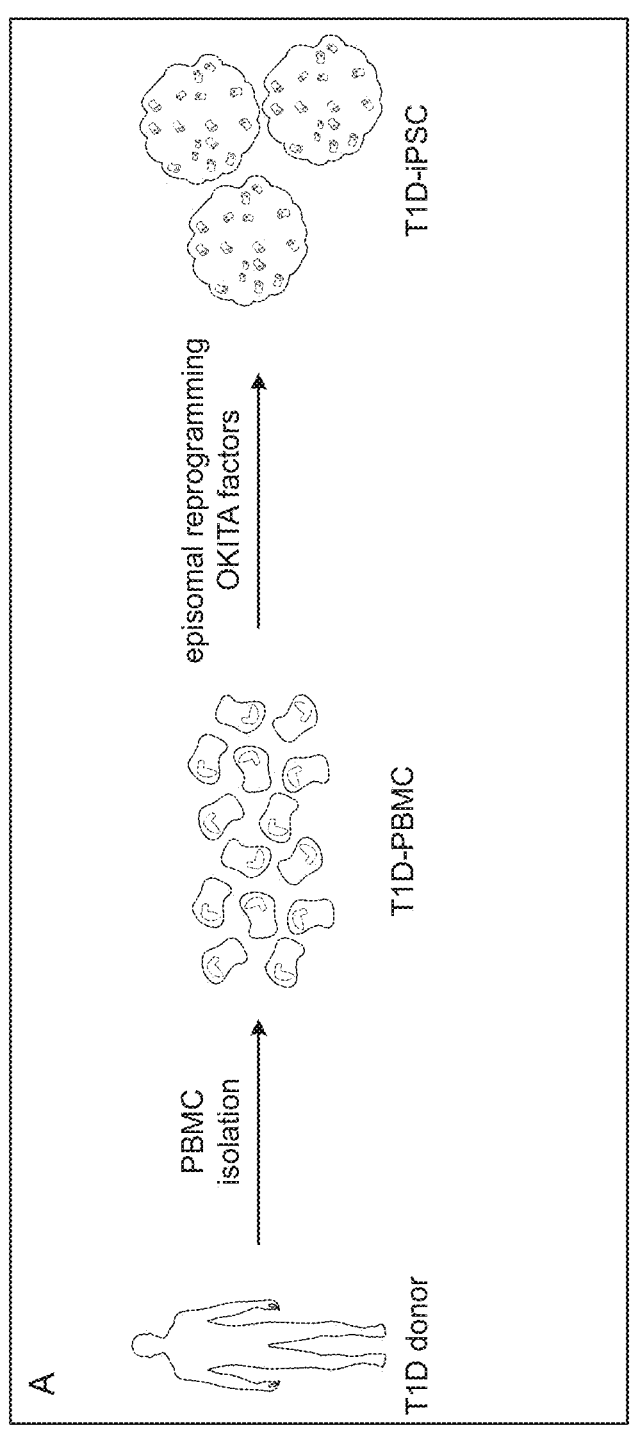
Figure 14C:
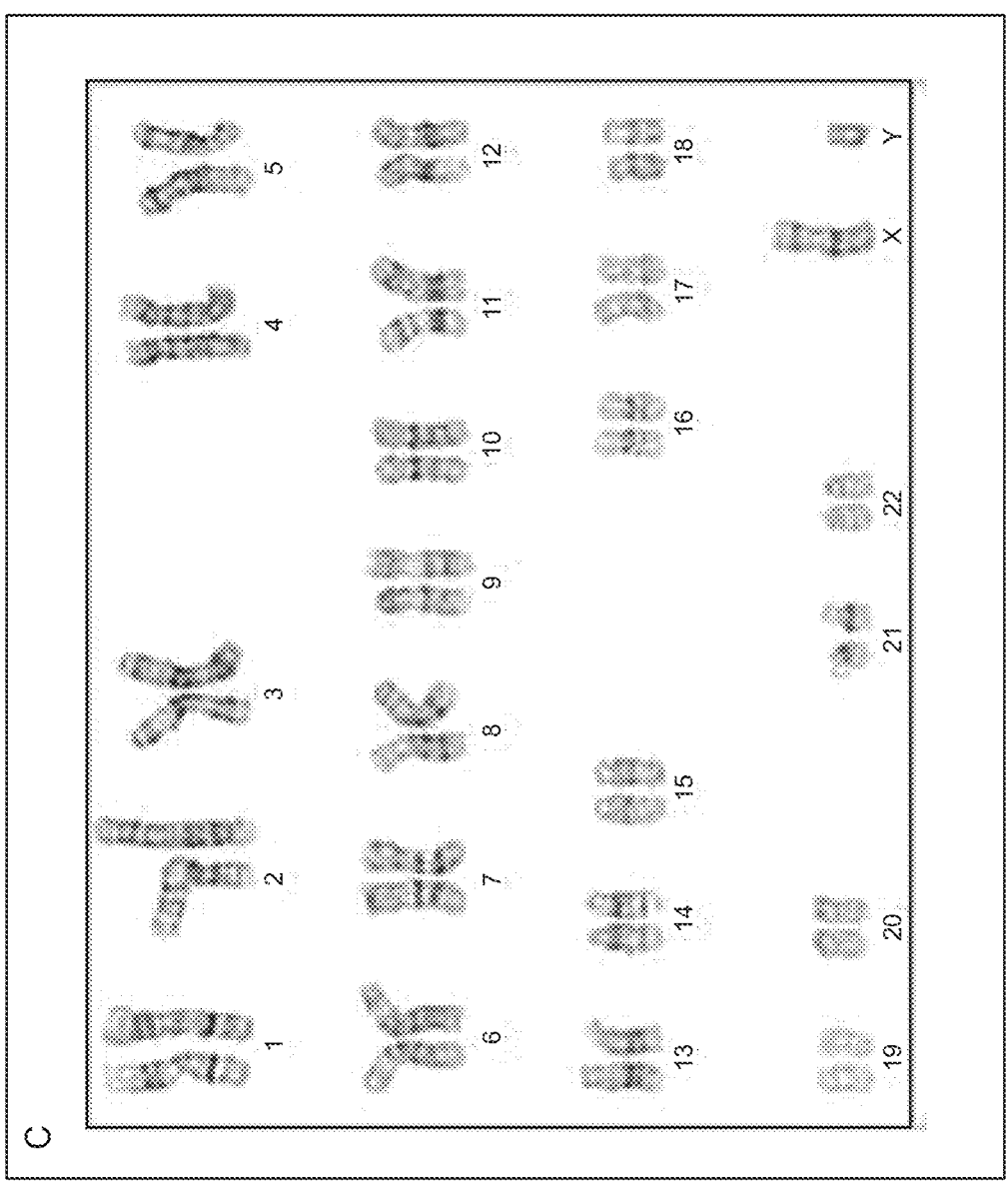
Figures 14D, 14E:
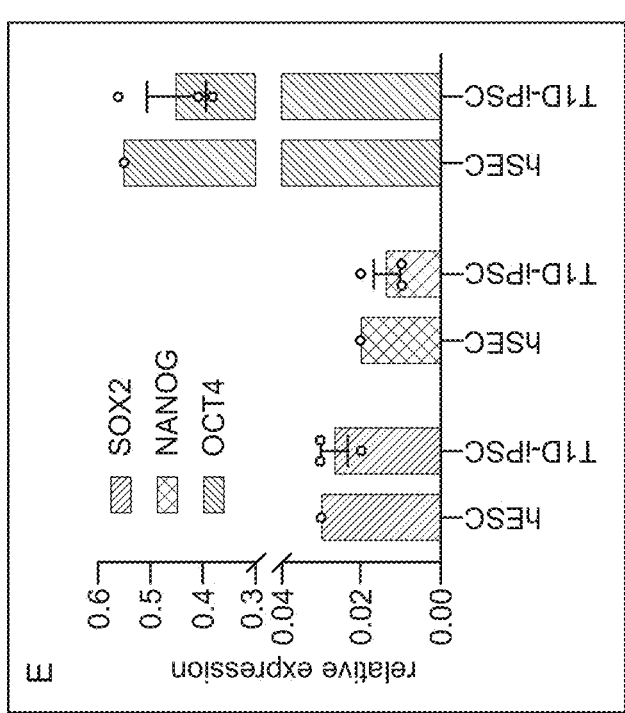
Figure 14F:
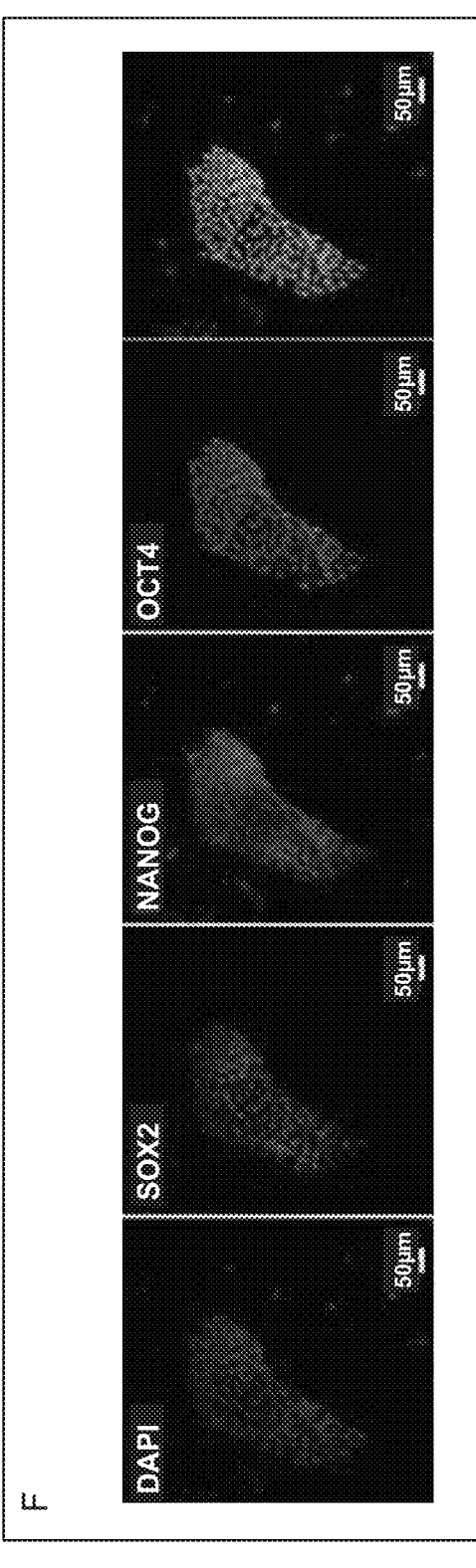
Figure 15A:
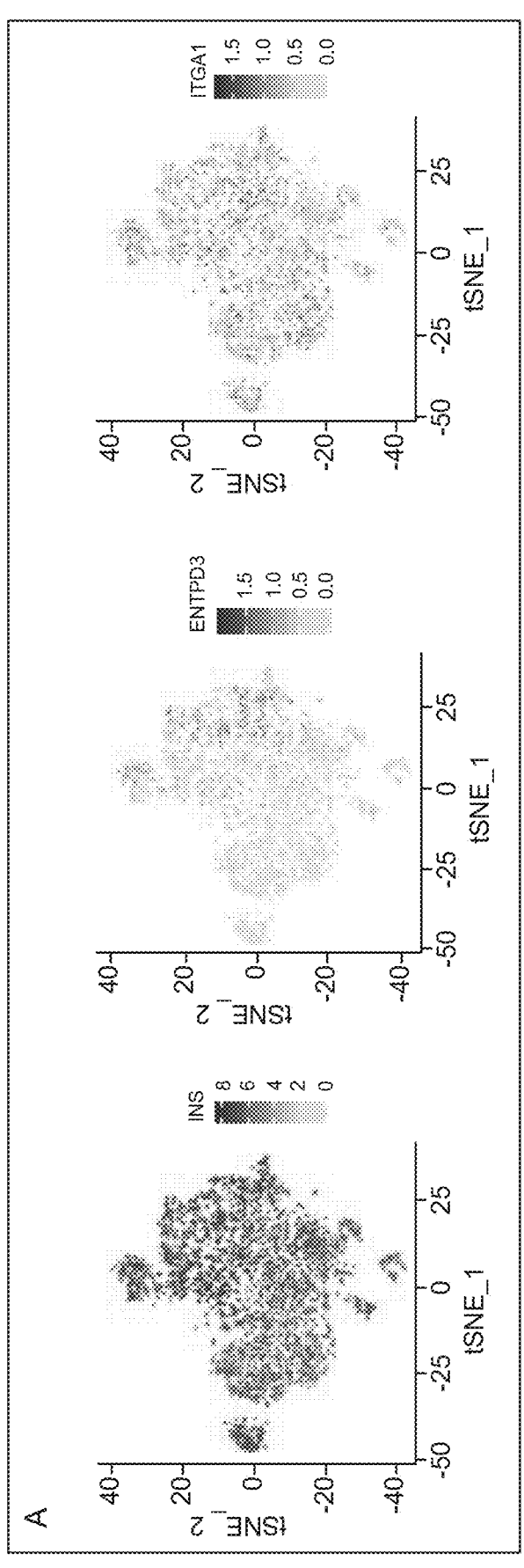

To test the functionality of INS+ENTPD3+ seBC directly, immature INS+ENTPD3− and mature INS+ENTPD3+ cells were sorted and reaggregated in the presence of endothelial and mesenchymal support cells for 48 h followed by dGSIS assay (FIG. 5A). Of note, we found that reaggregated INS+ENTPD3− clusters started to co-express the maturation marker ENTPD3 after longer culture periods, indicating that seBC maturation is a dynamic and potentially continuous process within differentiation cultures (FIGS. 13A-13B). This observation prevented functional analysis of clusters cultured for longer periods of time and necessitated the use of support cells to stabilize clusters. Reaggregated immature INS+ENTPD3− clusters were found to be non-glucose responsive but responded to membrane depolarization with KCl (FIG. 5B and FIG. 5D). In contrast, mature INS+ENTPD3+ clusters readily responded to 16.7 mM glucose, exendin-4, and KCl, and regulated insulin secretion dynamically (FIG. 5B and FIG. 5D). Clusters from each condition were recovered after dGSIS and tested for total insulin content; mature INS+ENTPD3+ clusters were found to contain more insulin than the immature clusters (FIG. 5C), consistent with data described above (FIGS. 4A-4N).

Figures 5E, 5F:
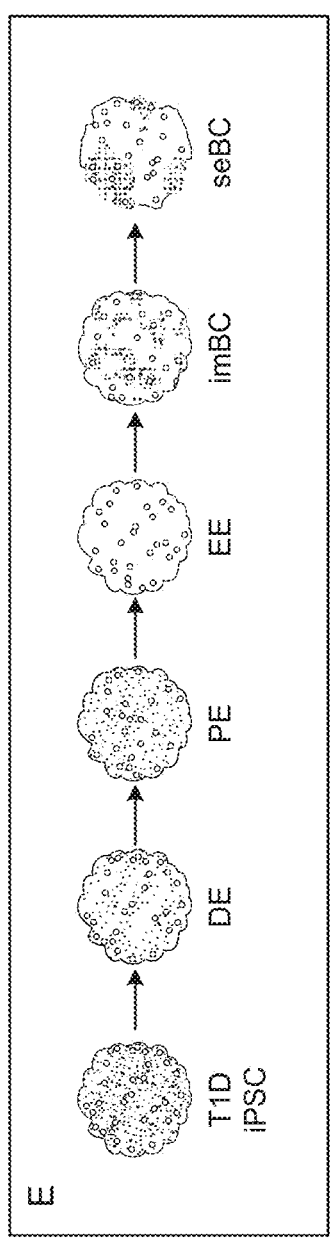
Figure 6:
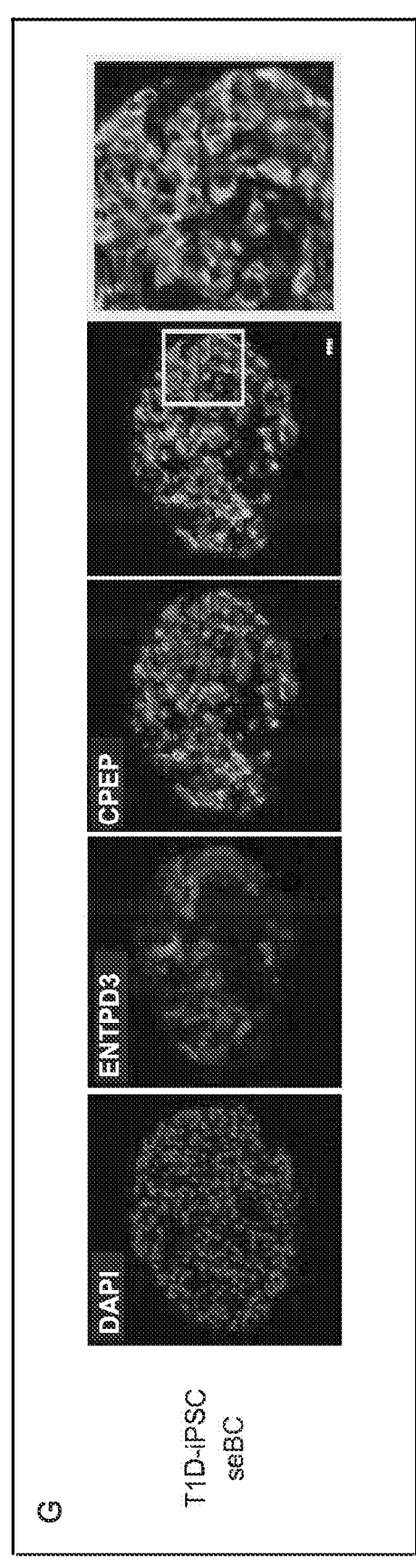

While the transgenic pINSGFP reporter line is an excellent research tool, its use for clinical applications may be limited. Thus, iPSCs were established from a donor with type 1 diabetes (T1D-iPSC) through episomal reprogramming of peripheral blood mononuclear cells (PBMC) as reported (FIGS. 14A-14F). T1D-iPSC were differentiated for 30 days using a differentiation protocol (described below) and protein expression of specific lineage markers at key differentiation stages was quantified by flow cytometry (FIG. 5E and FIG. 5F). Typically, by day 23 around 50% of cells were CPEP+NKX6.1+ indicating efficient production of sBC. After an additional seven days in culture, approximately 30% CPEP+ENTPD3+ cells could be readily identified (FIG. 5F). Immunofluorescence staining of the T1D- iPSC derived seBC revealed formation of INS+ENTPD3+ caps within clusters (FIG. 4G). Taken together, these data show that the surface protein ENTPD3 can be used as a marker to identify and FAC sort the most mature beta cell subpopulation of sBC; as characterized by gene expression, insulin storage, insulin bioprocessing, mtDNA copy number and beta cell function. In fact, INS+ENTPD3+ seBC are comparable to ENTPD3+ cadaveric beta cells sorted from human islets by a number of different assay parameters.

Example 5—Materials and Methods

Generation of Stem Cell Derived Beta-Like Cells from Human Embryonic Stem Cells

Undifferentiated MEL1 human embryonic stem cells (hESC) containing the INSGFP/W reporter 18 and subclones thereof 19,31 were maintained on hESC qualified Matrigel (Corning #354277) in mTESR1 or mTeSR+ media (STEMCELL Technologies #05826). Differentiation to stem cell-derived beta-like cells (sBCs) was carried out in suspension-based, low attachment suspension culture plates as described 19 or in a bioreactor magnetic stirring system (Reprocell #ABBWVS03A-6, #ABBWVDW-1013, #ABBWBP03NOS-6) as follows. Confluent hESC cultures were dissociated into single-cell suspension by incubation with TrypLE (Gibco #12-604-021) for 6 min at 37° C. Detached cells were quenched with mTESR media. Live cells were counted using a MoxiGo II cell counter (Orflow), followed by seeding $0.5 \times 10^6$ cells per ml in mTeSR media supplemented with 10 µM ROCK inhibitor (Y-27632, R&D Systems #1254-50) (cluster media). Bioreactors were placed on a magnetic stirring system set at 60 RPM in a cell culture incubator at 5% $CO_2$ to induce sphere formation for 48 h. To induce definitive endoderm differentiation, spheres were collected in a 50 mL Falcon tube, allowed to settle by gravity, washed once with RPMI (Gibco #11-875-093)+ 0.2% FBS, and re-suspended in d 0 media (RPMI containing 0.2% FBS, 1:5,000 ITS (Gibco #41400-045), 100 ng/mL Activin-A (R&D Systems #338-AC-01M), and 3 µM CHIR (STEMCELL Technologies #72054)). Differentiation media was changed daily by letting spheres settle by gravity for 3-10 min. ~80% of spent supernatant was removed by aspiration; fresh media was added, and bioreactors were placed back on stirrer system. sBC differentiation was based on published protocol (Russ, H. A. et al. Controlled induction of human pancreatic progenitors produces functional beta-like cells in vitro. *EMBO J.* 34, 1759-1772 (2015)) with modifications as outlined below. Differentiation medias are as: d 1 and 2, RPMI containing 0.2% FBS, 1:2,000 ITS, and 100 ng/LmL Activin A; d 3 and 4, RPMI containing 2% FBS, 1:1,000 ITS, and 25 ng/LmL KGF (Peprotech #100-19-1MG); d 5, DMEM with 4.5 g/L D-glucose (Gibco #11960-044) containing 1:100 SM1 (STEMCELL Technologies #5711), 1:100 NEAA (Gibco #11140-050), 1 mM Sodium Pyruvate (Gibco #11360-070), 1:100 GlutaMAX (Gibco #35050-061), 3 nM TTNPB, (R&D Systems #0761), 250 nM Sant-1 (R&D Systems #1974), 250 nM LDN (STEMCELL Technologies #72149), 30 nM PMA (Sigma Aldrich #P1585-1MG), 50 µg/mL 2-phospho-L-ascorbic acid trisodium salt (VitC) (Sigma #49752-10G); d6, DMEM with 4.5 g/L D-glucose containing 1:100 SM1, 1:100

NEAA, 1 mM Sodium Pyruvate, 1:100 GlutaMAX, 3 nM TTNPB and 50 μg/mL VitC; d 7, addition of 100 ng/mL EGF (R&D Systems #236-EG-01M) and 50 μg/mL VitC to existing media; d 8 and 9, DMEM containing 1:100 SM1, 1:100 NEAA, 1 mM Sodium Pyruvate, 1:100 GlutaMAX, 100 ng/mL EGF, 25 ng/mL KGF, and 50 μg/mL VitC; d 10-16 DMEM containing 2% fraction V BSA, 1:100 NEAA, 1 mM Sodium Pyruvate, 1:100 GlutaMAX, 1:100 ITS, 10 μg/ml Heparin (Sigma #H3149-250KU), 2 mM N-Acetyl-L-cysteine (Cysteine) (Sigma #A9165-25G), 10 μM Zinc sulfate heptahydrate (Zinc) (Sigma #Z0251-100g), 1×BME, 10 μM Alk5i II RepSox (R&D Systems #3742/50), 1 μM 3,3',5-Triiodo-L-thyronine sodium salt (T3) (Sigma #T6397), 0.5 μM LDN, 1 μM Gamma Secretase Inhibitor XX (XXi) (AsisChem #ASIS-0149) and 1:250 1 M NaOH to adjust pH to ~7.4; d 17 and up, CMRL (Gibco #11530-037) containing 1% BSA, 1:100 NEAA, 1 mM Sodium Pyruvate, 1:100 GlutaMAX, 10 μg/mL Heparin, 2 mM Cysteine, 10 μM Zinc, 1×BME, 10 μM Alk5i II RepSox, 1 μM T3, 50 μg/mL VitC, and 1:250 NaOH to adjust pH to ~7.4. All media contained 1× PenStrep (Gibco #15140-122). Media was changed every other day starting d11.

Generation of Stem Cell-Derived Beta-Like Cells from Induced Pluripotent Stem Cells Induced pluripotent stem cells (iPSC) were derived from PBMC isolated from a type-1 diabetes patient (T1D-iPSC) and reprogrammed as described 24 (FIGS. 14A-14F). iPSC were maintained on hESC qualified Matrigel in mTeSR+ media in 6 well plates. For differentiations 70-80% confluent cultures were washed with PBS and incubated in TrypLE for 8 min at 37° C. followed by quenching with mTeSR+. 0.5×10⁶ cells/mL in mTeSR media supplemented with 10 μM ROCK inhibitor were seeded and differentiated as per hESC bioreactor differentiation protocol above, with the following modifications: d 4 and 5, 50 ng/mL KGF instead of 25 ng/mL; d 7, DMEM containing 1:100 SM1, 1:100 NEAA, 1 mM Sodium Pyruvate, 1:100 GlutaMAX, 3 nM TTNPB and 50 μg/mL VitC; d8 and d9, DMEM containing 1:100 SM1, 1:100 NEAA, 1 mM Sodium Pyruvate, 1:100 GlutaMAX, 200 ng/ml EGF and 50 ng/mL KGF; d 10-16, DMEM containing 2% fraction V BSA, 1:100 NEAA, 1 mM Sodium Pyruvate, 1:100 GlutaMAX, 1:100 ITS, 10 μg/ml Heparin, 2 mM Cysteine, 10 μM Zinc, 1×BME, 10 μM Alk5i II RepSox, 1 μM T3, 0.5 μM LDN, 10 μM RI, 1 μM Xxi and 1:250 1 M NaOH to adjust pH to ~7.4; d 17 and up, CMRL (Gibco #11530-037) containing 1% BSA, 1:100 NEAA, 1 mM Sodium Pyruvate, 1:100 GlutaMAX, 10 μg/mL Heparin, 2 mM Cysteine, 10 μM Zinc, 1×BME, 10 μM Alk5i II RepSox, 1 μM T3, 50 μg/mL VitC, and 1:250 NaOH to adjust pH to ~7.4 (also referred to as maturation media). All media contained 1× PenStrep. Media was changed every other day starting d11.

Human Islet Culture—Two Sources of Human Islets (HIslet) were Used in this Study:

Human islets for research were provided by the Alberta Diabetes Institute Islet Core at the University of Alberta in Edmonton (at website bcell.org/isletcore) with the assistance of the Human Organ Procurement and Exchange (HOPE) program, *Trillium* Gift of Life Network (TGLN) and other Canadian organ procurement organizations. Islet isolation was approved by the Human Research Ethics Board at the University of Alberta (Pro00013094) 32,33.

Human pancreatic islets were provided by the NIDDK-funded Integrated Islet Distribution Program (IIDP) (RRID: SCR_014387) at City of Hope, NIH Grant #2UC4DK098085.

All donors' families gave informed consent for the use of pancreatic tissue in research (details of individual preps outlined in Methods Table 1). hIslet were cultured for up to 24 h in hIslet media (CMRL containing 1× Pen/Strep, 10% FBS, 100 μg/mL Gentamicin (Sigma #G1914), 1×BME) before analysis.

TABLE 1

| Unos ID/ Batch Type | ID | Purity (%) | Via-bility (%) | Islet type | BMI | Age (years) | Institute |
|---|---|---|---|---|---|---|---|
| RRID: SAMN 11476721 | HI033 | 90 | 95 | ND | 32.8 | 50 | The Scharp-Lacy Research Institute |
| RRID: SAMN 11523048 | HI034 | 95 | 95 | ND | 33.4 | 35 | The Scharp-Lacy Research Institute |
| RRID: SAMN 11578544 | HI035 | 75 | 95 | ND | 38.7 | 44 | Southern California Islet Cell Resources |
| R341 | HI043 | 95 | | ND | 30 | 42 | University of Alberta |
| 2296 | HI049 | 90 | 89 | ND | 29.2 | 52 | University of Alberta |
| 2301 | HI050 | 30 | 82 | ND | 29.9 | 49 | University of Alberta |

Reaggregation

Human Umbilical Vein Endothelial Cells (HUVEC) (Lonza #C2519A) human mesenchymal stem cells (hMSC) (Lonza #PT-2501) were grown as per manufactures instruction. For reaggregation experiments a total of 1,000 sBC were sorted and reaggregated with 100 hMSC and 400 HUVEC cells for 2 days in round bottom plates in a 50:50 mixture of maturation and HUVEC culture media as described previously 34.

Fluorescence Associated Cell Sorting (FACS)

pINSGFP/ENTPD3 Sorting pINSGFP clusters were collected in an Eppendorf tube, allowed to settle by gravity, the supernatant removed and then washed twice with PBS containing 2 mM EDTA (KD Medical #RGF-3130). Clusters were dissociated in 0.05% trypsin/EDTA (Lonza #cc3232) in 37° C. bead bath (Thermo Scientific) for 15 min. After 15 min cluster/trypsin solution was vortexed for 1 min, fresh trypsin added and then incubated for a further 5 min at 37° C. Finally, the suspension was pipetted up and down using a p1000 pipette until all clusters were fully dissociated. Cells were quenched immediately with ice cold culture media and spun down. Supernatant was removed and cells resuspend in FACS buffer (PBS containing 2% FBS and 2 mM EDTA). Cells were filtered through a 40 μm cell strainer into FACS tubes (Falcon #352235) for staining. For pINSGFP sorting, cells were incubated for 20 min on ice with DAPI (1:1000) then analyzed on BioRad S3e Cell Sorter; gating for live cells using DAPI and then pINSGFP on 488/FITC channel as per Micallef, et al. (INSGFP/w human embryonic stem cells facilitate isolation of in vitro derived insulin-producing cells. Diabetologia 55, 694-706 (2012)). For ENTPD3 sorting, cells were incubated for 20 min on ice with DAPI (1:1000) and in house conjugated ENTPD3-Alexa555 antibody. ENTPD3 antibody has been described by Saunders et al. (Ectonucleoside Triphosphate Diphosphohydrolase-3

Antibody Targets Adult Human Pancreatic β Cells for In Vitro and In Vivo Analysis. Cell Metab. 29, 745-754.e4 (2019)). Conjugation of ENTPD AB was done as per manufacture protocol (Thermo Fisher #A20187). Cells were gated for live cells, then pINSGFP expression and then ENTPD3 as outlined in FIGS. 4A-4N and FIGS. 10A-10I. Antibodies were used at concentrations indicated in Methods Table 2 with secondary antibodies of Table 3.

buffer, filtered through a 40 μm cell strainer into a FACS tube. Cells were first incubated with biotin labelled HPi1 (HICO-49F) antibody 17 for 20 min on ice, then washed with FACS buffer. Cells were then incubated for 20 min on ice with Streptavidin-PECy7, HIC3-2D1D-PE 17, ENTPD3-4888 antibodies and DAPI (1:1000). After incubation, cells were washed with FACS Buffer and resuspended in FACS Buffer. Populations were gated and sorted

TABLE 2

| Primary Antibodies Antigen | Species | Conjugate | Supplier | Cat no. | Dilution | Application |
|---|---|---|---|---|---|---|
| PDX1 | goat | — | R&D | AF2419 | 1:200 | IF |
| NKX6.1 | mouse | — | Hybridoma/DSHB | F55A10 | 1:200 | IF |
| cPEP | rat | — | Hybridoma/DSHB | GN-ID4 | 1:1000 | IF |
| NGN3 | sheep | — | R&D | AF3444 | 1:300 | IF |
| NKX2.2 | mouse | PE | BD | 564730 | 1:100 | IF |
| MAFA | rabbit | — | Cell Signaling | D2Z6N | 1:1000 | IF |
| NEUROD1 | mouse | 647 | BD | 563566 | 1:50 | IF |
| GCG | mouse | — | Sigma | 62654 | 1:1000 | IF |
| SST | rabbit | — | Phenoix Pharam | H-060-03 | 1:200 | IF |
| INS | guinea pig | — | Dako | A0564 | 1:500 | IF |
| mtTFA (F6) | mouse | — | Santa Cruz | sc-166965 | 1:100 | IF |
| ENTPD3 | mouse | — | Universite Laval | hN3-B3s | 1:50 | IF |
| ENTPD3 | mouse | alexa 555 | made in house | | 1:50 | FACS |
| ENTPD3 | mouse | alexa 488 | made in house | | 1:30 | FACS |
| HPI1 (HICO-49F) | mouse | biotin | Novus Biologicals | NBP1-18872B | 1:200 | FACS |
| HIC3-2D12 | — | PE | OHSU | OHSU 1873-A1 | 1:100 | FACS |
| FOXA2 | mouse | PE | BD Bioscience | 561589 | 1:200 | FC |
| SOX17 | mouse | alexa 488 | BD Bioscience | 562205 | 1:200 | FC |
| NKX6.1 | mouse | Alexa 647 | BD Bioscience | 563338 | 1:50 | FC |
| PDX1 | mouse | PE | BD Bioscience | 562161 | 1:25 | FC |
| cPEP | mouse | alexa 488 | made in house | | 1:100 | FC |
| ENTPD3 | mouse | alexa 555 | made in house | | 1:50 | FC |

TABLE 3

| Antigen | Con-jugate | Supplier | Cat no. | Dilution | Appli-cation |
|---|---|---|---|---|---|
| | | Secondary Antibodies | | | |
| anti-goat | alexa 647 | Thermo | A21447 | 1:1000 | IF |
| anti-mouse | alexa 555 | Thermo | A31570 | 1:1000 | IF |
| anti-rat | alexa 488 | Thermo | A21208 | 1:1000 | IF |
| anti-sheep | alexa 647 | Thermo | A21448 | 1:1000 | IF |
| anti-mouse | alexa555 | Thermo | A31570 | 1:1000 | IF |
| anti-rabbit | alexa 555 | Thermo | A31572 | 1:1000 | IF |
| anti-mouse | alexa 647 | Thermo | A31571 | 1:1000 | IF |
| anti-mouse | alexa 555 | Thermo | A31570 | 1:1000 | IF |
| anti-rabbit | alexa 647 | Thermo | A31573 | 1:1000 | IF |
| anti-guinea pig | alexa 488 | Thermo | A11073 | 1:1000 | IF |
| anti-mouse | alexa 555 | Thermo | A31570 | 1:1000 | IF |
| anti-mouse | alexa 555 | Thermo | A31570 | 1:1000 | IF |
| — | — | — | — | — | — |
| — | — | — | — | — | — |
| Streptavidin | PE-Cy7 | biolegend | 405206 | 1:200 | FACS |
| — | — | — | — | — | — |
| — | — | — | — | — | — |
| — | — | — | — | — | — |
| — | — | — | — | — | — |
| — | — | — | — | — | — |
| — | — | — | — | — | — |

Human Islet Sorting

Figure 11:
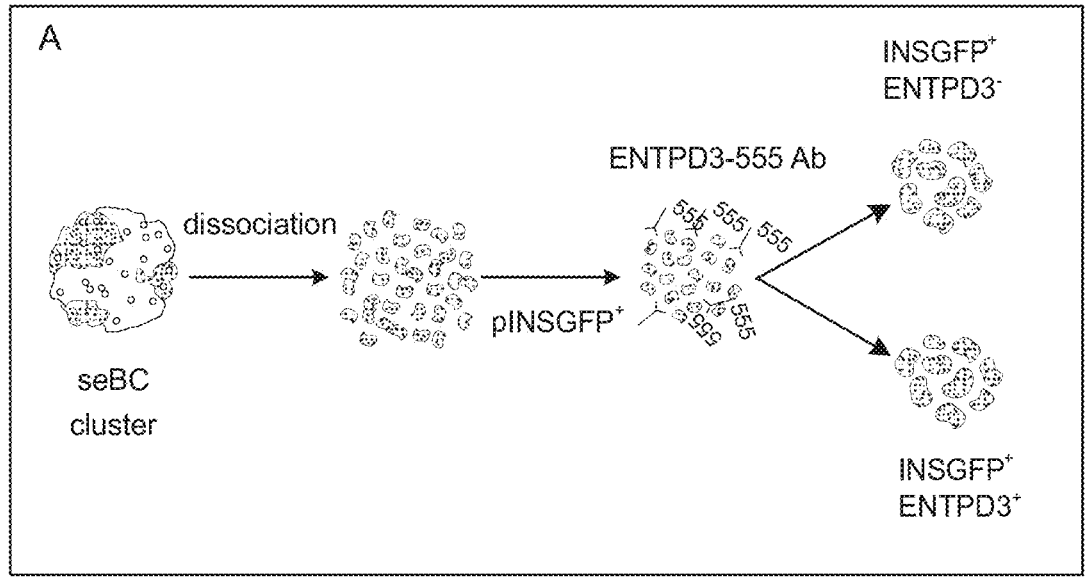
FIGS. 11A-11B depict ENTPD3 sorting strategy in pINSGFP reporter cell line.
Figure 11B:
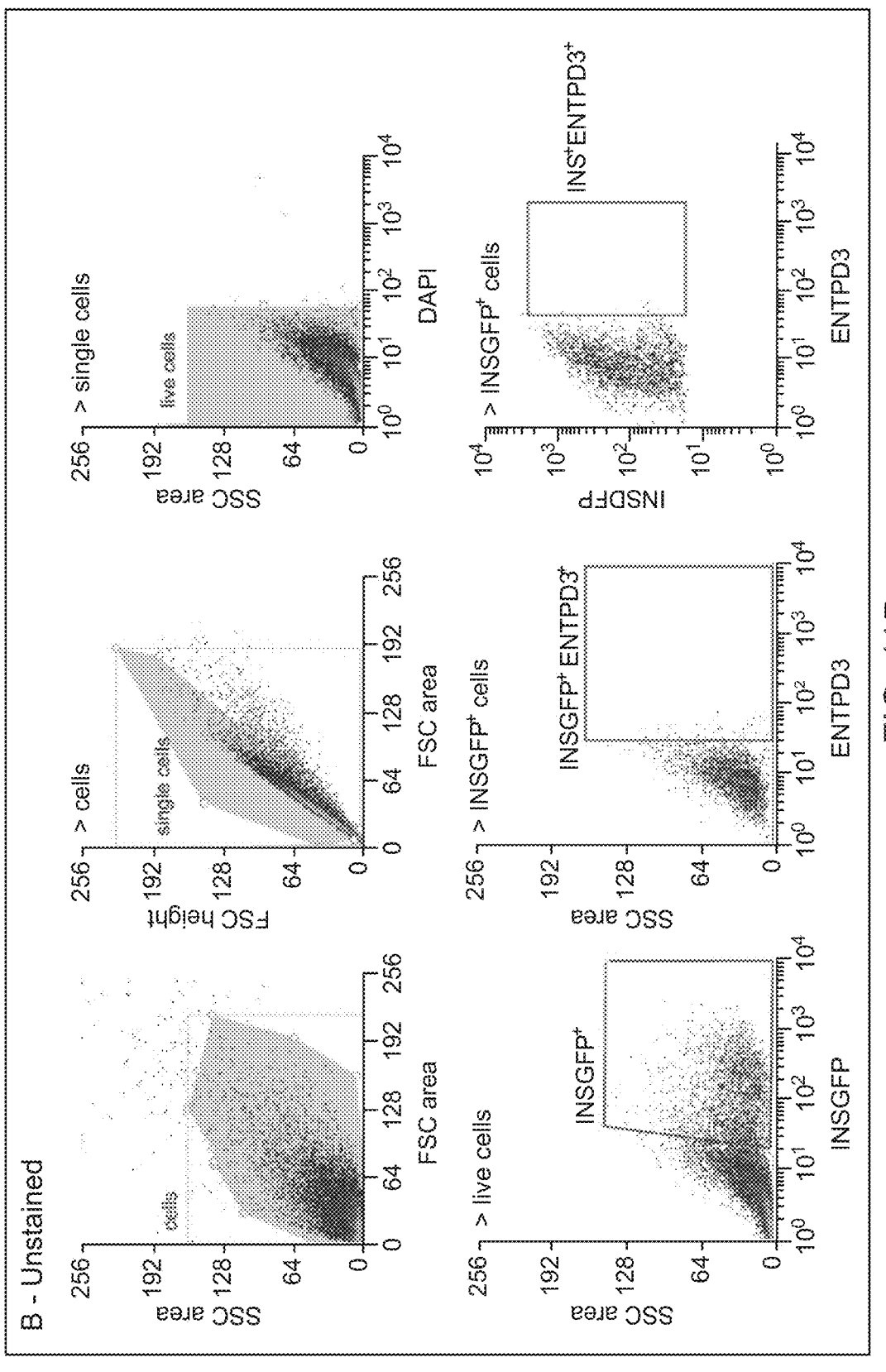
Figure 11B:
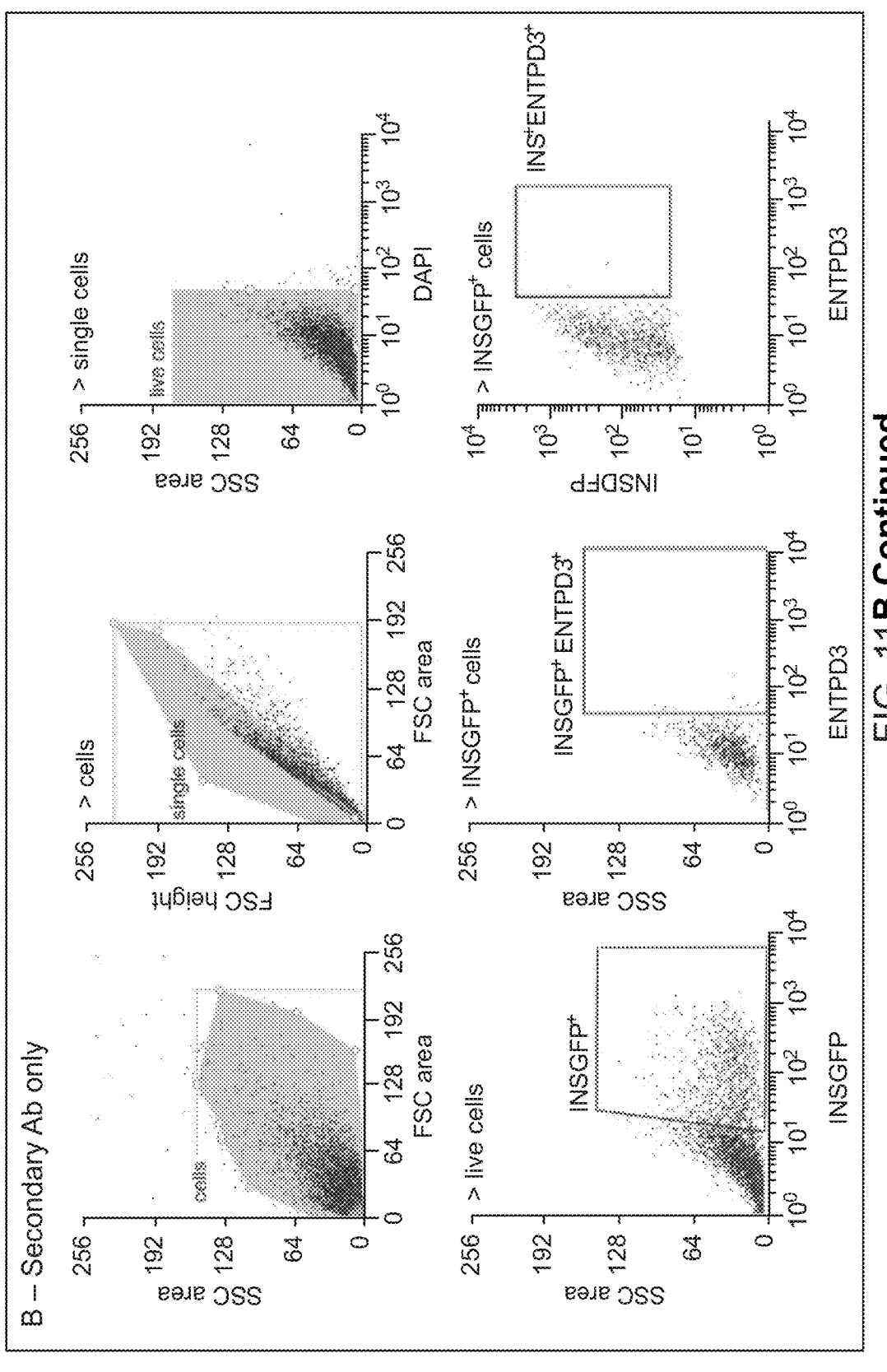
Figure 11B:
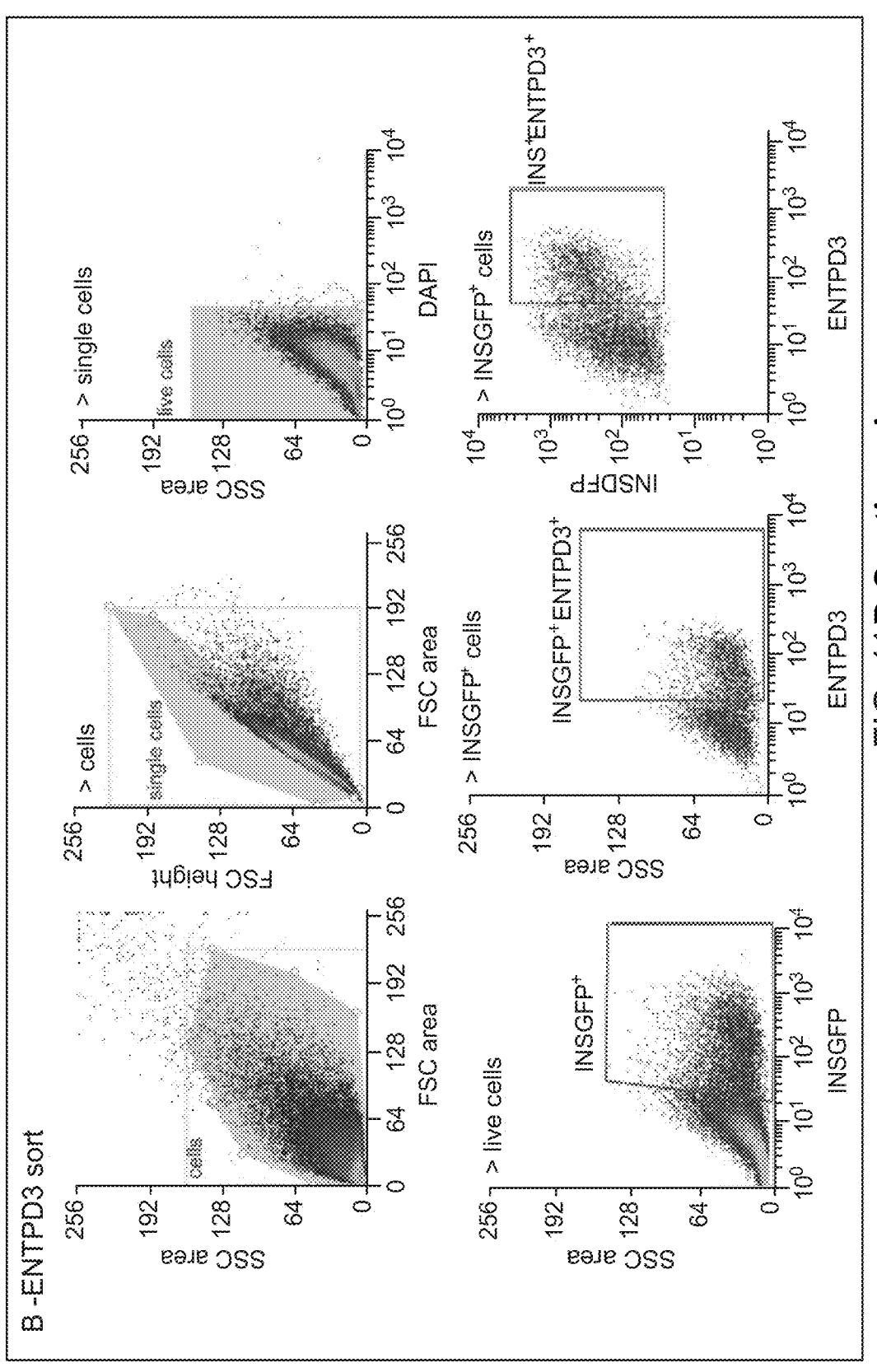
Figure 12C:
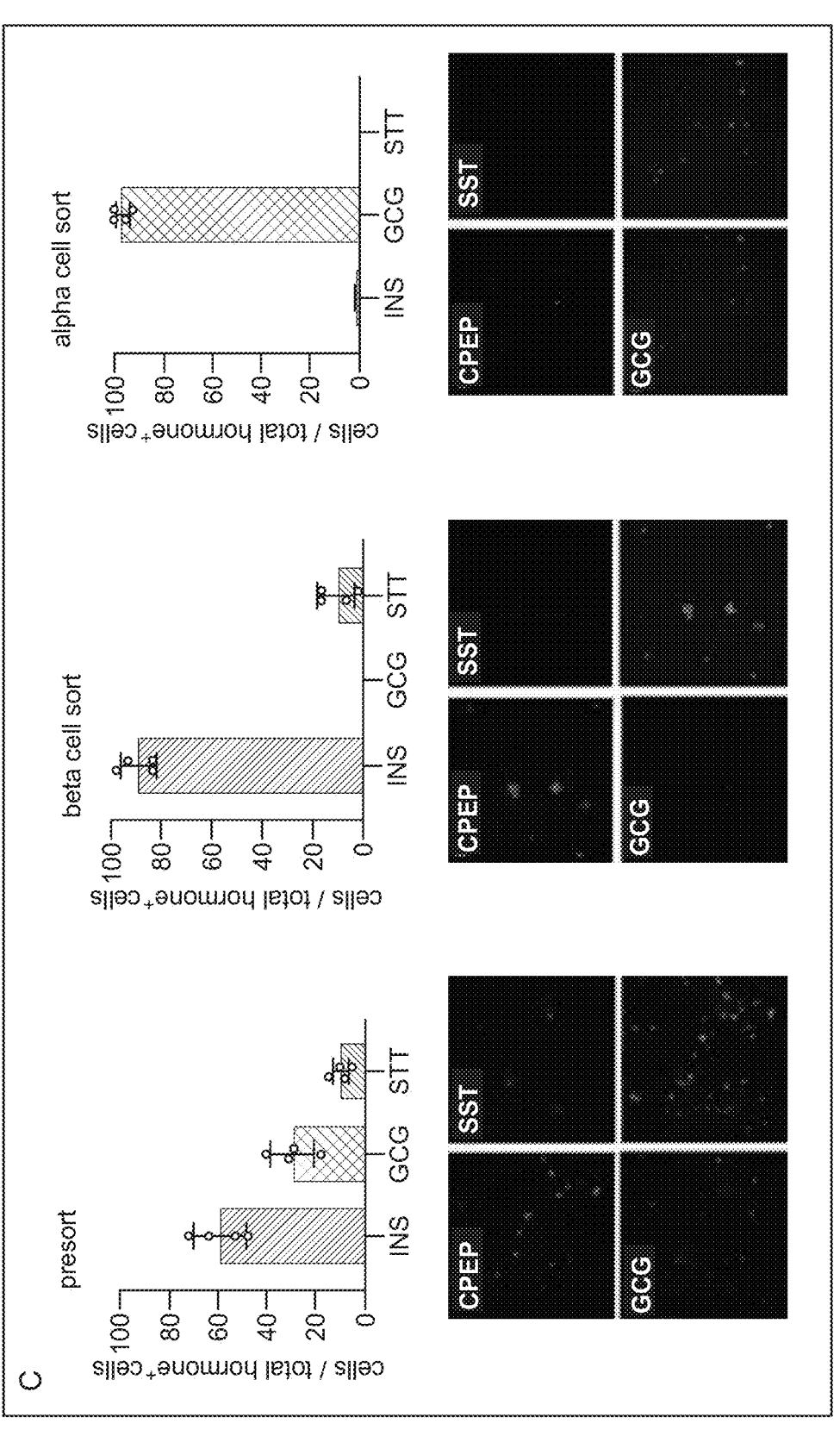

Human islets were collected in an Eppendorf tube, allowed to settle by gravity, the supernatant removed and then washed twice with PBS. The islets were dissociated in 500 μL of warm 0.05% trypsin for 15 min in a 37° C. bead bath—islets were pipetted up and down every 3 min using a p1000 pipette to aid dissociation. Single cells were quenched with culture media and resuspended in FACS on BioRad S3e Cell Sorter as per FIGS. 11A-11B. Antibodies were used at concentrations indicated in Methods Table. 2.

Cell Characterization

Flow Cytometry hESC and iPSC clusters were collected and dissociated as outlined above. Single cells were filtered through cell strainer into FACS tubes and incubated for 30 min on ice (or overnight at 4° C.) in conjugated antibody diluted in FACS buffer. After incubation the cells were washed and strained again through cell strainer and resuspended in FACS buffer for analyses on CYTEK Aurora.

Content Analysis

Total insulin and proinsulin content analyses were carried out on aliquots of 1,000 sorted pINSGFP+ cells lysed in acid ethanol using commercially available ELISA kits (insulin: Alpco 80-INSHU-E01.1 and proinsulin: 80-PINHUT-CH01).

Global 5-Hmc Analysis 500 cells were sorted into Eppendorf tubes and lysed by flash freezing pellets at –80° C. DNA was extracted using PicoPure DNA Extraction Kit (Thermo Fisher #KIT0103) and global 5-hmc percentage determined using Quest 5-hmc DNA ELISA kit (Zymo research #D5425) as per manufacturer's instructions.

Immunofluorescence sBC and human islet clusters were fixed for 20 min at room temperature with 4% paraformaldehyde then washed twice with PBS. Fixed clusters were then prepped for (i) whole mount staining or (ii) embedding and cryo-sectioning. (i) whole mount staining was performed in suspension by blocking for 30 min in CAS-block (Thermo Fisher #008102) with 0.2% Triton X-100 (Thermo Fisher #85111) then incubation in primary antibody solution (antibody diluted in CAS-block, 0.2% Triton X-100) overnight at 4° C. On the following day, the clusters were washed three times for 5 min in PBS containing 0.1% Tween-20 (PBS-T) (Sigma #P4417) and incubated in appropriate secondary antibody solution (antibody diluted in PBS-T and DAPI (1:1000)) for 2 h at room temperature. Clusters were then washed 2 times for 5 min in PBST and 1 time for 5 min in PBS and mounted with Vectashield (Vector #H2000) on glass slides. (ii) fixed clusters for cryo-sectioning were incubated overnight in 30% sucrose (Sigma #S0389) before embedding in tissue-tek OCT (Sakura #4583) and storing at −80° C. for minimum 2 h. OCT-blocks containing fixed clusters were cryo-sectioned (10 μm thickness) and transferred to glass slides. Blocking and staining of cryo-sections proceeded as per whole mount staining protocol above. Antibody dilutions were prepared as indicated in Table 2. Images were acquired using confocal microscopy (Carl Zeiss LSM 800) using 10, 20 and 40× objectives. Where appropriate, mean fluorescence intensity of individual clusters was calculated using Image J.

mtDNA Copy Number 500 cell were sorted into Eppendorf tubes and lysed by flash freezing pellets at −80° C. DNA was extracted using PicoPure DNA Extraction Kit (Thermo Fisher #KIT0103) and Human Mitochondrial DNA (mtDNA) Monitoring Primer Set (Takara #7246) used to quantify the relative number of copies of human mtDNA by real-time PCR, using genomic DNA (gDNA) as standard for normalization.

RT-qPCR

Total RNA was isolated using micro RNeasy kit (Qiagen #74104) and reverse transcribed using the iSCRIPT cDNA kit (BioRad #1708891) as per manufacturer's instructions. qPCR analysis was performed on BioRad CFX96 Real Time System using TaqMan probes (Thermo Fisher #4331182: Insulin Hs00355773_m1, ENTPD3 Hs00154325_m1 and GAPDH BioRad #10031285).

Single Cell RNA-Seq

Single cell RNA-seq libraries were generated using the 10× Genomics 3' end platform. Sequencing reads were processed using Cell Ranger (version 2.2.0) with the GRCh38 genome assembly to generate unique molecular identifier (UMI) gene count matrices per sample. The genome reference was supplemented with the eGFP coding sequence to enable detection of the pINS-eGFP transgene (GenBank U55761.1). Matrices were next processed using Seurat (version 2.3.0-3.0) to perform quality control filtering, normalization, tSNE projection, and clustering 35. Cells were removed if the UMI count or number of genes detected was less than 250, greater than 75,000, or if the proportion of UMIs mapped to mitochondrial genes was greater than 20%. Genes were excluded if they were detectable in fewer than 5 cells. Following filtering, the UMI counts were normalized to library size (total number of UMIs detected), scaled by 10,000, and log-transformed. Principal component analysis was performed on the Z scores of the normalized expression values, and the top 20 dimensions were selected for tSNE projection using a perplexity of 30. Graph-based clustering was performed using the top 20 principal components, with the 30 nearest neighbors, and a resolution of 0.5. Genes differentially expressed in each cluster compared with other clusters in each tested comparison were determined using a wilcox rank sum test and corrected for multiple hypothesis testing using Bonferroni correction (Seurat FindAllMarkers function). Cells were ordered in pseudotime using Monocle2 with the DDRTree method for dimensionality reduction (v2.10.0) 36. RNA velocity estimates were computed using the velocyto Python package 37. Canonical correlation analysis was performed using the RunCCA and AlignSubspace Seurat commands.

Bulk RNA Seq

Total RNA was isolated from cell cultures using RNeasy kits from Qiagen. Sequencing libraries were generated using the NEBNext Ultra II Directional RNA Library kit with NEBNext rRNA depletion. Paired-end sequencing reads were trimmed using cutadapt (v1.16 38, aligned using STAR (v 2.5.2a 39), and exonic read counts quantified using featureCounts from the subread package (v1.6.2 40). Differentially expressed genes were identified using DESeq2 (v1.24.0 41). Heatmaps were generated using ComplexHeatmap and ordered using hierarchical clustering of Euclidean distances with the complete method42.

GO Enrichment

Gene Ontology enrichment for single cell and bulk RNA-seq was conducted using gProfiler (43) using an ordered query with genes ranked by adjusted p-values.

Data and Resource Availability

The datasets generated during and/or analyzed during the current study are available in the NCBI's Gene Expression Omnibus database (GSE142290). Reviewer access token: wIalmegavnsIpmv. Analysis scripts and an interactive UCSC cell browser are provided at a GitHub repository (github.com/rnabioco/sebeta).

Functional Characterization

Calcium Imaging

Isolated clusters were loaded with 2 μM Rhod-2 AM (Invitrogen) for 35 min at 37° C. in imaging medium (125 mM NaCl, 5.7 mM KCl, 2.5 mM $CaCl_2$), 1.2 mM MgCl2, 10 mM HEPES, 2 mM glucose, and 0.1% BSA, pH 7.4) and were imaged in 35 mm glass bottom dishes maintained at 37° C. Rhod-2 fluorescence was imaged on a confocal microscope (Carl Zeiss LSM 800) with a 20×0.8 NA Plan Apochromat objective, 561 nm diode laser for excitation, and band pass emission filter of 568-700 nm. GFP fluorescence was imaged on the same microscope with a 488 nm diode laser for excitation with a band pass filter of 500-560 nm. Calcium images were acquired at ~1.5-3.5 sec/frame for 3 min at 2 mM glucose and for 10 min at 11 mM glucose after 20 min of glucose stimulation. Microscope settings (integration time, scan time, gain, laser power) were constant for all images collected within the same day.

Image Analysis

All images were analyzed similarly to previously published methods 21 with custom Matlab (Mathworks) scripts.

Activity Analysis

Images were smoothed using a 5×5 pixel averaging filter. Areas without significant Rhod-2 fluorescence were removed. Saturated areas were also removed by limiting the area to intensity below the maximum value. Photobleaching was adjusted for by removing any linear trend. Any islets with significant motion artifacts were removed (displacement of >0.5 cell width). For the time course of each 5×5 pixel region in the image with significant fluorescence, a peak detection algorithm was used to determine if the areas had peak amplitudes significantly above background. A region was considered 'active' if the corresponding time course for each pixel region had a peak amplitude >2.4× background. The fraction of active area was calculated as the number of pixels detected as 'active' normalized to the total number of pixels that showed significant fluorescence that were not saturated. Activity maps in FIGS. 2A-2I display peak amplitude normalized to average value of each 5×5 pixel region over time. This is only shown for areas of the islet determined as active. Fold change was determined by calculating the ratio of activity at 11 mM glucose to activity at 2 mM glucose.

Coordinated Area Analysis

Coordinated area was only calculated for active area at 11 mM glucose. Coordination was determined based on coincident timing of identified peaks, where areas were segmented by identified peaks occurring at similar time points. The cross correlation of the time courses for two 5×5 pixel sub-regions were taken. If the Pearson's correlation coefficient was >0.75, then the two sub-regions were considered highly coordinated and merged into a larger region. The coordinated area was calculated as the number of pixels in the largest area of coordination across the islet normalized to the total number of pixels that showed significant fluorescence that were not saturated.

Statistical Analysis

All statistical analysis was performed in Prism (Graphpad) or Matlab. First an F-test was used to determine if variances were equal then a student's t-test or welch t-test (for unequal variance) were utilized for assessing differences in activity, fold change in activity and coordination. A paired t-test was performed for activity when detecting differences between 2 and 11 mM glucose for the same islet. IQR outlier analysis was performed on 2 mM data for the imBC and seBC groups and outliers were removed from all data sets. Outliers were identified as any data point outside of [Q1–1.5×IQR, Q3+1.5×IQR] for each group, where Q1 and Q3 are the first and third quartiles.

Perifusion Assay

Dynamic insulin secretion was measured using a BioRep Technologies perifusion machine (PER14-02-0230-FA-ORB). 20-30 sBC clusters or human islets were placed on a filter in the perifusion chamber and various solutions were perifused through the system at 100 μL/min by a peristaltic pump; cells and solutions were kept at 37° C. The perifusion program consisted of a 1.5 h preincubation step with KRB buffer containing 0.5 mM Glucose followed by alternating high (16.7 mM) glucose, low (0.5 mM) glucose, exendin-4 (10 nM or 10 mM), and KCl (30 mM) solutions. Perifusion flow-through was collected in 96 well plates and stored at 4° C. for future analysis. Cell pellets were recovered from the chamber after perifusion and lysed with acid/ethanol solution over night at 4° C.

Ratio Calculation

Response to low glucose was calculated as the average insulin secretion read out for the initial 10 min low glucose incubation. The high glucose response was taken as the highest insulin secretion reached during the 20 min high glucose incubation. The KCl response was taken as the highest insulin secretion reached during the 5 min KCl incubation.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

What is claimed is:

1. A composition comprising a population of induced pluripotent stem cell-derived self-enriched β-like cells (seBCs) comprising: seBCs expressing INS and ENTPD3, wherein the seBCs do not express one or more of Glucagon, Somatostatin, Pancreatic polypeptide, and ghrelin and do not express one or more genes selected from the group consisting of SST, GCG, TPH1, and FEV and, wherein the seBCs form a cap over a population of cells comprising immature stem cell derived beta-like cells (imBCs) and wherein the seBCs population comprises from 20% to 30% differentiated mammalian β-cells and exhibit a first phase insulin release in response to greater than 5 mM and less than 20 mM glucose concentrations compared to imBCs.

2. The composition of claim 1, wherein the seBCs are not enriched by Fluorescence Associated Cell Sorting (FACS) sorting to achieve 20% to 30% differentiated mammalian β-cells.

3. The composition of claim 1, wherein an enriched population of seBCs comprises from 70% to 80% seBCs and further comprising one or more of other hormone producing cells, and support cells.

4. The composition of claim 1, wherein the composition is part of a pharmaceutical composition and further comprises a pharmaceutically acceptable excipient.

5. The composition of claim 3, wherein the support cells comprise one or more of mesenchymal cells, endothelial cells, pericytes cells, and nerve cells.

6. The composition of claim 1, wherein the expression of INS and ENTPD3 is at least 2 times up to 20 times greater than a non-enriched population of in vitro differentiated β-cells.

7. The composition of claim 1, wherein the seBCs comprise a first subpopulation wherein the seBCs expresses IGF2, a second subpopulation wherein the seBCs express CD9, and a third subpopulation wherein the seBCs express Ki67.

8. The composition of claim 1, wherein 30% of the seBCs express CPEP+ENTPD3+.

9. The composition of claim 1, wherein the seBCs express ENTPD3 1.1×-20× compared to immature sBCs.

10. The composition of claim 1, wherein the seBCs express INS 1.1×-100× compared to immature stem cell derived beta-like cells.

11. The composition of claim 1, wherein the seBCs exhibit a spike in insulin secretion in response to 16.7 mM glucose of between 2 and 10%.

12. The composition of claim 1, wherein the number of mitochondria in a population of the seBCs 1.1×, 1.2×, 1.3×, 1.4×, 1.5×, 1.6×, 1.7×, 1.8×, 1.9×, 2×, 3×, 4×, or 5× greater than in immature stem cell derived beta-like cells.

13. The composition of claim 1, comprising media without TGFbeta inhibition or the presence of T3 thyroid hormone.

* * * * *